(12) United States Patent
Yuan et al.

(10) Patent No.: US 11,202,723 B2
(45) Date of Patent: Dec. 21, 2021

(54) ABSORBENT ARTICLES WITH IMPROVED TOPSHEET DRYNESS

(71) Applicant: The Procter & Gamble Company, Cincinnati, OH (US)

(72) Inventors: Yi Yuan, Beijing (CN); Gueltekin Erdem, Beijing (CN); Silke Kramkowski, Bad Soden (DE); Ernesto Gabriel Bianchi, Oberursel Hessen (DE); Sascha Kreisel, Frankfurt am Main (DE)

(73) Assignee: The Procter & Gamble Company, Cincinnati, OH (US)

( * ) Notice: Subject to any disclaimer, the term of this patent is extended or adjusted under 35 U.S.C. 154(b) by 366 days.

(21) Appl. No.: 16/217,144

(22) Filed: Dec. 12, 2018

(65) Prior Publication Data

US 2019/0125595 A1 May 2, 2019

Related U.S. Application Data

(63) Continuation of application No. PCT/CN2016/088095, filed on Jul. 1, 2016.

(51) Int. Cl.
*A61F 13/15* (2006.01)
*A61F 13/511* (2006.01)
(Continued)

(52) U.S. Cl.
CPC ...... *A61F 13/51104* (2013.01); *A61F 13/513* (2013.01); *A61F 13/5121* (2013.01); *A61F 13/5123* (2013.01); *A61F 13/51464* (2013.01); *A61F 13/537* (2013.01); *A61F 13/5116* (2013.01); *A61F 2013/15463* (2013.01); *A61F 2013/15544* (2013.01); *A61F 2013/51139* (2013.01)

(58) Field of Classification Search
CPC ............ A61F 13/51104; A61F 13/5121; A61F 13/513; A61F 13/51464; A61F 13/5116; A61F 2013/15463; A61F 2013/15544; A61F 2013/51139
See application file for complete search history.

(56) References Cited

U.S. PATENT DOCUMENTS 3,485,706 A 12/1969 Evans
3,542,634 A 11/1970 Such
(Continued)

FOREIGN PATENT DOCUMENTS

CA 2294922 A1 12/1998
CN 1132471 A 10/1996
(Continued)

OTHER PUBLICATIONS

All Office Actions, U.S. Appl. No. 14/634,928.
(Continued)

*Primary Examiner* — Jacqueline F Stephens
(74) *Attorney, Agent, or Firm* — Christian M. Best

(57) ABSTRACT

Absorbent articles having three-dimensional, apertured, liquid permeable topsheets, acquisition materials, liquid permeable backsheets, and absorbent cores are disclosed. The absorbent articles provide improved topsheet dryness, reduced collagen rewet, and improved modified fluid acquisition.

20 Claims, 27 Drawing Sheets

(51) Int. Cl.
*A61F 13/512* (2006.01)
*A61F 13/513* (2006.01)
*A61F 13/537* (2006.01)
*A61F 13/514* (2006.01)

(56) References Cited

U.S. PATENT DOCUMENTS

| | | |
|---|---|---|
| 3,838,694 A | 10/1974 | Mesek |
| 3,860,003 A | 1/1975 | Buell |
| 3,929,135 A | 12/1975 | Thompson |
| 3,999,548 A | 12/1976 | Hernandez |
| 4,041,951 A | 8/1977 | Sanford |
| 4,324,246 A | 4/1982 | Mullane |
| 4,342,314 A | 8/1982 | Radel |
| 4,463,045 A | 7/1984 | Ahr |
| 4,558,888 A | 12/1985 | Hanson et al. |
| 4,589,876 A | 5/1986 | Van Tilburg |
| 4,610,678 A | 9/1986 | Weisman |
| 4,662,877 A | 5/1987 | Williams |
| 4,704,112 A | 11/1987 | Suzuki et al. |
| 4,731,066 A | 3/1988 | Korpman |
| 4,752,349 A | 6/1988 | Gebel |
| 4,773,905 A | 9/1988 | Molee et al. |
| 4,780,352 A | 10/1988 | Palumbo |
| 4,834,735 A | 5/1989 | Alemany |
| 4,859,519 A | 8/1989 | Cabe, Jr. |
| 4,868,958 A | 9/1989 | Suzuki |
| 4,950,264 A | 8/1990 | Osborn, III |
| 5,009,653 A | 4/1991 | Osborn, III |
| 5,019,066 A | 5/1991 | Freeland et al. |
| 5,021,051 A | 6/1991 | Hiuke |
| 5,134,007 A | 7/1992 | Reising et al. |
| 5,135,521 A | 8/1992 | Luceri |
| 5,158,819 A | 10/1992 | Goodman, Jr. |
| 5,221,274 A | 6/1993 | Buell et al. |
| 5,252,374 A | 10/1993 | Larsonneur |
| 5,264,268 A | 11/1993 | Luceri |
| 5,275,590 A | 1/1994 | Huffman et al. |
| 5,304,160 A | 4/1994 | Igaue et al. |
| 5,344,516 A | 9/1994 | Tanji et al. |
| 5,352,217 A | 10/1994 | Curro |
| H1376 H | 11/1994 | Osborn et al. |
| H1377 H | 11/1994 | Perry |
| 5,368,926 A | 11/1994 | Thompson |
| 5,397,318 A | 3/1995 | Dreier |
| 5,415,640 A | 5/1995 | Kirby et al. |
| 5,433,715 A | 7/1995 | Tanzer et al. |
| 5,449,352 A | 9/1995 | Nishino |
| 5,478,335 A | 12/1995 | Colbert |
| 5,514,105 A | 5/1996 | Goodman, Jr. et al. |
| 5,522,811 A | 6/1996 | Igaue et al. |
| 5,533,991 A | 7/1996 | Kirby et al. |
| 5,554,145 A | 9/1996 | Roe et al. |
| 5,558,661 A | 9/1996 | Roe et al. |
| 5,562,647 A | 10/1996 | Oetjen |
| 5,569,234 A | 10/1996 | Buell et al. |
| 5,580,411 A | 12/1996 | Nease et al. |
| 5,591,149 A | 1/1997 | Brown et al. |
| 5,599,335 A | 2/1997 | Goldman et al. |
| 5,601,546 A | 2/1997 | Tanji et al. |
| 5,607,414 A | 3/1997 | Richards et al. |
| 5,613,962 A | 3/1997 | Kenmochi et al. |
| 5,628,097 A | 5/1997 | Benson |
| 5,643,240 A | 7/1997 | Jackson et al. |
| 5,647,862 A | 7/1997 | Cree et al. |
| 5,662,633 A | 9/1997 | Doak et al. |
| 5,669,895 A | 9/1997 | Masuda et al. |
| 5,672,166 A | 9/1997 | Vandemoortele |
| 5,674,591 A | 10/1997 | James |
| 5,700,254 A | 12/1997 | McDowall et al. |
| 5,702,382 A | 12/1997 | Hines et al. |
| 5,713,884 A | 2/1998 | chappell et al. |
| 5,743,776 A | 4/1998 | Igaue et al. |
| 5,746,729 A | 5/1998 | Wada et al. |
| 5,772,650 A | 6/1998 | Mizutani |
| 5,779,692 A | 7/1998 | Hines et al. |
| 5,788,684 A | 8/1998 | Abuto |
| 5,795,349 A | 8/1998 | Hines et al. |
| 5,810,798 A | 9/1998 | Finch et al. |
| 5,810,800 A | 9/1998 | Hunter et al. |
| 5,824,004 A | 10/1998 | Chappel et al. |
| 5,830,203 A | 11/1998 | Suzuki et al. |
| 5,833,679 A | 11/1998 | Wada |
| 5,846,230 A | 12/1998 | Cree et al. |
| 5,846,232 A | 12/1998 | Serbiak et al. |
| 5,942,080 A | 8/1999 | Mortellite et al. |
| 5,951,536 A | 9/1999 | Osborn, III et al. |
| 5,961,505 A | 10/1999 | Coe et al. |
| 5,962,106 A | 10/1999 | De Carvalho et al. |
| 5,972,806 A | 10/1999 | Cree et al. |
| 5,990,375 A | 11/1999 | Lindquist et al. |
| 5,990,377 A | 11/1999 | Chen et al. |
| 6,004,306 A | 12/1999 | Robles et al. |
| 6,004,893 A | 12/1999 | Van Tilburg |
| 6,013,348 A | 1/2000 | Takai et al. |
| 6,022,338 A | 2/2000 | Putzer |
| 6,025,049 A | 2/2000 | Ouelette et al. |
| 6,048,600 A | 4/2000 | Hansson |
| 6,059,764 A | 5/2000 | Chappell et al. |
| 6,090,089 A | 7/2000 | Tsuji et al. |
| 6,103,953 A | 8/2000 | Buell et al. |
| 6,107,539 A | 8/2000 | Meyer et al. |
| 6,117,523 A | 9/2000 | Sugahara |
| 6,186,996 B1 | 2/2001 | Martin |
| 6,214,147 B1 | 4/2001 | Mortellite et al. |
| 6,231,948 B1 | 5/2001 | Ouellette et al. |
| 6,264,642 B1 | 7/2001 | Kuen et al. |
| 6,274,218 B1 | 8/2001 | Shimizu |
| 6,277,104 B1 | 8/2001 | Lasko et al. |
| 6,287,288 B1 | 9/2001 | Osborn et al. |
| 6,320,096 B1 | 11/2001 | Inoue et al. |
| 6,395,957 B1 | 5/2002 | Chen |
| 6,402,729 B1 | 6/2002 | Boberg et al. |
| 6,417,121 B1 | 7/2002 | Newkirk et al. |
| 6,436,080 B1 | 8/2002 | Carlucci et al. |
| 6,436,082 B1 | 8/2002 | Mizutani et al. |
| 6,436,083 B1 | 8/2002 | Mishima et al. |
| 6,446,495 B1 | 9/2002 | Herrlein et al. |
| 6,461,339 B1 | 10/2002 | Sugahara |
| 6,465,711 B1 | 10/2002 | Brisebois |
| 6,503,598 B1 | 1/2003 | Goda |
| 6,548,732 B2 | 4/2003 | Erdman et al. |
| 6,570,056 B1 | 5/2003 | Tanzer et al. |
| 6,573,423 B1 | 6/2003 | Herrlein et al. |
| 6,610,900 B1 | 8/2003 | Tanzer |
| 6,623,468 B2 | 9/2003 | Shimoe |
| 6,623,586 B2 | 9/2003 | Mortellite et al. |
| 6,632,504 B1 | 10/2003 | Gillespie et al. |
| 6,648,865 B1 | 11/2003 | Stiehl et al. |
| 6,685,688 B2 | 2/2004 | Mishima et al. |
| 6,686,512 B2 | 2/2004 | Herrlein et al. |
| 6,702,800 B1 | 3/2004 | Vukos et al. |
| 6,733,610 B2 | 5/2004 | Mizutani |
| 6,762,340 B2 | 7/2004 | Furuya et al. |
| 6,824,853 B1 | 11/2004 | Levine et al. |
| 6,840,928 B2 | 1/2005 | Datta et al. |
| 6,911,574 B1 | 6/2005 | Mizutani |
| 6,932,798 B2 | 8/2005 | Kudo et al. |
| 6,939,334 B2 | 9/2005 | Odorzynski et al. |
| 6,972,011 B2 | 12/2005 | Maeda |
| 6,974,891 B2 | 12/2005 | Wallstrom |
| 7,060,344 B2 | 6/2006 | Pourdeyhimi |
| 7,083,843 B2 | 8/2006 | Mizutani et al. |
| 7,102,054 B1 | 9/2006 | Cree et al. |
| 7,122,024 B2 | 11/2006 | Nakajima et al. |
| 7,163,528 B2 | 1/2007 | Christon et al. |
| 7,267,860 B2 | 9/2007 | Toyoshima et al. |
| D558,335 S | 12/2007 | Willhaus |
| 7,311,696 B2 | 12/2007 | Christon et al. |
| 7,371,919 B1 | 5/2008 | Busam et al. |
| 7,388,123 B2 | 6/2008 | Cowell et al. |
| 7,402,157 B2 | 7/2008 | Christon et al. |
| 7,422,991 B2 | 9/2008 | Baldauf et al. |
| 7,534,928 B2 | 5/2009 | Sakamoto et al. |

(56) References Cited

U.S. PATENT DOCUMENTS

| | | |
|---|---|---|
| 7,537,585 B2 | 5/2009 | Christon et al. |
| 7,569,264 B2 | 8/2009 | Toyoshima et al. |
| 7,589,249 B2 | 9/2009 | Gubermick et al. |
| 7,604,624 B2 | 10/2009 | Veith et al. |
| D603,611 S | 11/2009 | Cain et al. |
| 7,628,777 B2 | 12/2009 | Kondo et al. |
| 7,670,325 B2 | 3/2010 | Sugiyama et al. |
| 7,670,665 B2 | 3/2010 | Hoying et al. |
| 7,704,901 B2 | 4/2010 | Baldauf et al. |
| 7,712,640 B2 | 5/2010 | Honer et al. |
| 7,750,203 B2 | 7/2010 | Becker et al. |
| 7,767,876 B2 | 8/2010 | Davis et al. |
| 7,781,640 B2 | 8/2010 | Davis et al. |
| 7,785,310 B2 | 8/2010 | Sakano et al. |
| 7,786,340 B2 | 8/2010 | Gagiardi et al. |
| D624,179 S | 9/2010 | Molas et al. |
| 7,824,385 B2 | 11/2010 | Ecker et al. |
| 7,867,210 B2 | 1/2011 | Mori et al. |
| 7,935,861 B2 | 5/2011 | Suzuki |
| 7,967,801 B2 | 6/2011 | Hammons et al. |
| 7,972,317 B2 | 7/2011 | Christon et al. |
| D642,382 S | 8/2011 | Cain et al. |
| 7,993,317 B2 | 8/2011 | Hammons et al. |
| 7,993,319 B2 | 8/2011 | Sperl |
| 8,030,535 B2 | 10/2011 | Hammons et al. |
| 8,057,450 B2 | 11/2011 | Roe et al. |
| 8,057,455 B2 | 11/2011 | Shirai et al. |
| 8,058,501 B2 | 11/2011 | Hammons et al. |
| 8,105,300 B2 | 1/2012 | Christon et al. |
| 8,132,063 B2 | 3/2012 | Terao et al. |
| 8,178,748 B2 | 5/2012 | Hammons et al. |
| 8,193,407 B2 | 6/2012 | Mansfield et al. |
| 8,211,076 B2 | 7/2012 | Sugiyama et al. |
| 8,251,965 B2 | 8/2012 | Costea et al. |
| 8,257,330 B2 | 9/2012 | Christon et al. |
| 8,328,780 B2 | 12/2012 | Morman et al. |
| 8,377,023 B2 | 2/2013 | Sawyer et al. |
| D679,006 S | 3/2013 | Fuchs et al. |
| 8,393,374 B2 | 3/2013 | Sato et al. |
| D679,808 S | 4/2013 | Hood et al. |
| D681,197 S | 4/2013 | Johnson et al. |
| D681,199 S | 4/2013 | Cutshaw et al. |
| D681,200 S | 4/2013 | Cutshaw et al. |
| D682,420 S | 5/2013 | Abram et al. |
| 8,435,924 B2 | 5/2013 | Arora et al. |
| 8,439,886 B2 | 5/2013 | Hashino et al. |
| 8,450,556 B2 | 5/2013 | Miyamoto et al. |
| D684,262 S | 6/2013 | Mason et al. |
| 8,461,411 B2 | 6/2013 | DiGiacomantonio et al. |
| D686,317 S | 7/2013 | Bogren et al. |
| D686,319 S | 7/2013 | Hawes et al. |
| D686,320 S | 7/2013 | Hawes et al. |
| 8,481,806 B2 | 7/2013 | Ueminami et al. |
| 8,486,036 B2 | 7/2013 | Tange et al. |
| 8,491,556 B2 | 7/2013 | Popp et al. |
| 8,492,609 B2 | 7/2013 | Ecker et al. |
| 8,536,401 B2 | 9/2013 | Ecker et al. |
| 8,541,644 B2 | 9/2013 | Raidel et al. |
| D691,715 S | 10/2013 | Mason et al. |
| D692,130 S | 10/2013 | Biggs et al. |
| 8,546,642 B2 | 10/2013 | Biggs et al. |
| 8,556,874 B2 | 10/2013 | Christon et al. |
| 8,563,802 B2 | 10/2013 | Nishikawa et al. |
| 8,569,568 B2 | 10/2013 | Roe et al. |
| 8,569,572 B2 | 10/2013 | Hammons et al. |
| D693,922 S | 11/2013 | Frias et al. |
| 8,574,209 B2 | 11/2013 | Nishitani et al. |
| 8,575,419 B2 | 11/2013 | Di Virgilio et al. |
| 8,585,666 B2 | 11/2013 | Weisman et al. |
| 8,591,487 B2 | 11/2013 | Nishitani et al. |
| D695,894 S | 12/2013 | Bruno |
| 8,658,852 B2 | 2/2014 | Paldey |
| 8,748,692 B2 | 6/2014 | Suzuki |
| 8,865,965 B2 | 10/2014 | Sato et al. |
| 9,072,634 B2 | 7/2015 | Hundorf et al. |
| 9,220,638 B2 | 12/2015 | Hammons et al. |
| 9,237,973 B2 | 1/2016 | Abuto et al. |
| 9,480,608 B2 | 11/2016 | Kirby et al. |
| 9,629,755 B2 | 4/2017 | Kanya et al. |
| 9,649,232 B2 | 5/2017 | Hippe et al. |
| 10,195,092 B2 | 2/2019 | Tally et al. |
| 10,206,826 B2 | 2/2019 | Isele et al. |
| 10,285,874 B2 | 5/2019 | Tally et al. |
| 10,376,429 B2 | 8/2019 | Hao et al. |
| 10,617,576 B2 | 4/2020 | Close et al. |
| 2001/0021839 A1 | 9/2001 | Kashiwagi |
| 2001/0023342 A1 | 9/2001 | Suekane |
| 2001/0026861 A1 | 10/2001 | Takai et al. |
| 2002/0029025 A1 | 3/2002 | Furuya et al. |
| 2002/0040212 A1 | 4/2002 | Drevik |
| 2002/0064639 A1 | 5/2002 | Rearick et al. |
| 2002/0123728 A1 | 9/2002 | Graef et al. |
| 2002/0138054 A1 | 9/2002 | Erdman |
| 2002/0165516 A1 | 11/2002 | Datta et al. |
| 2003/0050615 A1 | 3/2003 | Sakamoto et al. |
| 2003/0050618 A1 | 3/2003 | Kondo et al. |
| 2003/0097107 A1 | 5/2003 | Sprengard-Eichel et al. |
| 2003/0114809 A1 | 6/2003 | Gagliardi |
| 2003/0114811 A1 | 6/2003 | Christon |
| 2003/0125696 A1 | 7/2003 | Morman et al. |
| 2003/0167044 A1 | 9/2003 | Toyoshima et al. |
| 2003/0187415 A1 | 10/2003 | Ito et al. |
| 2003/0187418 A1 | 10/2003 | Kudo et al. |
| 2004/0013852 A1 | 1/2004 | Curro et al. |
| 2004/0039363 A1 | 2/2004 | Sugiyama et al. |
| 2004/0054343 A1 | 3/2004 | Barnett et al. |
| 2004/0102755 A1 | 5/2004 | Morman et al. |
| 2004/0116029 A1 | 6/2004 | Kelly |
| 2004/0122396 A1 | 6/2004 | Maldonado et al. |
| 2004/0131820 A1 | 7/2004 | Turner et al. |
| 2004/0140047 A1 | 7/2004 | Sato |
| 2004/0142151 A1 | 7/2004 | Toyoshima et al. |
| 2004/0186449 A1 | 9/2004 | Brisebois |
| 2004/0254554 A1 | 12/2004 | Mavinkurve |
| 2004/0265533 A1 | 12/2004 | Hoying et al. |
| 2005/0003152 A1 | 1/2005 | Thomas |
| 2005/0084439 A1 | 4/2005 | Yasuo |
| 2005/0124961 A1 | 6/2005 | Morman et al. |
| 2005/0137556 A1 | 6/2005 | Brisebois |
| 2005/0148975 A1 | 7/2005 | Van Gompel et al. |
| 2005/0154362 A1 | 7/2005 | Warren et al. |
| 2005/0215155 A1 | 9/2005 | Young et al. |
| 2006/0161122 A1 | 7/2006 | Erdman |
| 2006/0216473 A1 | 9/2006 | Tomany et al. |
| 2007/0048709 A1 | 3/2007 | Ales et al. |
| 2007/0093770 A1 | 4/2007 | Ecker et al. |
| 2007/0142812 A1 | 6/2007 | Popp et al. |
| 2007/0233027 A1 | 10/2007 | Roe et al. |
| 2007/0298220 A1 | 12/2007 | Noda |
| 2008/0004581 A1 | 1/2008 | Babusik et al. |
| 2008/0114317 A1 | 5/2008 | Seyler |
| 2008/0195070 A1 | 8/2008 | Ponomarenko |
| 2008/0243100 A1 | 10/2008 | Wu et al. |
| 2008/0249494 A1 | 10/2008 | Digiacomantonio et al. |
| 2008/0249495 A1 | 10/2008 | DiVirgilio et al. |
| 2008/0029413 A1 | 11/2008 | Andersson et al. |
| 2008/0300564 A1 | 12/2008 | Bogren et al. |
| 2008/0312621 A1 | 12/2008 | Hundorf et al. |
| 2008/0312622 A1* | 12/2008 | Hundorf ............ A61F 13/5323 604/366 |
| 2008/0312623 A1 | 12/2008 | Hundorf |
| 2009/0030390 A1 | 1/2009 | Hammons et al. |
| 2009/0030391 A1 | 1/2009 | Hammons et al. |
| 2009/0131896 A1 | 5/2009 | Ebitsuka et al. |
| 2009/0182297 A1 | 7/2009 | Hedstroem et al. |
| 2009/0209930 A1 | 8/2009 | Hammons et al. |
| 2009/0221979 A1 | 9/2009 | Huang |
| 2009/0306614 A1 | 12/2009 | Boissier |
| 2009/0306615 A1 | 12/2009 | Olsson |
| 2010/0004615 A1 | 1/2010 | Boissier |
| 2010/0036338 A1 | 2/2010 | Hammons |
| 2010/0036349 A1 | 2/2010 | Hammons |
| 2010/0063471 A1 | 3/2010 | Minato et al. |
| 2010/0069871 A1 | 3/2010 | Minato et al. |

(56) References Cited

U.S. PATENT DOCUMENTS

| | | |
|---|---|---|
| 2010/0106127 A1 | 4/2010 | Minato et al. |
| 2010/0130952 A1 | 5/2010 | Murai |
| 2010/0209664 A1 | 8/2010 | Sato |
| 2010/0249740 A1 | 9/2010 | Miyamoto et al. |
| 2011/0046592 A1 | 2/2011 | Nishikawa et al. |
| 2011/0046596 A1 | 2/2011 | Kudo et al. |
| 2011/0073513 A1 | 3/2011 | Weisman et al. |
| 2011/0094669 A1 | 4/2011 | Oetjen |
| 2011/0010603 A1 | 5/2011 | Stahl et al. |
| 2011/0160691 A1 | 6/2011 | Ng et al. |
| 2011/0001963 A1 | 8/2011 | Hammons et al. |
| 2012/0029454 A1 | 2/2012 | Li |
| 2012/0041406 A1 | 2/2012 | Alkmin |
| 2012/0059343 A1 | 3/2012 | Kume |
| 2012/0064280 A1 | 3/2012 | Hammons et al. |
| 2012/0095426 A1 | 4/2012 | Visscher et al. |
| 2012/0100350 A1 | 4/2012 | Shim |
| 2012/0226250 A1 | 9/2012 | Sato et al. |
| 2012/0002963 A1 | 11/2012 | Choo et al. |
| 2012/0310199 A1 | 12/2012 | Larson et al. |
| 2012/0310200 A1 | 12/2012 | Christon et al. |
| 2012/0316532 A1 | 12/2012 | Mccormick |
| 2013/0116646 A1 | 5/2013 | Robles |
| 2013/0131620 A1 | 5/2013 | Hisanaka et al. |
| 2013/0158494 A1 | 6/2013 | Ong et al. |
| 2013/0184667 A1 | 7/2013 | Larson et al. |
| 2013/0184668 A1 | 7/2013 | Hood et al. |
| 2013/0197462 A1 | 8/2013 | Abuto et al. |
| 2013/0211362 A1 | 8/2013 | Mason et al. |
| 2013/0226123 A1 | 8/2013 | Kudo et al. |
| 2013/0245587 A1 | 9/2013 | DiGiacomantonio et al. |
| 2013/0002615 A1 | 10/2013 | Lee et al. |
| 2013/0261585 A1 | 10/2013 | Lee et al. |
| 2013/0261586 A1 | 10/2013 | Lee et al. |
| 2013/0296820 A1 | 11/2013 | Hughes et al. |
| 2013/0310784 A1 | 11/2013 | Bryant et al. |
| 2014/0005625 A1 | 1/2014 | Wirtz |
| 2014/0031779 A1 | 1/2014 | Hammons et al. |
| 2014/0039434 A1 | 2/2014 | Xu et al. |
| 2014/0039438 A1 | 2/2014 | Ferrer et al. |
| 2014/0044934 A1 | 2/2014 | Bills |
| 2014/0072767 A1 | 3/2014 | Klaska et al. |
| 2014/0121623 A1 | 5/2014 | Kirby |
| 2014/0121624 A1 | 5/2014 | Kirby et al. |
| 2014/0121626 A1 | 5/2014 | Finn |
| 2014/0127459 A1 | 5/2014 | Xu et al. |
| 2014/0127460 A1 | 5/2014 | Xu et al. |
| 2014/0127461 A1 | 5/2014 | Xu et al. |
| 2014/0163500 A1 | 6/2014 | Roe et al. |
| 2014/0163503 A1 | 6/2014 | Arizti et al. |
| 2014/0163507 A1 | 6/2014 | Kudo et al. |
| 2014/0296815 A1 | 10/2014 | Takken |
| 2014/0336608 A1 | 11/2014 | Hao et al. |
| 2014/0343525 A1 | 11/2014 | Roh et al. |
| 2015/0038933 A1 | 2/2015 | Lee et al. |
| 2015/0038934 A1 | 2/2015 | Lee et al. |
| 2015/0039020 A1 | 2/2015 | ValMalderen |
| 2015/0065984 A1 | 3/2015 | Tamura et al. |
| 2015/0080822 A1* | 3/2015 | Ehrnsperger ............ A61F 13/15 604/366 |
| 2015/0080837 A1 | 3/2015 | Rosati et al. |
| 2015/0080839 A1 | 3/2015 | Trapp et al. |
| 2015/0250658 A1 | 9/2015 | Tally et al. |
| 2015/0250659 A1 | 9/2015 | Tally et al. |
| 2015/0250662 A1* | 9/2015 | Isele .................. A61F 13/5121 604/378 |
| 2015/0250663 A1 | 9/2015 | Wagner et al. |
| 2015/0290050 A1 | 10/2015 | Wada |
| 2016/0074237 A1 | 3/2016 | Rosati et al. |
| 2016/0074238 A1 | 3/2016 | Rosati et al. |
| 2016/0074240 A1 | 3/2016 | Rosati et al. |
| 2016/0074241 A1 | 3/2016 | Rosati et al. |
| 2016/0074244 A1 | 3/2016 | Rosati et al. |
| 2016/0074245 A1 | 3/2016 | Rosati et al. |
| 2016/0074246 A1 | 3/2016 | Rosati et al. |
| 2016/0074247 A1 | 3/2016 | Rosati |
| 2016/0074248 A1 | 3/2016 | Rosati et al. |
| 2016/0074249 A1 | 3/2016 | Rosati et al. |
| 2016/0074250 A1 | 3/2016 | Strube et al. |
| 2016/0074257 A1 | 3/2016 | Orr et al. |
| 2016/0074258 A1 | 3/2016 | Rosati et al. |
| 2016/0074259 A1 | 3/2016 | Rosati et al. |
| 2016/0153128 A1 | 6/2016 | Xie et al. |
| 2016/0153218 A1 | 6/2016 | Kondi et al. |
| 2016/0175170 A1 | 6/2016 | Close et al. |
| 2016/0175172 A1 | 6/2016 | Hao et al. |
| 2017/0014281 A1 | 1/2017 | Xie et al. |
| 2017/0056256 A1 | 3/2017 | Smith |
| 2018/0271719 A1 | 9/2018 | Yuan et al. |
| 2019/0099305 A1 | 4/2019 | Isele et al. |
| 2019/0117474 A1 | 4/2019 | Isele et al. |
| 2019/0231613 A1 | 8/2019 | Tally et al. |

FOREIGN PATENT DOCUMENTS

| | | |
|---|---|---|
| CN | 1184413 A | 6/1998 |
| CN | 1054897 | 7/2000 |
| CN | 1286602 A | 3/2001 |
| CN | 1305361 A | 7/2001 |
| CN | 1132561 | 12/2003 |
| CN | 1197538 | 4/2005 |
| CN | 1280470 | 10/2006 |
| CN | 1290478 | 12/2006 |
| CN | 1981723 | 6/2007 |
| CN | 1331661 | 8/2007 |
| CN | 101119757 A | 2/2008 |
| CN | 101152114 | 4/2008 |
| CN | 100387212 | 5/2008 |
| CN | 100434055 | 11/2008 |
| CN | 100512784 | 7/2009 |
| CN | 100522122 | 8/2009 |
| CN | 1981724 | 5/2010 |
| CN | 101889924 A | 11/2010 |
| CN | 201692175 | 1/2011 |
| CN | 1839776 | 4/2011 |
| CN | 201959103 | 9/2011 |
| CN | 102257199 | 11/2011 |
| CN | 1986210 | 6/2012 |
| CN | 102560904 | 7/2012 |
| CN | 102673030 | 9/2012 |
| CN | 202491475 | 10/2012 |
| CN | 202637294 | 1/2013 |
| CN | 101674793 | 10/2013 |
| CN | 101310696 | 12/2013 |
| CN | 103417337 | 12/2013 |
| CN | 103417338 | 12/2013 |
| CN | 203393410 | 1/2014 |
| CN | 203400265 | 1/2014 |
| CN | 103908376 | 7/2014 |
| CN | 207295240 U | 5/2018 |
| EP | 1946734 A1 | 7/2008 |
| GB | 2262235 | 6/1993 |
| GB | 2325146 | 11/1998 |
| JP | H02142564 A | 5/1990 |
| JP | H4187146 | 7/1992 |
| JP | 8117273 | 5/1996 |
| JP | 11197179 A1 | 7/1999 |
| JP | 3155351 | 4/2001 |
| JP | 2002512082 A | 4/2002 |
| JP | 2002369839 A | 12/2002 |
| JP | 2003116909 A | 4/2003 |
| JP | 3437681 | 8/2003 |
| JP | 3453031 | 10/2003 |
| JP | 3517852 | 4/2004 |
| JP | 3587831 B2 | 11/2004 |
| JP | 3611666 | 1/2005 |
| JP | 2006014887 A | 1/2006 |
| JP | 3740790 | 2/2006 |
| JP | 3808032 | 8/2006 |
| JP | 3812460 | 8/2006 |
| JP | 2007014705 | 1/2007 |
| JP | 3877682 | 2/2007 |
| JP | 3886400 | 2/2007 |
| JP | 3886466 | 2/2007 |

(56) References Cited

FOREIGN PATENT DOCUMENTS

| | | |
|---|---|---|
| JP | 3926250 | 6/2007 |
| JP | 3987691 | 10/2007 |
| JP | 3989218 | 10/2007 |
| JP | 4023996 | 12/2007 |
| JP | 4090412 | 5/2008 |
| JP | 2008161254 A | 7/2008 |
| JP | 2008522772 A | 7/2008 |
| JP | 4178738 | 11/2008 |
| JP | 4185389 | 11/2008 |
| JP | 2009201760 A | 9/2009 |
| JP | 4346633 | 10/2009 |
| JP | 4390747 B2 | 10/2009 |
| JP | 2009219641 A | 10/2009 |
| JP | 4390406 | 12/2009 |
| JP | 4390624 | 12/2009 |
| JP | 2010106430 A | 5/2010 |
| JP | 4514630 | 7/2010 |
| JP | 4540567 | 9/2010 |
| JP | 4566109 | 10/2010 |
| JP | 2011000279 A | 1/2011 |
| JP | 4627500 | 2/2011 |
| JP | 4627502 | 2/2011 |
| JP | 4646878 | 3/2011 |
| JP | 4688103 | 5/2011 |
| JP | 4700507 | 6/2011 |
| JP | 4716638 | 7/2011 |
| JP | 4716639 | 7/2011 |
| JP | 4746833 | 8/2011 |
| JP | 4808504 | 11/2011 |
| JP | 4975091 | 7/2012 |
| JP | 4990070 | 8/2012 |
| JP | 5021719 | 9/2012 |
| JP | 5063412 | 10/2012 |
| JP | 4808501 | 11/2012 |
| JP | 5074854 | 11/2012 |
| JP | 5078325 | 11/2012 |
| JP | 5084434 | 11/2012 |
| JP | 5086035 | 11/2012 |
| JP | 5086036 | 11/2012 |
| JP | 5087419 | 12/2012 |
| JP | 5087432 | 12/2012 |
| JP | 5099752 | 12/2012 |
| JP | 5103100 | 12/2012 |
| JP | 5112047 | 1/2013 |
| JP | 5149057 | 2/2013 |
| JP | 5230238 | 7/2013 |
| JP | 5394654 | 1/2014 |
| JP | 5410852 | 2/2014 |
| JP | 5468654 | 4/2014 |
| JP | 5528953 | 6/2014 |
| WO | WO 1993-11725 | 6/1993 |
| WO | WO 1994-20054 | 9/1994 |
| WO | WO 1996-23472 | 8/1996 |
| WO | 9626698 A1 | 9/1996 |
| WO | WO1996-036761 | 11/1996 |
| WO | WO 1998-15399 | 4/1998 |
| WO | WO 1999-00095 | 1/1999 |
| WO | 9907318 A1 | 2/1999 |
| WO | WO 2001-06974 | 2/2001 |
| WO | WO 2007-027219 | 3/2007 |
| WO | 2009062998 A1 | 5/2009 |
| WO | WO 2010-0055699 | 5/2010 |
| WO | WO 2011-0122710 | 10/2011 |
| WO | 2012043842 A1 | 4/2012 |
| WO | WO 2012-0176656 | 12/2012 |
| WO | WO 2013-091150 | 6/2013 |
| WO | WO 2013-099625 | 7/2013 |
| WO | WO 2013-129167 | 9/2013 |
| WO | WO 2013-147222 | 10/2013 |
| WO | WO 2013-191077 | 12/2013 |
| WO | 2014085974 A1 | 6/2014 |
| WO | 2015094623 A1 | 6/2015 |

OTHER PUBLICATIONS

International Search Report and Written Opinion, PCT/CN2016/088095.
Supplemental International Search Report, PCT/CN2016/088095.
All Office Actions, U.S. Appl. No. 15/922,093.
All Office Actions, U.S. Appl. No. 16/223,616.
All Office Actions, U.S. Appl. No. 17/319,122.
All Office Actions, U.S. Appl. No. 14/634,945.
All Office Actions, U.S. Appl. No. 14/634,954.
All Office Actions, U.S. Appl. No. 14/634,985.
All Office Actions, U.S. Appl. No. 15/232,901.
All Office Actions, U.S. Appl. No. 16/207,401.
All Office Actions, U.S. Appl. No. 16/378,815.
Unpublished U.S. Appl. No. 17/319,122, filed May 13, 2021, to first inventor Olaf Erik Isele et al.

* cited by examiner

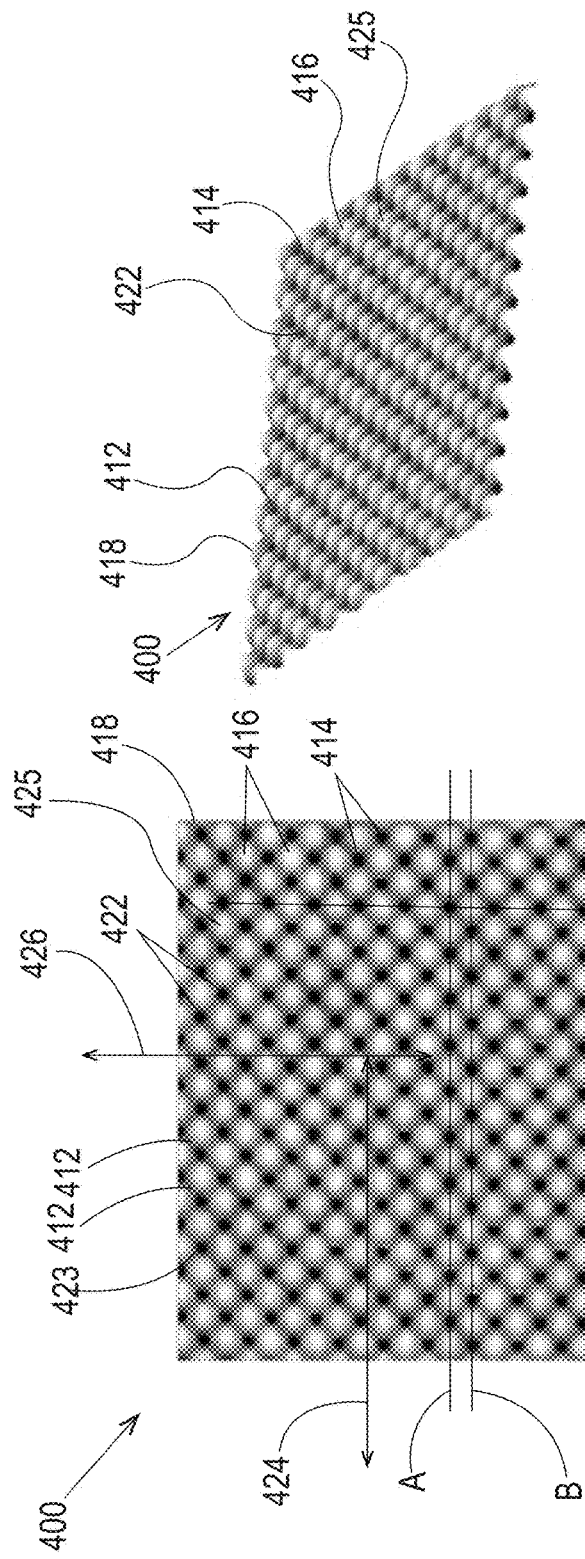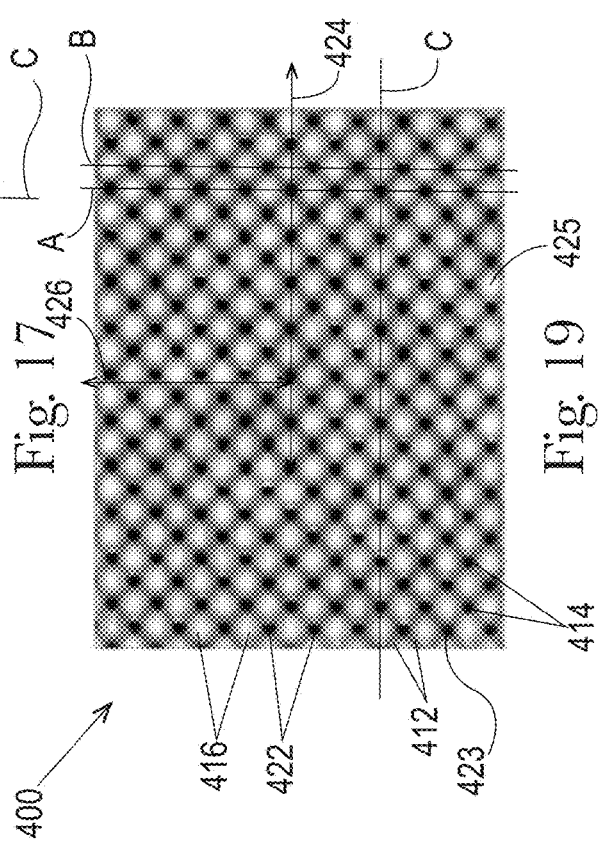

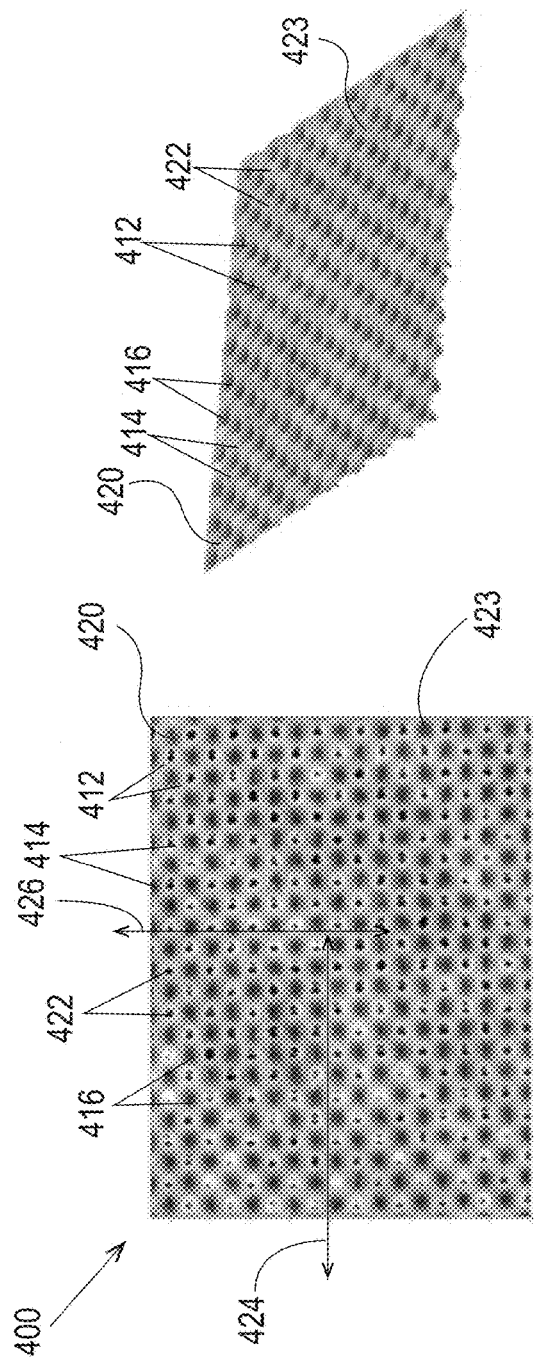
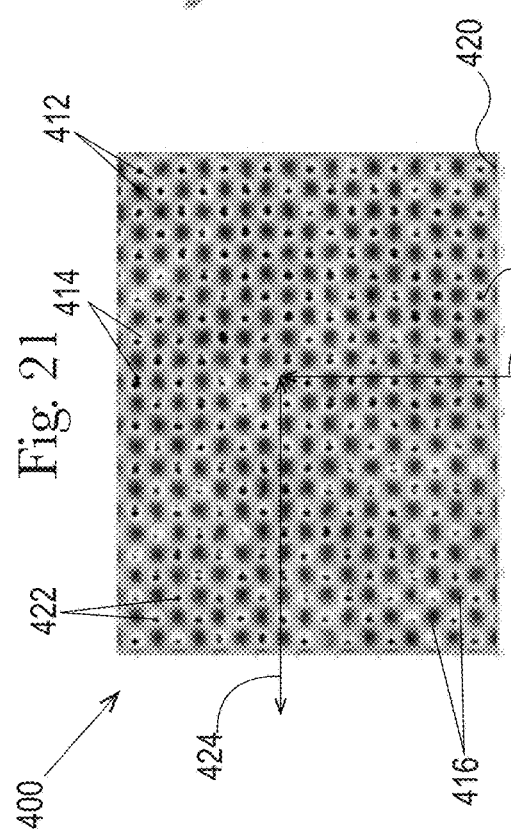
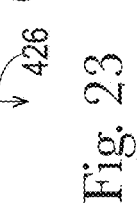

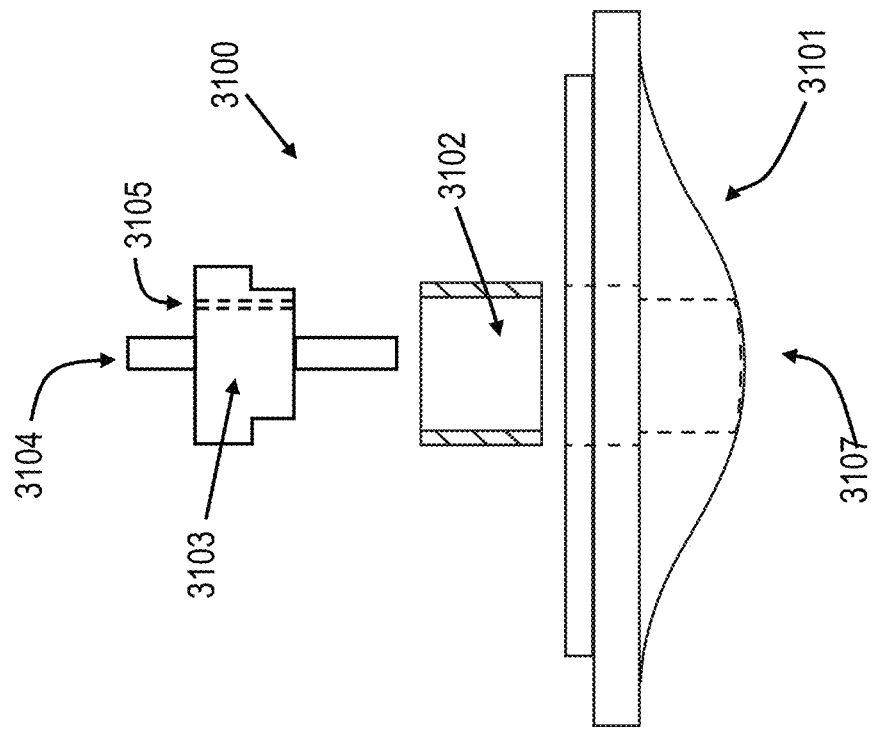
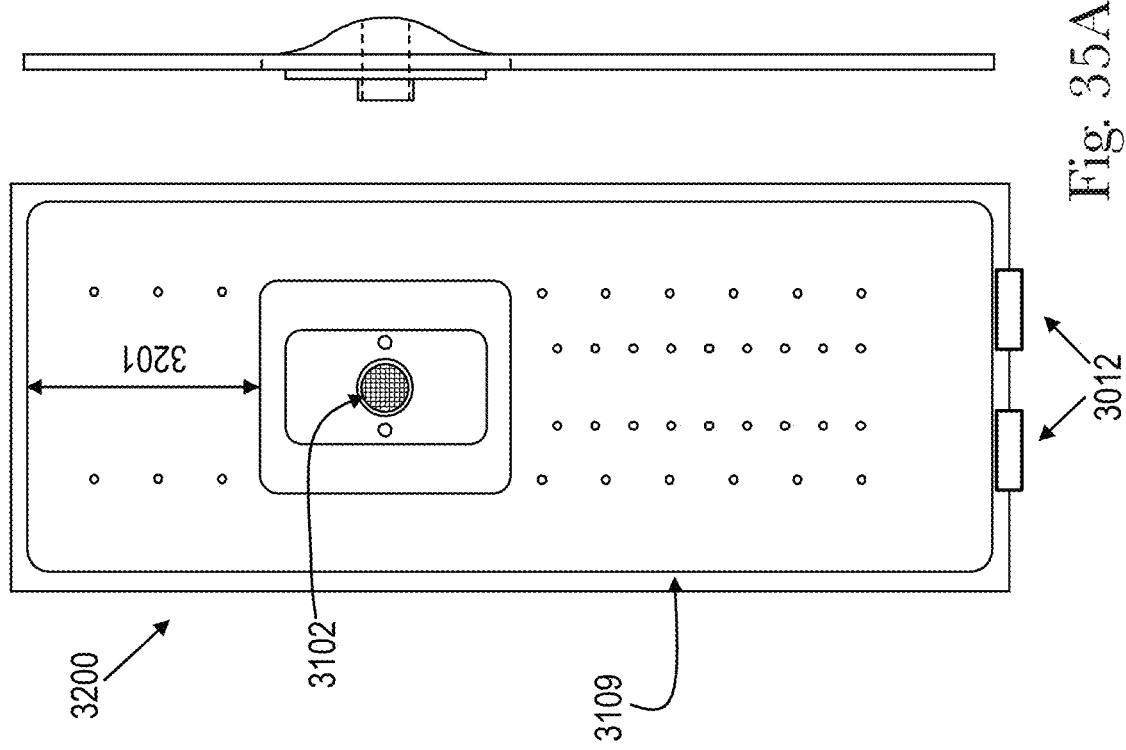
Fig. 35A
Fig. 35B

ABSORBENT ARTICLES WITH IMPROVED TOPSHEET DRYNESS

CROSS REFERENCE TO RELATED APPLICATIONS

This application is a continuation, under 35 U.S.C. § 120, of Patent Application No. PCT/CN2016/088095, filed on Jul. 1, 2016, which is herein incorporated by reference in its entirety.

FIELD

The present disclosure is generally related to absorbent articles and, is more specifically related to absorbent articles with improved topsheet dryness after one or more insults of bodily exudates.

BACKGROUND

Absorbent articles for personal hygiene, such as disposable diapers for infants and small children, training pants for toddlers, adult incontinence undergarments, and/or sanitary napkins are designed to absorb and contain bodily exudates, in particular large quantities of urine, runny BM, and/or menses (together the "fluids" or "fluid"). These absorbent articles may comprise several layers providing different functions, for example, a liquid permeable topsheet, a liquid impermeable backsheet, an absorbent core disposed between the topsheet and the backsheet, and an acquisition material disposed between the topsheet and the absorbent core, among other layers, if desired.

Fluid acquisition of absorbent articles has been researched for some time. Absorbent article manufactures typically try to improve fluid acquisition. Furthermore, once the fluid is absorbed through a topsheet into an absorbent core of an absorbent article, it is desirable to maintain that fluid within the absorbent core and not allow the fluid to migrate back up into the topsheet. This concept of migration back up into the topsheet is known in the art as rewet. Poor fluid acquisition and rewet, in some instances, may cause leakage and/or wet or damp topsheets after one or more insults of fluid. Fluid acquisition and rewet are further complicated when the topsheet is a three-dimensional, high basis weight material. Absorbent articles with three-dimensional, high basis weight materials, in some instances, increase fluid acquisition, but are typically worse for rewet compared with absorbent articles with traditional flat topsheets or apertured flat topsheets.

Current absorbent articles that provide three-dimensional, high basis weight materials struggle with fluid acquisition and rewet, thus leading to leakage and/or wet or damp topsheets. Thus, absorbent articles need to be improved to provide drier topsheets without compromising fluid acquisition performance and rewet.

SUMMARY

The absorbent articles of the present disclosure solve the problems of leakage and wet or damp topsheets and provide drier three-dimensional topsheets after fluid insults through improved fluid acquisition and reduced rewet. The three-dimensional topsheets may be apertured and may have large effective open areas to allow for faster fluid acquisition. Further, by providing three-dimensional topsheets, fluid may be maintained a distance away from a wearer's skin (e.g., in recesses of the three-dimensional topsheets) moments after a fluid insult, thereby leading to less fluid on the skin. Drier three-dimensional, high basis weight topsheets may be achieved by providing a Median Absorption Pressure gradient from the topsheet to the absorbent core or to a material under an acquisition layer. In general, the topsheet may have a low Median Absorption Pressure, while the absorbent core or a material (e.g., a layer of cross-linked cellulosic fibers) under the acquisition material may have the highest Median Absorption Pressure. The Median Absorption Pressure is measured by the Capillary Sorption Test herein. The Median Absorption Pressure is typically measured by an absorption curve and a desorption curve between 0% liquid saturation and 100% liquid saturation. Typically, the desorption curve of the topsheet should be equal or lower than the absorption curve of the absorbent core or the material under the acquisition material. Layers, such as one or more acquisition layers, intermediate the topsheet and the absorbent core or the material under the acquisition material may have a Median Absorption Pressure that is intermediate the low Median Absorption Pressure of the topsheet and the high Median Absorption Pressure of the absorbent core or the material under the acquisition material. Therefore, the particular acquisition material should have its absorption curve higher than or equal to the desorption curve of the topsheet and its desorption curve lower than or equal to the absorption curve of the absorbent core or the material under the acquisition material. Further, the particular acquisition materials of the present disclosure have a relatively high Median Absorption Pressure relative to the topsheet to dewater the three-dimensional topsheets disclosed herein. The three-dimensional topsheets disclosed herein have significant fluid holding capacity, owing to their three-dimensional structure, and provide immediate accessible volume for holding fluid upon fluid insults. This holding capacity is able to hold fluid until the fluid is drained from the topsheet by the acquisition material. The particular air-felt free cores or material under the acquisition material disclosed herein may contribute to reduced rewet by having the highest Median Absorption Pressure in the absorbent article. Thus, the combination of a three-dimensional, high basis weight topsheet, the acquisition materials described herein, and the absorbent cores or the materials under the acquisition materials described herein, and optional other layers, provides an absorbent article with improved topsheet dryness, caused by faster fluid acquisition speeds, reduced rewet, and a Median Absorption Pressure gradient that increases from the topsheet into the absorbent article.

The dense acquisition materials described herein may retain less liquid compared to convention acquisition materials (more open structure, less dense layers). Further, the three-dimensional topsheets may act a barrier to rewet owing to a hydrophobic layer in the topsheets. Essentially, the acquisition material acts as a barrier to fluid transfer (upwards) between the core and the topsheet and the topsheet acts as a barrier to fluid transfer (upwards) between the acquisition material and a wearer's skin.

The present disclosure is generally related, in part, to an absorbent article comprising a three-dimensional, liquid permeable topsheet. The liquid permeable topsheet comprises a first layer forming a portion of a wearer-facing surface of the absorbent article, wherein the first layer comprises a hydrophobic material. The topsheet comprises a second layer comprising a hydrophilic material, wherein the first layer is joined to the second layer. The topsheet comprises a plurality of recesses, a plurality of projections, and a plurality of land areas. The land areas surround at least a majority of the plurality of projections and a plurality of the recesses. The plurality of recesses, the plurality of projections, and the plurality of land areas, together form a first three-dimensional surface on a first side of the substrate and a second three-dimensional surface on a second side of the substrate. A majority of the projections have a z-directional height in the range of about 500 µm to about 4000 µm, according to the Projection Height Test. A majority of the recesses define an aperture at a location most distal from a top peak of an adjacent projection. The majority of the recesses have a z-directional height in the range of about 500 µm to about 2000 µm, according to the Recess Height Test. The topsheet has an overall z-directional height in the range of about 600 µm to about 6000 µm, according to the Overall Substrate Height Test. A portion of the projections and a portion of the recesses are formed by a portion of the first layer and a portion of the second layer. The apertures are formed through the first layer and through the second layer. The topsheet has a basis weight in the range of about 20 gsm to about 50 gsm, according to the Basis Weight Test. The absorbent article comprises a liquid impermeable backsheet, a material positioned at least partially intermediate the topsheet and the backsheet, and an acquisition material positioned at least partially intermediate the topsheet and the material. The topsheet comprises a first Median Absorption Pressure having a first value. The acquisition material comprises a Median Absorption Pressure having a second value. The material comprises a third Median Absorption Pressure having a third value. The second value is intermediate or equal to the first value and the third value.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting forms of the disclosure taken in conjunction with the accompanying drawings, wherein:

FIG. 17 is a front view of a portion of a three-dimensional, liquid permeable substrate, wearer-facing surface facing the viewer in accordance with the present disclosure;

FIG. 18 is a front perspective view of the portion of the three-dimensional, liquid permeable substrate of FIG. 17 in accordance with the present disclosure;

FIG. 19 is another front view of a portion of a three-dimensional, liquid permeable substrate, wearer-facing surface facing the viewer in accordance with the present disclosure;

FIG. 20 is a front perspective view of the portion of the liquid permeable substrate of FIG. 19 in accordance with the present disclosure;

FIG. 21 is a back view of a portion of a three-dimensional, liquid permeable substrate, wearer-facing surface facing the viewer in accordance with the present disclosure;

FIG. 22 is a back perspective view of the portion of the three-dimensional, liquid permeable substrate of FIG. 21 in accordance with the present disclosure;

FIG. 23 is another back view of a portion of a three-dimensional, liquid permeable substrate, wearer-facing surface facing the viewer in accordance with the present disclosure;

FIG. 24 is a back perspective view of the portion of the liquid permeable substrate of FIG. 23 in accordance with the present disclosure;

FIG. 35A illustrates a top plate assembly used in the Modified Fluid Acquisition Test; and FIG. 35B illustrates equipment used in the Modified Fluid Acquisition Test.

DETAILED DESCRIPTION

Figure 1:
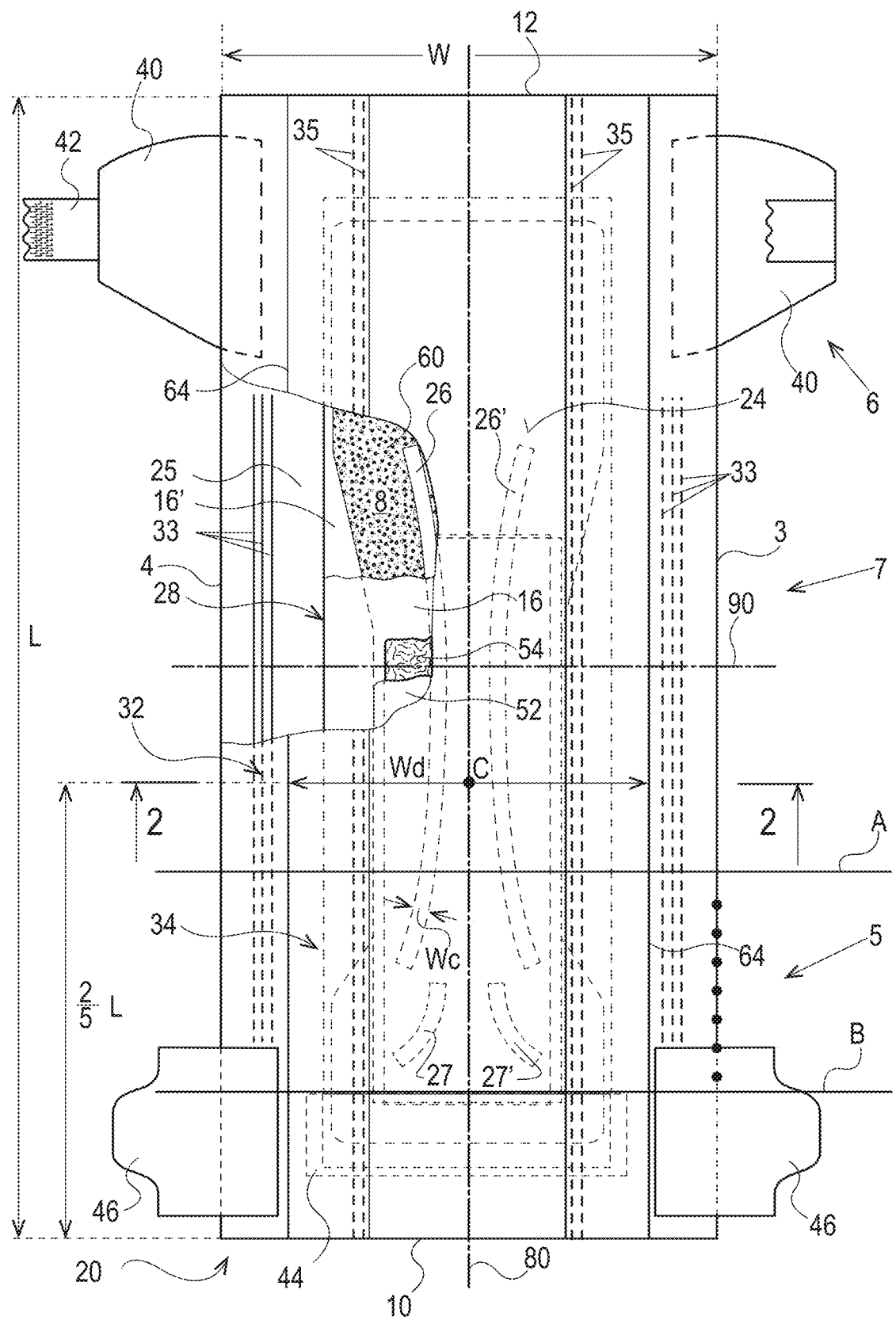
FIG. 1 is a top view of an absorbent article, wearer-facing surface facing the viewer, with some layers partially removed in accordance with the present disclosure.

Various non-limiting forms of the present disclosure will now be described to provide an overall understanding of the principles of the structure, function, manufacture, and use of the absorbent articles with improved topsheet dryness disclosed herein. One or more examples of these non-limiting embodiments are illustrated in the accompanying drawings. Those of ordinary skill in the art will understand that the absorbent articles with improved topsheet dryness described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Introduction

As used herein, the term "absorbent article" refers to disposable devices such as infant, child, or adult diapers, adult incontinence products, training pants, sanitary napkins, and the like which are placed against or in proximity to a body of a wearer to absorb and contain the various fluids discharged from the body. Typically, these absorbent articles comprise a topsheet, backsheet, an absorbent core, optionally an acquisition system and/or a distribution system (which may be comprised of one or several layers), and typically other components, with the absorbent core normally placed at least partially between the backsheet and the acquisition and/or distribution system. The absorbent articles comprising three-dimensional, high basis weight, liquid permeable substrates of the present disclosure will be further illustrated in the below description and in the Figures in the form of one or more components of taped diaper, such as a topsheet. Nothing in this description should be, however, considered limiting the scope of the claims. As such the present disclosure applies to any suitable form of absorbent articles (e.g., diapers, training pants, adult incontinence products, sanitary napkins).

As used herein, the term "nonwoven web" means a manufactured sheet, web, or batt of directionally or randomly orientated fibers, bonded by friction, and/or cohesion, and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers may have diameters ranging from less than about 0.001 mm to more than about 0.2 mm and may come in several different forms such as short fibers (known as staple, or chopped), continuous single fibers (filaments or monofilaments), untwisted bundles of continuous filaments (tow), and twisted bundles of continuous filaments (yam). Nonwoven webs may be formed by many processes such as meltblowing, spunbonding, solvent spinning, electrospinning, carding, and airlaying. The basis weight of nonwoven webs is usually expressed in grams per square meter ($g/m^2$ or gsm).

As used herein, the terms "joined", "bonded", or "attached" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "machine direction" or "MD" is the direction that is substantially parallel to the direction of travel of a substrate as it is made. The "cross direction" or "CD" is the direction substantially perpendicular to the MD and in the plane generally defined by the substrate.

As used herein, the term "hydrophilic", refers to a material having a contact angle less than or equal to 90° according to The American Chemical Society Publication "Contact Angle, Wettability, and Adhesion," edited by Robert F. Gould and copyrighted in 1964.

As used herein, the term "hydrophobic", refers to a material or layer having a contact angle greater than or equal to 90° according to The American Chemical Society Publication "Contact Angle, Wettability, and Adhesion," edited by Robert F. Gould and copyrighted in 1964.

General Description of the Absorbent Article

Figure 2:
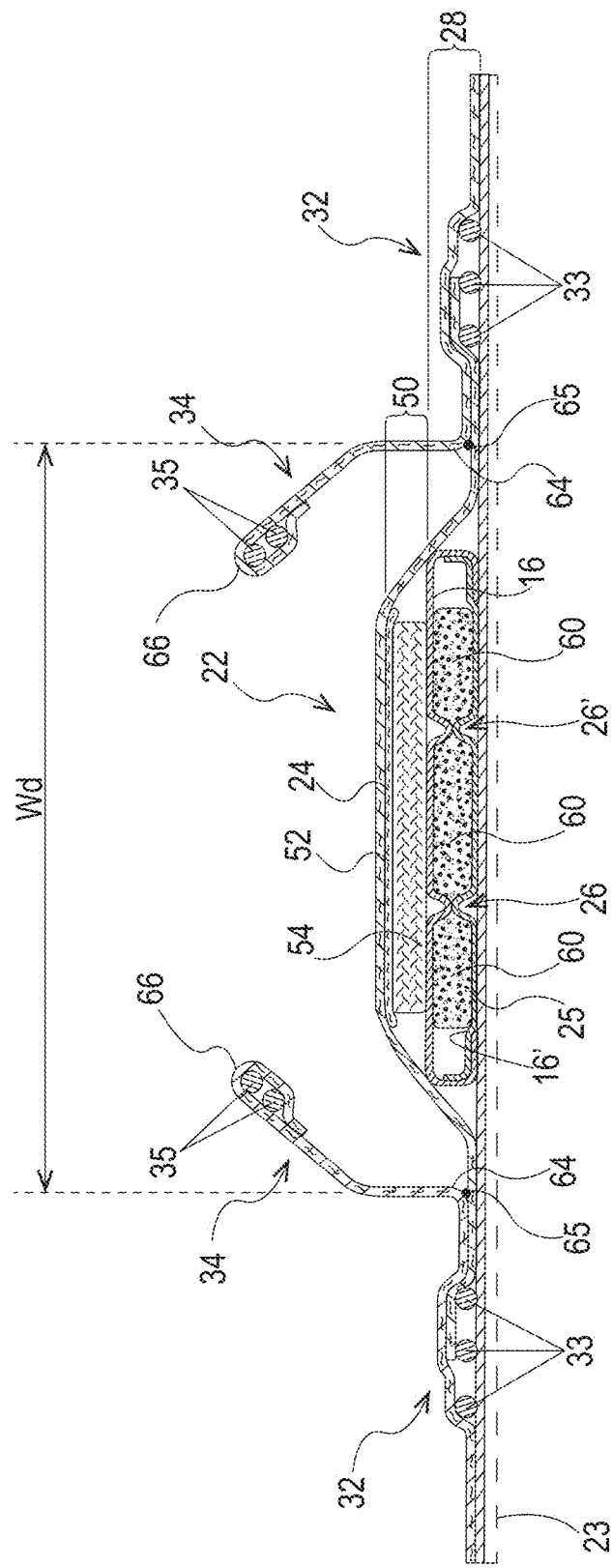
FIG. 2 is a cross-sectional view of the absorbent article taken about line 2-2 of FIG. 1 in accordance with the present disclosure.
Figure 3:
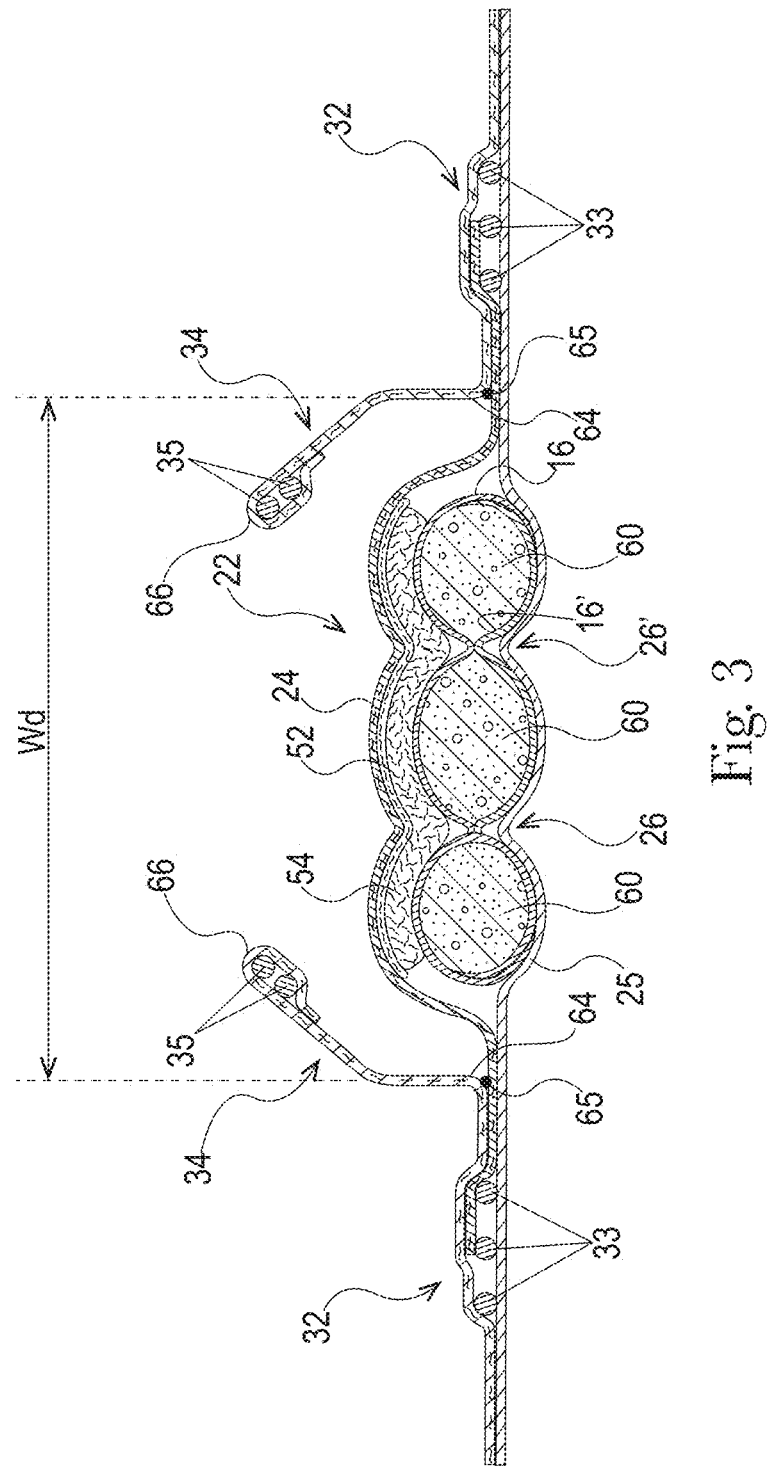
FIG. 3 is a cross-sectional view of the absorbent article taken about line 2-2 of FIG. 2 where the absorbent article has been loaded with fluid in accordance with the present disclosure.

An example absorbent article in the form of a diaper 20 is represented in FIGS. 1-3. FIG. 1 is a plan view of the example diaper 20, in a flat-out state, with portions of the structure being cut-away to more clearly show the construction of the diaper 20. The wearer-facing surface of the diaper 20 of FIG. 1 is facing the viewer. This diaper 20 is shown for illustration purpose only as the three-dimensional substrates of the present disclosure may be used as one or more components of an absorbent article, such as a topsheet.

The absorbent article 20 may comprise a liquid permeable topsheet 24, a liquid impermeable backsheet 25, an absorbent core 28 positioned at least partially intermediate the topsheet 24 and the backsheet 25, and barrier leg cuffs 34. The absorbent article may also comprise an acquisition and/or distribution system ("ADS") 50, which in the example represented comprises a distribution layer 54 and an acquisition layer 52, which will be further detailed below. This distribution layer 54 and the absorbent core 28 may be referred to as a "material" herein and in the claims. The ADS, in some instances, may only comprise one or more acquisition layers. The absorbent article may also comprise elasticized gasketing cuffs 32 comprising elastics 33 joined to a chassis of the absorbent article, typically via the topsheet and/or backsheet, and substantially planar with the chassis of the diaper.

The figures also show typical taped diaper components such as a fastening system comprising tabs 42 attached towards the rear edge of the article and cooperating with a landing zone 44 on the front of the absorbent article. The absorbent article may also comprise other typical elements, which are not represented, such as a rear elastic waist feature, a front elastic waist feature, transverse barrier cuff(s), and/or a lotion application, for example.

The absorbent article 20 comprises a front waist edge 10, a rear waist edge 12 longitudinally opposing the front waist edge 10, a first side edge 3, and a second side edge 4 laterally opposing the first side edge 3. The front waist edge 10 is the edge of the absorbent article which is intended to be placed towards the front of the user when worn, and the rear waist edge 12 is the opposite edge. The absorbent article 20 may have a longitudinal axis 80 extending from the lateral midpoint of the front waist edge 10 to a lateral midpoint of the rear waist edge 12 of the article and dividing the article in two substantially symmetrical halves relative to the longitudinal axis 80, with the absorbent article placed flat and viewed from above as in FIG. 1. The absorbent article may also have a lateral axis 90 extending from the longitudinal midpoint of the first side edge 3 to the longitudinal midpoint of the second side edge 4. The length, L, of the article may be measured along the longitudinal axis 80 from the front waist edge 10 to the rear waist edge 12. The width, W, of the article may be measured along the lateral axis 90 from the first side edge 3 to the second side edge 4. The article may comprise a crotch point C defined herein as the point placed on the longitudinal axis at a distance of two fifth (⅖) of L starting from the front edge 10 of the article 20. The article may comprise a front waist region 5, a rear waist region 6, and a crotch region 7. The front waist region 5, the rear waist region 6, and the crotch region 7 each define ⅓ of the longitudinal length, L, of the absorbent article.

The topsheet 24, the backsheet 25, the absorbent core 28, and the other article components may be assembled in a variety of configurations, in particular by gluing or heat embossing, for example. Example absorbent article configurations are described generally in U.S. Pat. Nos. 3,860,003, 5,221,274, 5,554,145, 5,569,234, 5,580,411, and 6,004,306.

The absorbent core 28 may comprise an absorbent material comprising at least 80%, at least 90%, at least 95%, or at least 99% by weight of absorbent material and a core wrap enclosing the superabsorbent polymers. The core wrap may typically comprise two materials, substrates, or nonwoven materials 16 and 16' for the top side and bottom side of the core. The core may comprises one or more channels, represented in FIG. 1 as the four channels 26, 26' and 27, 27'. The channels 26, 26', 27, and 27' are optional features. Instead, the core may not have any channels, may only have the channels 26 and 26', or may have any suitable number of channels.

These and other components of the example absorbent article will now be discussed in more details.

Topsheet

In the present disclosure, the topsheet (the portion of the absorbent article that contacts the wearer's skin and receives the fluids) may be formed of a portion of, or all of, one or more of the three-dimensional substrates described herein and/or have one or more three-dimensional substrates positioned thereon and/or joined thereto, so that the three-dimensional substrate(s) contact(s) the wearer's skin. Other portions of the topsheet (other than the three-dimensional substrates) may also contact the wearer's skin. The three-dimensional substrates may be positioned as a strip or a patch on top of the typical topsheet 24, as is described herein. The three-dimensional substrates will be described in further detail below.

The topsheet 24 may be joined to the backsheet 25, the core 28 and/or any other layers as is known to those of skill in the art. Usually, the topsheet 24 and the backsheet 25 are joined directly to each other in some locations (e.g., on or close to the periphery of the absorbent article) and are indirectly joined together in other locations by directly joining them to one or more other elements of the article 20.

Any portion of the topsheet 24 may be coated with a lotion and/or a skin care composition as is generally disclosed in the art. The topsheet 24 may also comprise or be treated with antibacterial agents, some examples of which are disclosed in PCT Publication WO95/24173.

The topsheet 24 may be apertured as discussed below.

Backsheet

The backsheet 25 is generally that portion of the absorbent article 20 positioned adjacent the garment-facing surface of the absorbent core 28 and which prevents, or at least inhibits, the fluids absorbed and contained therein from soiling articles such as bedsheets and undergarments. The backsheet 25 is typically impermeable, or at least substantially impermeable, to the fluids. The backsheet may, for example, be or comprise a thin plastic film such as a thermoplastic film having a thickness of about 0.012 mm to about 0.051 mm. Example backsheet films include those manufactured by Tredegar Corporation, based in Richmond, Va., and sold under the trade name CPC2 film. Other suitable backsheet materials may include breathable materials which permit vapors to escape from the absorbent article 20 while still preventing, or at least inhibiting, fluids from passing through the backsheet 25. Example breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097.

The backsheet 25 may be joined to the topsheet 24, the absorbent core 28, and/or any other element of the absorbent article 20 by any attachment methods known to those of skill in the art.

Outer Cover

An outer cover 23 may cover at least a portion of, or all of, the backsheet 25 to form a soft garment-facing surface of the absorbent article. The outer cover 23 may be formed of one or more nonwoven materials. The outer cover 23 is illustrated in dash in FIG. 2, as an example. The outer cover 23 may be joined to at least a portion of the backsheet 25 through mechanical bonding, adhesive bonding, or other suitable methods of attachment. The outer cover, or portions thereof, may be an embossed or three-dimensional material. In some instances, whether planar or three-dimensional, the outer cover, or portions thereof, may be apertured. Example suitable outer covers are disclosed in U.S. Pat. No. 9,408,761, issued on Aug. 9, 2016, to Xu et al. and U.S. Patent Application Pub. No. 2017/0165127, published on Jun. 15, 2017, to Xu et al. The outer covers may have a bonding pattern as disclosed in the two patent applications above. The outer covers may have a basis weight in the range of about 18 gsm to about 30 gsm, such as 25 gsm or 22 gsm, according to the Basis Weight Test, for example. The outer covers may comprise spunbond nonwovens or air through carded nonwovens, for example.

Absorbent Core

As used herein, the term "absorbent core" refers to the component of the absorbent article having the most absorbent capacity and comprising an absorbent material and a core wrap or core bag enclosing the absorbent material. The absorbent core may be referred to as a "material" in the claims. The term "absorbent core" does not include the acquisition and/or distribution system or any other components of the article which are not either integral part of the core wrap or core bag or placed within the core wrap or core bag. The absorbent core may comprise, consist essentially of, or consist of, a core wrap, an absorbent material (e.g., superabsorbent polymers) as discussed, and glue.

The absorbent core 28 may comprise an absorbent material with a high amount of superabsorbent polymers (herein abbreviated as "SAP") enclosed within the core wrap. The SAP content may represent 70%-100% or at least 70%, 75%, 80%, 85%, 90%, 95%, 99%, or 100%, by weight of the absorbent material, contained in the core wrap. The core wrap is not considered as absorbent material for the purpose of assessing the percentage of SAP in the absorbent core. The core may also contain airfelt or cellulosic fibers with or without SAP.

By "absorbent material" it is meant a material which has some absorbency property or liquid retaining properties, such as SAP, cellulosic fibers as well as synthetic fibers. Typically, glues used in making absorbent cores have no or little absorbency properties and are not considered as absorbent material. The SAP content may be higher than 80%, for example at least 85%, at least 90%, at least 95%, at least 99%, and even up to and including 100% of the weight of the absorbent material contained within the core wrap. This provides a relatively thin core compared to a conventional core typically comprising between 40-60% SAP and high content of cellulose fibers. The conventional cores are also within the scope of the present disclosure. The absorbent material may in particular comprises less than 15% weight percent or less than 10% weight percent of natural, cellulosic, or synthetic fibers, less than 5% weight percent, less than 3% weight percent, less than 2% weight percent, less than 1% weight percent, or may even be substantially free of natural, cellulosic, and/or synthetic fibers.

Figure 4:
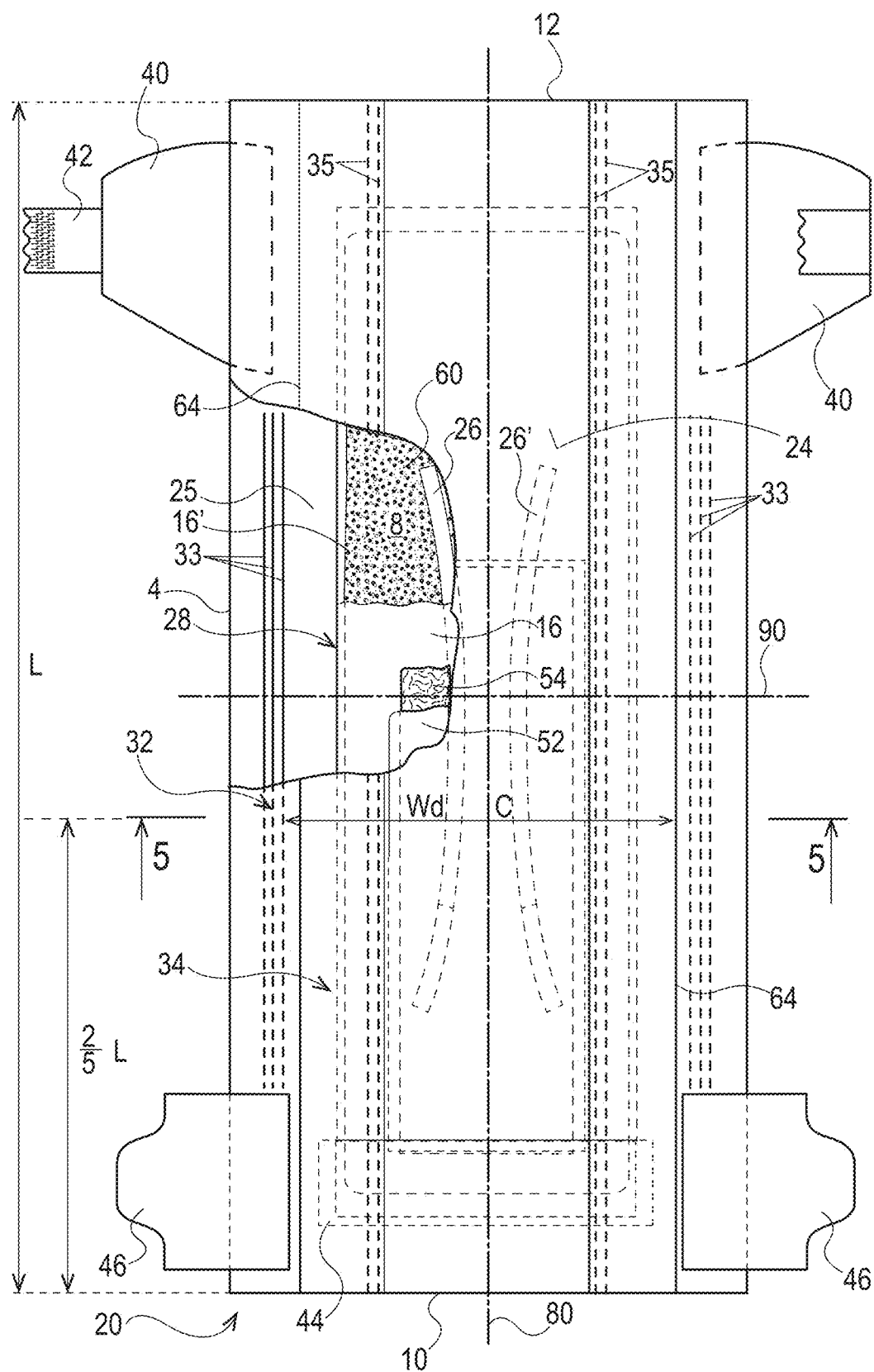
FIG. 4 is a top view of another absorbent article, wearer-facing surface facing the viewer, with some layers partially removed in accordance with the present disclosure.
Figure 5:
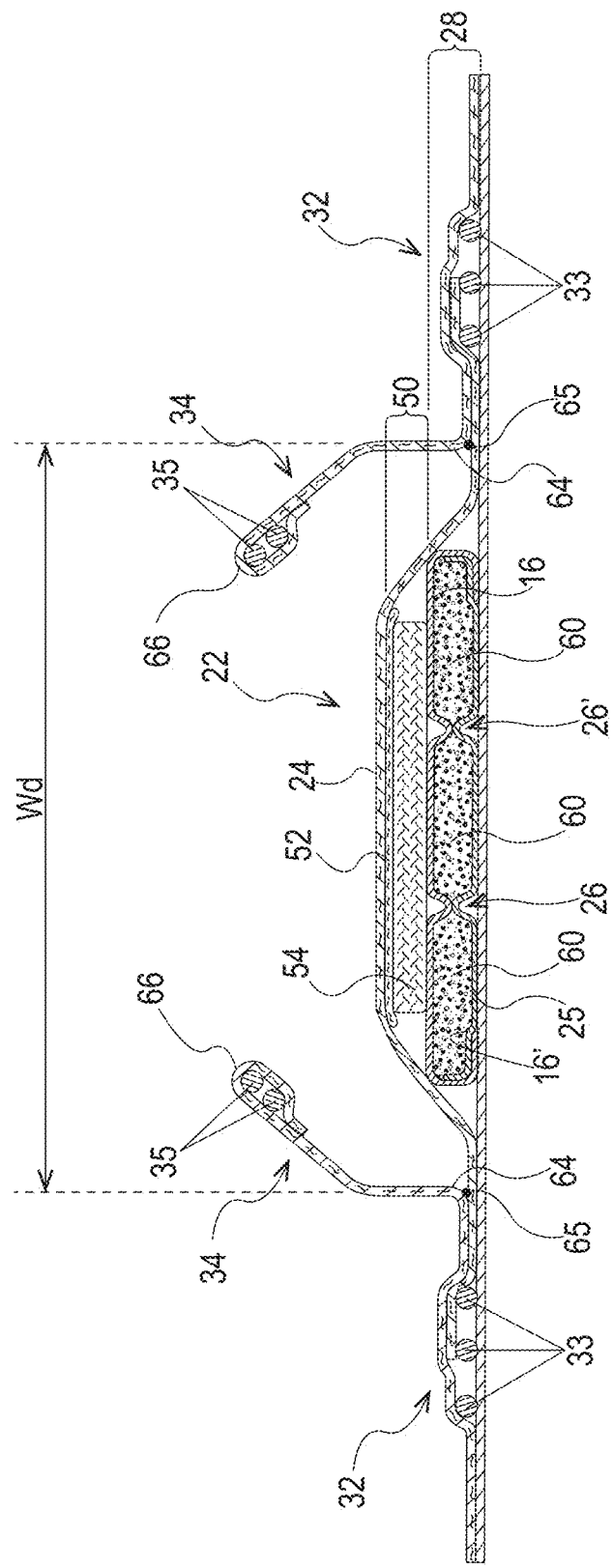
FIG. 5 is a cross-sectional view of the absorbent article taken about line 5-5 of FIG. 4 in accordance with the present disclosure.
Figure 6:
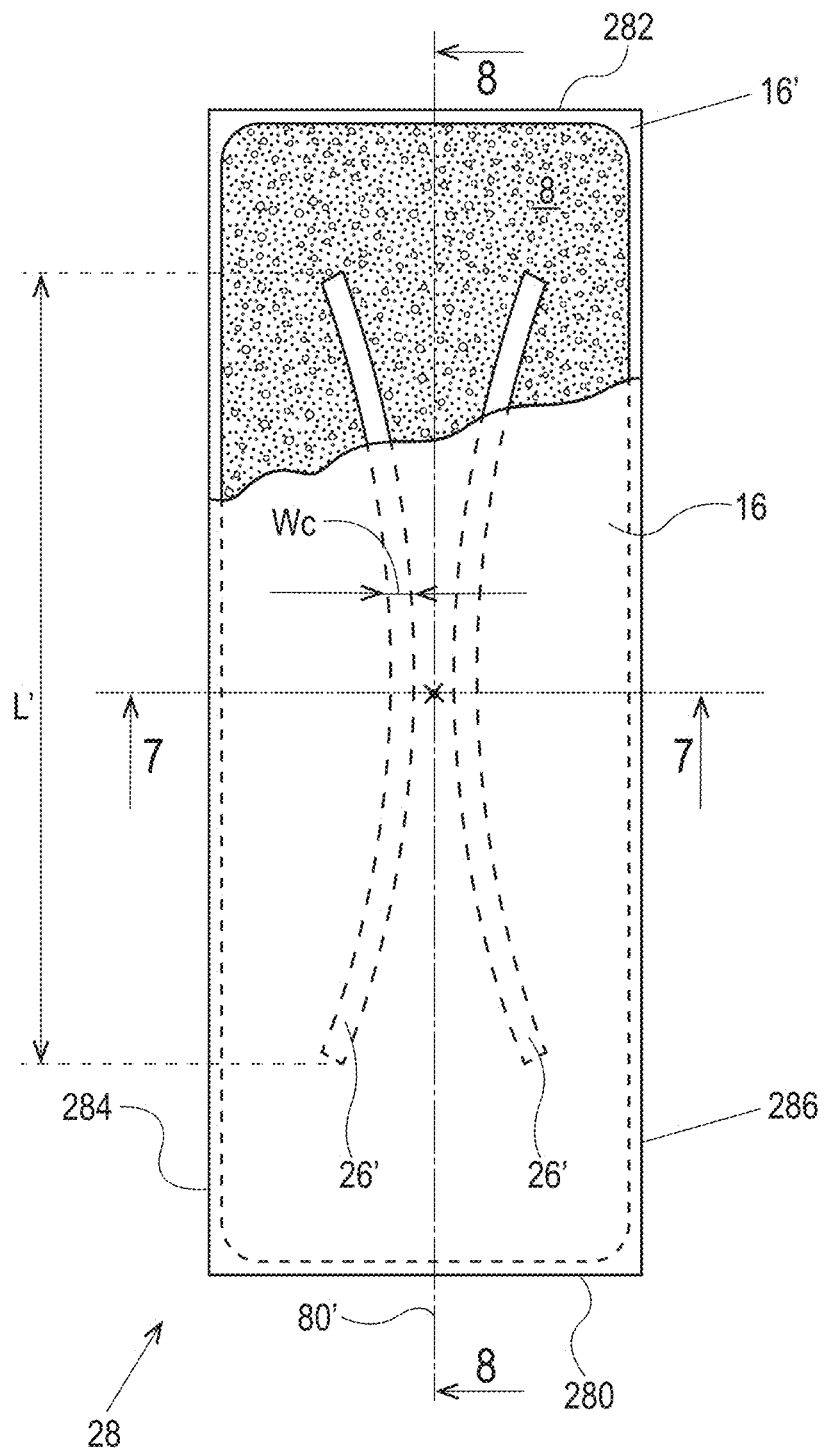
FIG. 6 is a top view of an absorbent core of the absorbent article of FIG. 4 with some layers partially removed in accordance the present disclosure.
Figure 7:
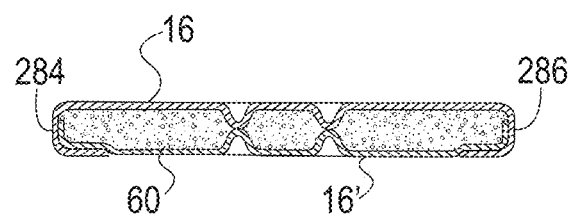
FIG. 7 is a cross-sectional view of the absorbent core taken about line 7-7 of FIG. 6 in accordance with the present disclosure.
Figure 8:
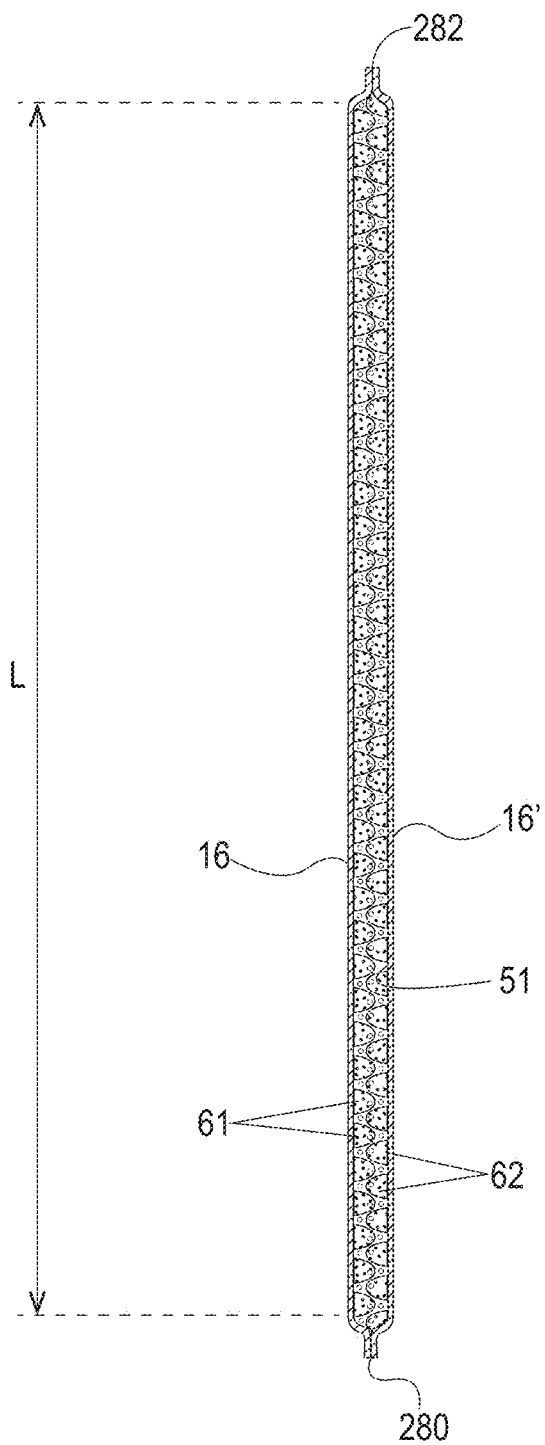
FIG. 8 is a cross-sectional view of the absorbent core taken about line 8-8 of FIG. 6 in accordance with the present disclosure.

The example absorbent core 28 of the absorbent article 20 of FIGS. 4-5 is shown in isolation in FIGS. 6-8. The absorbent core 28 may comprises a front side 280, a rear side 282, and two longitudinal sides 284, 286 joining the front side 280 and the rear side 282. The absorbent core 28 may also comprise a generally planar top side and a generally planar bottom side. The front side 280 of the core is the side of the core intended to be placed towards the front waist edge 10 of the absorbent article. The core 28 may have a longitudinal axis 80' corresponding substantially to the longitudinal axis 80 of the absorbent article 20, as seen from the top in a planar view as in FIG. 1. The absorbent material may be distributed in higher amount towards the front side 280 than towards the rear side 282 as more absorbency may be required at the front in particular absorbent articles. The front and rear sides 280 and 282 of the core may be shorter than the longitudinal sides 284 and 286 of the core. The core wrap may be formed by two nonwoven materials, substrates, laminates, or other materials, 16, 16' which may be at least partially sealed along the sides 284, 286 of the absorbent core 28. The core wrap may be at least partially sealed along its front side 280, rear side 282, and two longitudinal sides 284, 286 so that substantially no absorbent material leaks out of the absorbent core wrap. The first material, substrate, or nonwoven 16 may at least partially surround the second material, substrate, or nonwoven 16' to form the core wrap, as illustrated in FIG. 7. The first material 16 may surround a portion of the second material 16' proximate to the first and second side edges 284 and 286 to form what is known as a C-wrap.

The absorbent core may comprise adhesive, for example, to help immobilizing the SAP within the core wrap and/or to ensure integrity of the core wrap, in particular when the core wrap is made of two or more substrates. The adhesive may be a hot melt adhesive, supplied, by H. B. Fuller, for example. The core wrap may extend to a larger area than strictly needed for containing the absorbent material within.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be a continuous layer present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two absorbent layers having discontinuous absorbent material application patterns, wherein the resulting layer is substantially continuously distributed across the absorbent particulate polymer material area, as disclosed in U.S. Pat. Appl. Pub. No. 2008/0312622A1 (Hundorf), for example. The absorbent core 28 may comprise a first absorbent layer and a second absorbent layer. The first absorbent layer may comprise the first material 16 and a first layer 61 of absorbent material, which may be 100% or less of SAP. The second absorbent layer may comprise the second material 16' and a second layer 62 of absorbent material, which may also be 100% or less of SAP. The absorbent core 28 may also comprise a fibrous thermoplastic adhesive material 51 at least partially bonding each layer of absorbent material 61, 62 to its respective material 16 or 16'. This is illustrated in FIGS. 7-8, as an example, where the first and second SAP layers have been applied as transversal stripes or "land areas" having the same width as the desired absorbent material deposition area on their respective substrate before being combined. The stripes may comprise different amounts of absorbent material (SAP) to provide a profiled basis weight along the longitudinal axis of the core 80. The first material 16 and the second material 16' may form the core wrap.

The fibrous thermoplastic adhesive material 51 may be at least partially in contact with the absorbent material 61, 62 in the land areas and at least partially in contact with the materials 16 and 16' in the junction areas. This imparts an essentially three-dimensional structure to the fibrous layer of thermoplastic adhesive material 51, which in itself is essentially a two-dimensional structure of relatively small thickness, as compared to the dimension in length and width directions. Thereby, the fibrous thermoplastic adhesive material may provide cavities to cover the absorbent material in the land areas, and thereby immobilizes this absorbent material, which may be 100% or less of SAP.

The thermoplastic adhesive used for the fibrous layer may have elastomeric properties, such that the web formed by the fibers on the SAP layer is able to be stretched as the SAP swell. Elastomeric, hot-melt adhesives of these types are described in more detail in U.S. Pat. No. 4,731,066 issued to Korpman on Mar. 15, 1988. The thermoplastic adhesive material may be applied as fibers.

Superabsorbent Polymer (SAP)

"Superabsorbent polymers" ("SAP"), as used herein, refer to absorbent materials which are cross-linked polymeric materials that can absorb at least 10 times their weight of an aqueous 0.9% saline solution as measured using the Centrifuge Retention Capacity (CRC) test (EDANA method WSP 241.2-05E). The SAP used may have a CRC value of more than 20 g/g, more than 24 g/g, from 20 to 50 g/g, from 20 to 40 g/g, or from 24 to 30 g/g, specifically reciting all 0.1 g/g increments within the above-specified ranges and any ranges created therein or thereby. The SAP useful with the present disclosure may include a variety of water-insoluble, but water-swellable polymers capable of absorbing large quantities of fluids.

The superabsorbent polymer may be in particulate form so as to be flowable in the dry state. Particulate absorbent polymer materials may be made of poly(meth)acrylic acid polymers. However, starch-based particulate absorbent polymer material may also be used, as well as poly acrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

The SAP may be of numerous shapes. The term "particles" refers to granules, fibers, flakes, spheres, powders, platelets and other shapes and forms known to persons skilled in the art of superabsorbent polymer particles. The SAP particles may be in the shape of fibers, i.e., elongated, acicular superabsorbent polymer particles. The fibers may also be in the form of a long filament that may be woven. SAP may be spherical-like particles. The absorbent core may comprise one or more types of SAP.

For most absorbent articles, liquid discharges from a wearer occur predominately in the front half of the absorbent article, in particular for a diaper. The front half of the article (as defined by the region between the front edge and a transversal line placed at a distance of half L from the front waist edge 10 or rear waist edge 12 may therefore may comprise most of the absorbent capacity of the core. Thus, at least 60% of the SAP, or at least 65%, 70%, 75%, 80%, or 85% of the SAP may be present in the front half of the absorbent article, while the remaining SAP may be disposed in the rear half of the absorbent article. Alternatively, the SAP distribution may be uniform through the core or may have other suitable distributions.

The total amount of SAP present in the absorbent core may also vary according to expected user. Diapers for newborns may require less SAP than infant, child, or adult incontinence diapers. The amount of SAP in the core may be about 5 to 60 g or from 5 to 50 g, specifically reciting all 0.1 increments within the specified ranges and any ranged formed therein or thereby. The average SAP basis weight within the (or "at least one", if several are present) deposition area 8 of the SAP may be at least 50, 100, 200, 300, 400, 500 or more g/m². The areas of the channels (e.g., 26, 26', 27, 27') present in the absorbent material deposition area 8 are deduced from the absorbent material deposition area to calculate this average basis weight.

Core Wrap

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, as illustrated, for example, in FIGS. 2 and 7, the longitudinal and/or transversal edges of one of the substrates are folded over the other substrate to form flaps. These flaps are then bonded to the external surface of the other substrate, typically by gluing.

The core wrap may be formed by any materials suitable for receiving and containing the absorbent material. Typical substrate materials used in the production of conventional cores may be used, in particular paper, tissues, films, wovens or nonwovens, or laminates or composites of any of these.

The substrates may also be air-permeable (in addition to being liquid or fluid permeable). Films useful herein may therefore comprise micro-pores.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

If the core wrap is formed by two substrates 16, 16', four seals may be used to enclose the absorbent material 60 within the core wrap. For example, a first substrate 16 may be placed on one side of the core (the top side as represented in the Figures) and extend around the core's longitudinal edges to at least partially wrap the opposed bottom side of the core. The second substrate 16' may be present between the wrapped flaps of the first substrate 16 and the absorbent material 60. The flaps of the first substrate 16 may be glued to the second substrate 16' to provide a strong seal. This so called C-wrap construction may provide benefits such as improved resistance to bursting in a wet loaded state compared to a sandwich seal. The front side and rear side of the core wrap may then also be sealed by gluing the first substrate and second substrate to another to provide complete encapsulation of the absorbent material across the whole of the periphery of the core. For the front side and rear side of the core, the first and second substrates may extend and may be joined together in a substantially planar direction, forming for these edges a so-called sandwich construction. In the so-called sandwich construction, the first and second substrates may also extend outwardly on all sides of the core and be sealed flat, or substantially flat, along the whole or parts of the periphery of the core typically by gluing and/or heat/pressure bonding. In an example, neither the first nor the second substrates need to be shaped, so that they may be rectangularly cut for ease of production but other shapes are within the scope of the present disclosure.

The core wrap may also be formed by a single substrate which may enclose as in a parcel wrap the absorbent material and be sealed along the front side and rear side of the core and one longitudinal seal.

SAP Deposition Area

The absorbent material deposition area 8 may be defined by the periphery of the layer formed by the absorbent material 60 within the core wrap, as seen from the top side of the absorbent core. The absorbent material deposition area 8 may have various shapes, in particular, a so-called "dog bone" or "hour-glass" shape, which shows a tapering along its width towards the middle or "crotch" region of the core. In this way, the absorbent material deposition area 8 may have a relatively narrow width in an area of the core intended to be placed in the crotch region of the absorbent article, as illustrated in FIG. 1. This may provide better wearing comfort. The absorbent material deposition area 8 may also be generally rectangular, for example as shown in FIGS. 4-6, but other deposition areas, such as a rectangular, "T," "Y," "sand-hour," or "dog-bone" shapes are also within the scope of the present disclosure. The absorbent material may be deposited using any suitable techniques, which may allow relatively precise deposition of SAP at relatively high speed.

Channels

The absorbent material deposition area 8 may comprise at least one channel 26, which is at least partially oriented in the longitudinal direction of the article 80 (i.e., has a longitudinal vector component). Other channels may be at least partially oriented in the lateral direction (i.e., has a lateral vector component) or in any other direction. In the following, the plural form "channels" will be used to mean "at least one channel". The channels may have a length L' projected on the longitudinal axis 80 of the article that is at least 10%, at least 30%, at least 50%, at least 60%, at least 75% of the length L of the article. The channels may be formed in various ways. For example, the channels may be formed by zones within the absorbent material deposition area 8 which may be substantially free of, or free of, absorbent material, in particular SAP. In addition or alternatively, the channel(s) may also be formed by continuously or discontinuously bonding the top side of the core wrap to the bottom side of the core wrap through the absorbent material deposition area 8. The channels may be continuous but it is also envisioned that the channels may be intermittent. The acquisition-distribution system or layer 50, or another layer of the article, may also comprise channels, which may or not correspond to the channels of the absorbent core.

In some instances, the channels may be present at least at the same longitudinal level as the crotch point C or the lateral axis 60 in the absorbent article, as represented in FIG. 1 with the two longitudinally extending channels 26, 26'. The channels may also extend from the crotch region 7 or may be present in the front waist region 5 and/or in the rear waist region 6 of the article.

The absorbent core 28 may also comprise more than two channels, for example, at least 3, at least 4, at least 5, or at least 6 or more. Shorter channels may also be present, for example in the rear waist region 6 or the front waist region 5 of the core as represented by the pair of channels 27, 27' in FIG. 1 towards the front of the article. The channels may comprise one or more pairs of channels symmetrically arranged, or otherwise arranged relative to the longitudinal axis 80.

The channels may be particularly useful in the absorbent core when the absorbent material deposition area is rectangular, as the channels may improve the flexibility of the core to an extent that there is less advantage in using a non-rectangular (shaped) core. Of course channels may also be present in a layer of SAP having a shaped deposition area.

The channels may be completely oriented longitudinally and parallel to the longitudinal axis or completely oriented transversely and parallel to the lateral axis, but also may have at least portions that are curved.

In order to reduce the risk of fluid leakages, the longitudinal main channels may not extend up to any of the edges of the absorbent material deposition area 8, and may therefore be fully encompassed within the absorbent material deposition area 8 of the core. The smallest distance between a channel and the closest edge of the absorbent material deposition area 8 may be at least 5 mm.

The channels may have a width Wc along at least part of their length which is at least 2 mm, at least 3 mm, at least 4 mm, up to for example 20 mm, 16 mm, or 12 mm, for example. The width of the channel(s) may be constant through substantially the whole length of the channel or may vary along its length. When the channels are formed by absorbent material-free zone within the absorbent material deposition area 8, the width of the channels is considered to be the width of the material free zone, disregarding the possible presence of the core wrap within the channels. If the channels are not formed by absorbent material free zones, for example mainly though bonding of the core wrap through the absorbent material zone, the width of the channels is the width of this bonding.

At least some or all of the channels may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the upper side and lower side of the core wrap (e.g., the first substrate 16 and the second substrate 16') and/or the topsheet 24 to the backsheet 25 together through the channels. Typically, an adhesive may be used to bond both sides of the core wrap or the topsheet and the backsheet through the channels, but it is possible to bond via other known processes, such as pressure bonding, ultrasonic bonding, heat bonding, or combination thereof. The core wrap or the topsheet 24 and the backsheet 25 may be continuously bonded or intermittently bonded along the channels. The channels may advantageously remain or become visible at least through the topsheet and/or backsheet when the absorbent article is fully loaded with a fluid. This may be obtained by making the channels substantially free of SAP, so they will not swell, and sufficiently large so that they will not close when wet. Furthermore, bonding the core wrap to itself or the topsheet to the backsheet through the channels may be advantageous.

In some instances, channels may be embossed into the absorbent material and/or the core bag. In such an instance, these channels will be densified regions of the absorbent material and/or the core bag.

Barrier Leg Cuffs

The absorbent article may comprise a pair of barrier leg cuffs 34. Each barrier leg cuff may be formed by a piece of material which is bonded to the article so it may extend upwards from a wearer-facing surface of the absorbent article and provide improved containment of fluids and other body exudates approximately at the junction of the torso and legs of the wearer. The barrier leg cuffs are delimited by a proximal edge 64 joined directly or indirectly to the topsheet 24 and/or the backsheet 25 and a free terminal edge 66, which is intended to contact and form a seal with the wearer's skin. The barrier leg cuffs 34 extend at least partially between the front waist edge 10 and the rear waist edge 12 of the absorbent article on opposite sides of the longitudinal axis 80 and are at least present at the level of the crotch point (C) or crotch region. The barrier leg cuffs may be joined at the proximal edge 64 with the chassis of the article by a bond 65 which may be made by gluing, fusion bonding, or a combination of other suitable bonding processes. The bond 65 at the proximal edge 64 may be continuous or intermittent. The bond 65 closest to the raised section of the leg cuffs delimits the proximal edge 64 of the standing up section of the leg cuffs.

The barrier leg cuffs may be integral with the topsheet 24 or the backsheet 25 or may be a separate material joined to the article's chassis. Each barrier leg cuff 34 may comprise one, two or more elastic strings 35 close to the free terminal edge 66 to provide a better seal.

In addition to the barrier leg cuffs 34, the article may comprise gasketing cuffs 32, which are joined to the chassis of the absorbent article, in particular to the topsheet 24 and/or the backsheet 25 and are placed externally relative to the barrier leg cuffs. The gasketing cuffs 32 may provide a better seal around the thighs of the wearer. Each gasketing leg cuff may comprise one or more elastic strings or elastic elements 33 in the chassis of the absorbent article between the topsheet 24 and backsheet 25 in the area of the leg openings. All, or a portion of, the barrier leg cuffs and/or gasketing cuffs may be treated with a lotion or another skin care composition.

Acquisition-Distribution System

The absorbent articles of the present disclosure may comprise an acquisition-distribution layer or system 50 ("ADS"). One function of the ADS is to quickly acquire one or more of the fluids and distribute them to the absorbent core in an efficient manner. The ADS may comprise one, two or more layers, which may form a unitary layer or may remain as discrete layers which may be attached to each other. In an example, the ADS may comprise two layers: a distribution layer 54 and an acquisition layer 52 disposed between the absorbent core and the topsheet, but the present disclosure is not so limited.

In an example, only one layer of the ADS may be provided, such as the distribution layer only or the acquisition layer only. When one of the three-dimensional, liquid permeable substrates of the present disclosure is used as a portion of, or all of, a topsheet, or positioned on a topsheet, dryness performance of the three-dimensional liquid permeable substrates may be improved if only one or two layers of the ADS are present. This is owing to the fact that fluids are easily able to wick through the liquid permeable substrates into one or two layers of the ADS and then into the absorbent core.

Distribution Layer

The distribution layer or "material" of the ADS may comprise at least 50% by weight of cross-linked cellulose fibers. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf). The cross-linked cellulosic fibers provide higher resilience and therefore higher resistance to the first absorbent layer against the compression in the product packaging or in use conditions, e.g., under wearer weight. This may provide the core with a higher void volume, permeability, and liquid absorption, and hence reduced leakage and improved dryness.

The distribution layer comprising the cross-linked cellulose fibers of the present disclosure may comprise other fibers, but this layer may advantageously comprise at least 50%, or 60%, or 70%, or 80%, or 90%, or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In still another example, the layer may comprise about 68% by weight chemically cross-linked cellulose fibers, about 16% by weight untreated pulp fibers, and about 16% by weight PET fibers. In yet another example, the layer of cross-linked cellulose fibers may comprise from about 90 to about 100% by weight chemically cross-linked cellulose fibers. This distribution layer may also comprise other materials, such as nonwoven materials.

Acquisition Layer

The ADS 50 may comprise an acquisition layer 52. The acquisition layer 52 may be disposed between the distribution layer 54 and the topsheet 24 or between the topsheet 24 and the absorbent core 28 if a distribution layer is not provided. The acquisition layer 52 may be or may comprise a nonwoven material, such a carded resin bonded nonwoven material, a carded air-through bonded nonwoven material, or a spunlace material, for example. The acquisition layer 52 may have a basis weight in the range of about 8 gsm to about 100 gsm, about 20 gsm to about 100 gsm, about 20 gsm to about 80 gsm, about 20 gsm to about 65 gsm, about 35 gsm to about 55 gsm, about 40 gsm to about 50 gsm, about 40 gsm to about 45 gsm, about 42 gsm, about 43 gsm, or about 44 gsm, for example, according to the Basis Weight Test herein, specifically reciting all 0.1 gsm increments within the specified ranges and all ranges formed therein or thereby. The acquisition layer may be formed of one or more layers. If more than one layer is provided, the basis weight ranges provided above are for the total basis weight of the layers together. The acquisition layer 52 may comprise about 0% to about 60%, about 20% to about 50%, about 20% to about 40%, about 25% to about 35%, about 50%, or about 30% PET solid round, shaped, and/or trilobal fibers that have a denier of about 3 to about 5, preferably about 4, and about 40% to about 100%, about 30% to about 90%, about 50% to about 80%, about 60% to about 80%, about 50%, about 60%, or about 70% PET solid round, shaped, and/or trilobal fibers that have a denier of about 0.5 to about 3, preferably about 1.5. All 0.1% increments within the above-specified ranges, and all ranges formed therein or thereby, are specifically disclosed, but not written out for brevity. Denier is defined as the mass in grams per 9000 meters of a fiber length. Trilobal or shaped fibers may be used in some cases to enhance the masking ability of the acquisition layer 52. The fibers may also have other deniers for different situations.

Some example acquisition layer compositions of the present disclosure are presented in Table 1 below compared to a prior art acquisition material. Note that the density of the samples of the present disclosure have a higher density than the density of the prior art sample.

TABLE 1

| Option | Prior Art | Sample 1 | Sample 2 | Sample 3 | Sample 4 | Sample 5 |
|---|---|---|---|---|---|---|
| 6 den (%) | 50 | | | | | |
| Fiber basis weight (gsm) | 15.05 | | | | | |
| 9 den (%) | 50 | | | | | |
| Fiber basis weight (gsm) | 15.05 | | | | | |
| 4 den (%) | | 100 | 70 | 50 | 30 | |
| Fiber basis weight (gsm) | | 30.1 | 21.07 | 15.05 | 9.03 | |
| 1.5 den (%) | | 0 | 30 | 50 | 70 | 100 |
| Fiber basis weight (gsm) | | | 9.03 | 15.05 | 21.07 | 30.1 |
| Total Fiber basis weight (gsm) | 30.1 | 30.1 | 30.1 | 30.1 | 30.1 | 30.1 |
| Binder add-on level (%) | 30 | 30 | 30 | 30 | 30 | 30 |
| Binder basis weight (gsm) | 12.9 | 12.9 | 12.9 | 12.9 | 12.9 | 12.9 |
| Total Material Basis weight gsm) | 43.0 | 43.0 | 43.0 | 43.0 | 43.0 | 43.0 |
| Capillary Sorption | | | | | | |

TABLE 1-continued

| Option | Prior Art | Sample 1 | Sample 2 | Sample 3 | Sample 4 | Sample 5 |
|---|---|---|---|---|---|---|
| Average H20 (cm) | 2.5 | 2.7 | 4.2 | 5.8 | 6.4 | 6.9 |
| Density @ 0.5 kPa Pressure | 0.045 | 0.055 | 0.066 | 0.087 | 0.086 | 0.118 |

The acquisition layer 52 may comprise a binder (e.g., a latex binder) to join or hold the fibers together. The binder may be about 10% to about 50%, about 10% to about 40%, about 20% to about 30%, about 15%, about 20%, about 25%, about 30%, or about 35%, by weight of the acquisition layer 52, specifically reciting all 0.1% increments with the above-specified ranges and all ranges formed therein or thereby. The acquisition materials of the present disclosure may comprise less than 50%, by weight of the acquisition material, of the latex binder, and may comprise less than 45%, or less than 40%, or less than 35%, by weight of the acquisition materials, of the latex binder.

The binder may have a glass transition temperature (Tg) of about −60° C. to about 0° C., about −50° C. to about −20° C., about −45° C. to about −30° C., about −45° C. to about −35° C., or about −40° C., specifically reciting all 0.1° C. increments within the specified ranges and all ranges formed therein or thereby.

A suitable latex binder may be prepared by a process comprising the steps of:

(1) polymerizing a monomer mixture comprising styrene, itaconic acid, surfactant and water soluble free radical initiator to form a seed;

(2) sequentially adding equal increments of a monomer mixture of styrene, butadiene and acrylic acid to the seed under emulsion polymerization conditions to form a styrene-butadiene-acrylic acid copolymer; and then (3) neutralizing the styrene-butadiene-acrylic acid copolymer to a pH of about 4.5 to 7 to form the latex binder.

The binder may be applied onto the autogenously bonded carded fibrous web (e.g., precursor acquisition material). Subsequently, the latex binder may be cured, using methods known to those of skill in the art, such as by application of heat or radiation. The term "cured" refers to the latex binder being cross-linked. The curing of the treated staple fibers is affected by a temperature above the glass transition temperature of the binder.

The latex binder may be prepared by conventional emulsion polymerization techniques using one or more ethylenically unsaturated monomers and a polymeric surfactant as herein disclosed and additional conventional additives such as free-radical initiators, optional chain transfer agents, chelating agents and the like may be utilized as set forth in U.S. Pat. No. 5,166,259 to Schmeing et al.

The latex is prepared by polymerizing a monomer mixture comprising styrene, itaconic acid, surfactant and a water soluble free radical initiator to form a seed. A monomer mixture is then added incrementally to the seed under emulsion polymerization conditions. The monomer mixture includes styrene, butadiene, and acrylic acid. The acrylic acid may help in the cross-linking process of the binder upon curing. The monomer mixture may be added incrementally to the seed to form a styrene-butadiene-acrylic acid copolymer. The mixture may comprise about 34 wt % to about 70 wt % styrene of the total composition. The monomer mixture may also comprise about 0.5 wt % to about 2.5 wt % itaconic acid, or about 2 wt % itaconic acid of the total composition, about 20 wt % to about 55 wt % butadiene and acrylic acid in an amount of about 6 wt % to about 10 wt %, or about 8 wt %.

A surfactant is added to the monomer mixture in an amount of about 0.05 wt % to about 2.0 wt %. The surfactant may be most any suitable emulsifier, soap, or the like known in the art and suitable at the pH of the latex. Examples of suitable emulsifiers and surfactants include alkyl sulfates, alkyl sulfosuccinates, alkyl aryl sulfonates, alpha-olefin sulfonates, fatty or rosin acid salts, only or octyl phenol reaction products of ethylene oxide and the like. Other surfactants that may be used include those identified in Surface Active Agents, Schwartz and Berry, Vol. 1, Interscience Publishers, Inc., New York, 1958; Surface Activity, Moilet, Collie and Black, D. Van Nostrand Company, Inc., New York, 1961; Organic Chemistry, Feiser and Feiser, D.C. Heath and Company, Boston, 1944; and The Merck Index, Seventh Edition, Merck & Co., Inc., Rahway, N.J., 1960.

The copolymer may then be neutralized to a pH of about 4.5 to 7.0 to form the latex. The pH of the latex is neutralized by addition of a base. Examples of a suitable base comprise potassium hydroxide, sodium bicarbonate, ammonium hydroxide, sodium hydroxide and the like. The amount of base added to the latex may be adjusted to obtain the desired pH range as is generally known in the art.

Polymerization is typically carried out from about 65° C. to about 75° C. Polymerization is generally conducted for about 4 to about 24 hours, however polymerization conditions may vary as desired to provide different conversion levels of monomer to copolymer. The monomer mixture is allowed to react until substantially constant solids at which time at least 99% of the monomers have been converted.

Gradient of Median Absorption Pressure

The absorbent articles of the present disclosure may have a gradient of Median Absorption Pressure that generally increases from the topsheet to the absorbent core or a material under the acquisition layer (e.g., the distribution layer). The topsheet may have a Median Absorption Pressure in the range of about 1 cm to about 4 cm, or about 2 cm to about 3 cm, according to the Capillary Sorption Test herein. The acquisition layer may have a Median Absorption Pressure in the range of about 3 cm to about 8 cm, or about 4 cm to about 7 cm, according to the Capillary Sorption Test herein. A material under the acquisition layer (e.g., an absorbent core or a distribution layer) may have a Median Absorption Pressure of about 8 cm to about 11 cm, or about 8 cm to about 10 cm, according to the Capillary Sorption Test herein. If a material is provided under the acquisition layer and an absorbent core is provided under the material, the material and/or the absorbent core may have a Median Absorption Pressure of about 8 cm to about 11 cm, or about 8 cm to about 10 cm, according to the Capillary Sorption Test herein. All ranges in this paragraph specifically include any smaller ranges formed therein and specifically recite all 0.1 cm increments within the specified ranges.

Fastening System

The absorbent article may include a fastening system. The fastening system may be used to provide lateral tensions about the circumference of the absorbent article to hold the absorbent article on the wearer as is typical for taped diapers. This fastening system may not be necessary for training pant articles since the waist region of these articles is already bonded. The fastening system may comprise a fastener such as tape tabs, hook and loop fastening components, interlocking fasteners such as tabs & slots, buckles, buttons, snaps, and/or hermaphroditic fastening components, although any other suitable fastening mechanisms are also within the scope of the present disclosure. A landing zone 44 is normally provided on the garment-facing surface of the front waist region 5 for the fastener to be releasably attached thereto.

Front and Rear Ears

The absorbent article may comprise front ears 46 and rear ears 40. The ears may be an integral part of the chassis, such as formed from the topsheet 24 and/or backsheet 26 as side panels. Alternatively, as represented on FIG. 1, the ears may be separate elements attached by gluing, heat embossing, and/or pressure bonding. The rear ears 40 may be stretchable to facilitate the attachment of the tabs 42 to the landing zone 44 and maintain the taped diapers in place around the wearer's waist. The rear ears 40 may also be elastic or extensible to provide a more comfortable and contouring fit by initially conformably fitting the absorbent article to the wearer and sustaining this fit throughout the time of wear well past when absorbent article has been loaded with fluids or other bodily exudates since the elasticized ears allow the sides of the absorbent article to expand and contract.

Elastic Waist Feature

The absorbent article 20 may also comprise at least one elastic waist feature (not represented) that helps to provide improved fit and containment. The elastic waist feature is generally intended to elastically expand and contract to dynamically fit the wearer's waist. The elastic waist feature may extend at least longitudinally outwardly from at least one waist edge of the absorbent core 28 and generally forms at least a portion of the end edge of the absorbent article. Disposable diapers may be constructed so as to have two elastic waist features, one positioned in the front waist region and one positioned in the rear waist region.

Relations Between the Layers

Typically, adjacent layers and components may be joined together using conventional bonding methods, such as adhesive coating via slot coating or spraying on the whole or part of the surface of the layer, thermo-bonding, pressure bonding, or combinations thereof. This bonding is not represented in the Figures (except for the bonding between the raised element of the leg cuffs 65 with the topsheet 24) for clarity and readability, but bonding between the layers of the article should be considered to be present unless specifically excluded. Adhesives may be used to improve the adhesion of the different layers between the backsheet 25 and the core wrap. The glue may be any suitable hotmelt glue known in the art.

Sanitary Napkin

Figure 9:
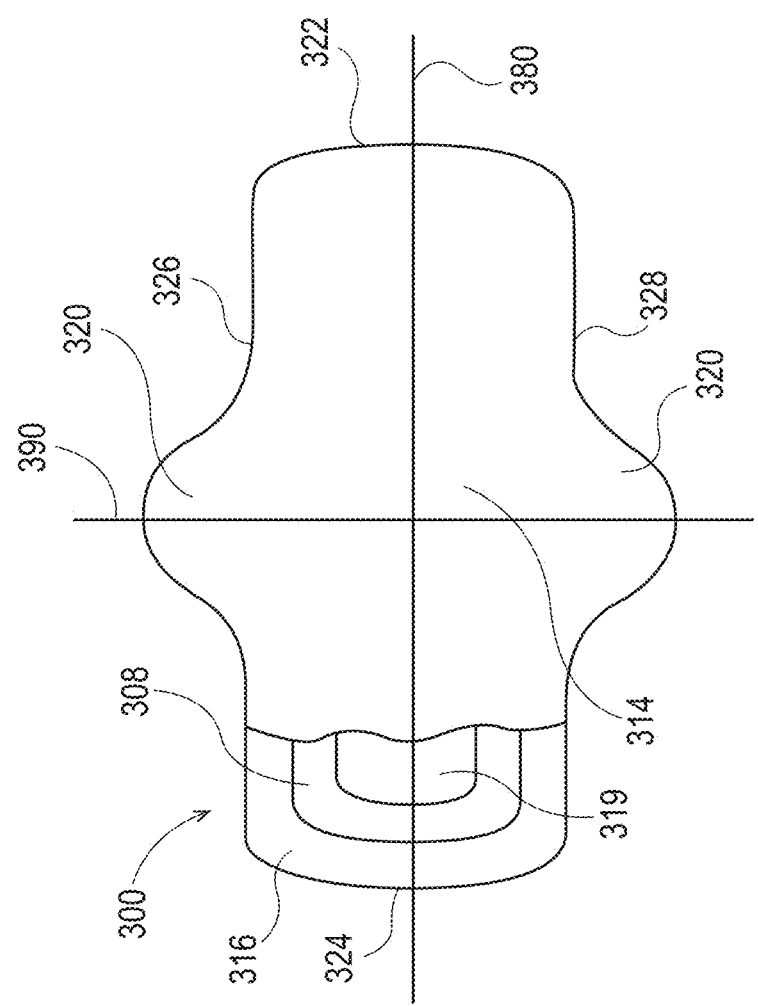
FIG. 9 is a top view of an absorbent article, wearer-facing surface facing the viewer, that is a sanitary napkin with some of the layers cut away in accordance with the present disclosure.

The three-dimensional substrates of the present disclosure may form a portion of a topsheet, form the topsheet, form a portion of, or all of a secondary topsheet, or be positioned on or joined to at least a portion of the topsheet of a sanitary napkin. Referring to FIG. 9, the absorbent article may comprise a sanitary napkin 300. The sanitary napkin 300 may comprise a liquid permeable topsheet 314, a liquid impermeable, or substantially liquid impermeable, backsheet 316, and an absorbent core 308. The absorbent core 308 may have any or all of the features described herein with respect to the absorbent cores 28 and, in some forms, may have a secondary topsheet instead of the acquisition-distribution system disclosed above. The sanitary napkin 300 may also comprise wings 320 extending outwardly with respect to a longitudinal axis 380 of the sanitary napkin 300. The sanitary napkin 300 may also comprise a lateral axis 390. The wings 320 may be joined to the topsheet 314, the backsheet 316, and/or the absorbent core 308. The sanitary napkin 300 may also comprise a front edge 322, a rear edge 324 longitudinally opposing the front edge 322, a first side edge 326, and a second side edge 328 longitudinally opposing the first side edge 326. The longitudinal axis 380 may extend from a midpoint of the front edge 322 to a midpoint of the rear edge 324. The lateral axis 390 may extend from a midpoint of the first side edge 326 to a midpoint of the second side edge 328. The sanitary napkin 300 may also be provided with additional features commonly found in sanitary napkins as is generally known in the art, such as a secondary topsheet 319, for example.

Three-Dimensional Substrates

The three-dimensional, liquid permeable substrates of the present disclosure may comprise substrates that have first elements (e.g., projections) that have a first z-directional height and at least second elements (e.g., land areas) that have a second z-directional height. The substrates may also have a plurality of apertures. The substrates may also have at least third elements having at least a third z-directional height. Owing to such structures, fluids may be quickly moved away from the skin of a wearer, leaving primarily the first elements having the first z-directional heights contacting the skin of the wearer, thereby making the wearer feel dryer. The fluids may flow via gravity or via capillary gradient into the second elements having the second z-directional heights and/or into and through the apertures, so that the fluids may be absorbed into the absorbent articles. By providing the three-dimensional substrates of the present disclosure, fluid/skin contact and the time that fluids are in contact with the skin of a wearer may be reduced. Further, the first elements having the first z-directional heights may act as a spacer between the fluids and the skin of the wearer while the fluids are being absorbed into the absorbent article. The three-dimensional substrates may be used as topsheets or outer cover materials.

Figure 10:
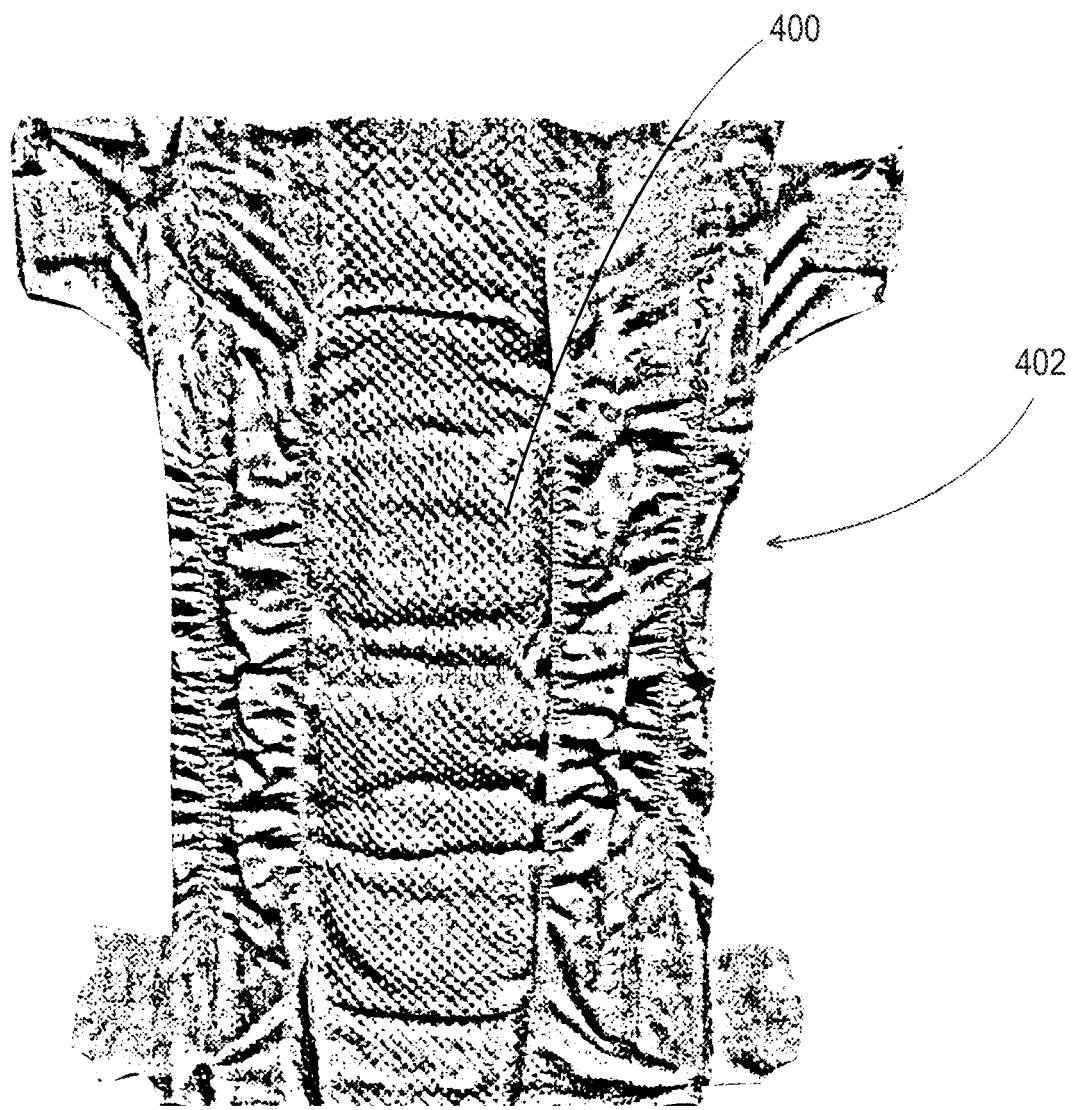
FIG. 10 is a top view of an absorbent article, wearer-facing surface facing the viewer, that comprises a three-dimensional, liquid permeable substrate in accordance with the present disclosure.
Figure 11:
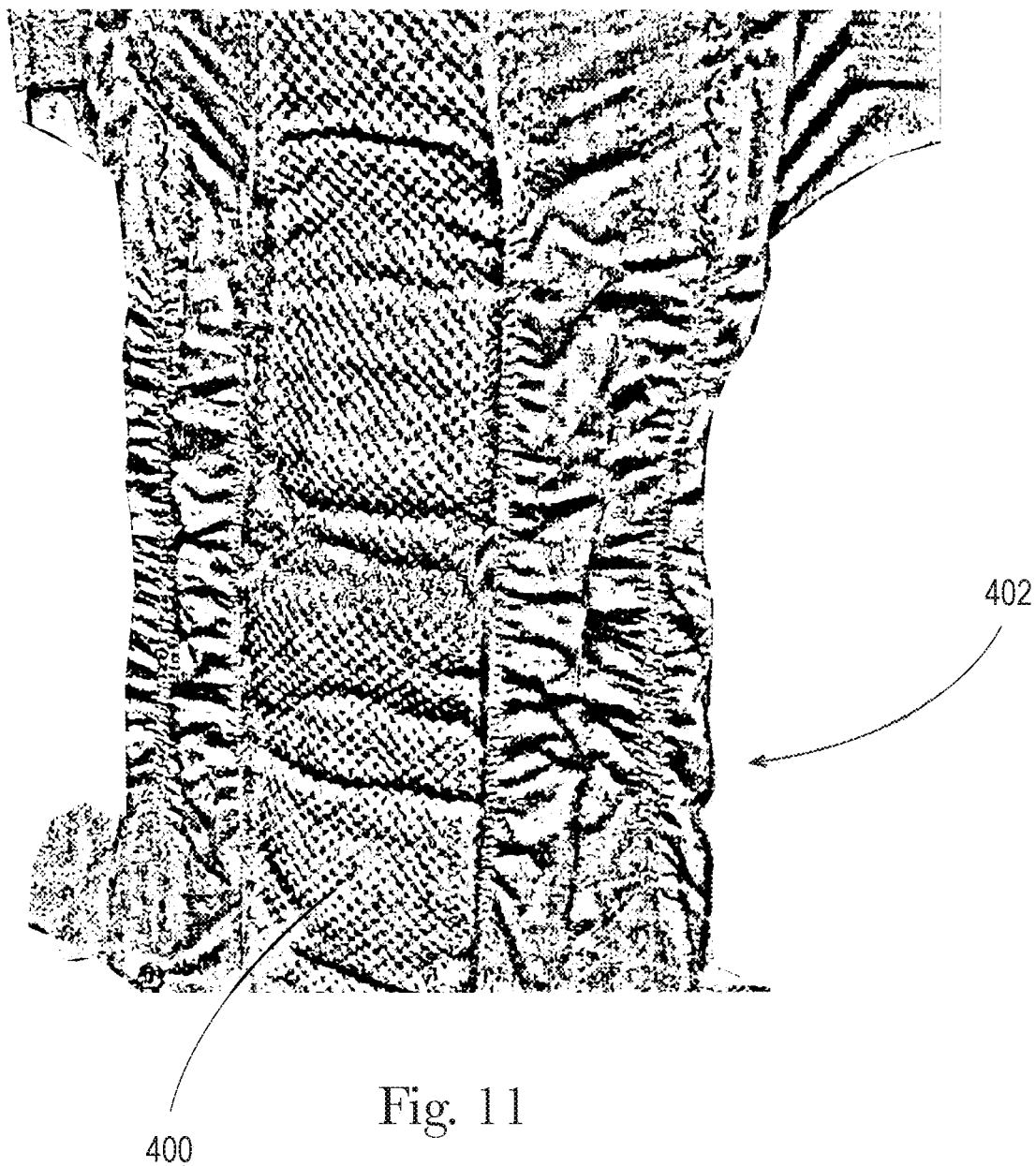
FIG. 11 is a perspective view of an absorbent article of FIG. 10 in accordance with the present disclosure.
Figure 12:
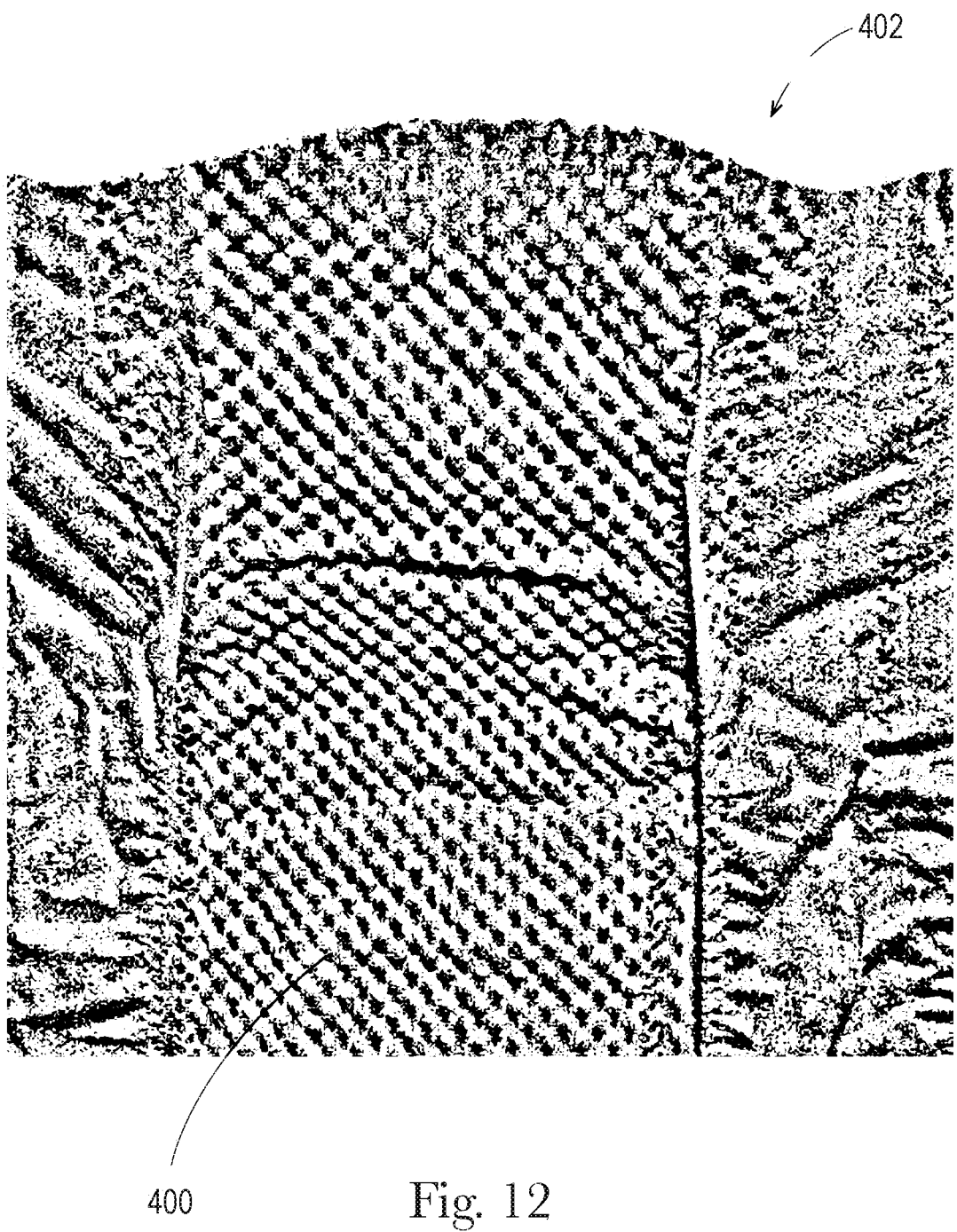
FIG. 12 is an enlarged top view of a portion of the liquid permeable substrate of FIG. 10 in accordance with the present disclosure.
Figure 13:
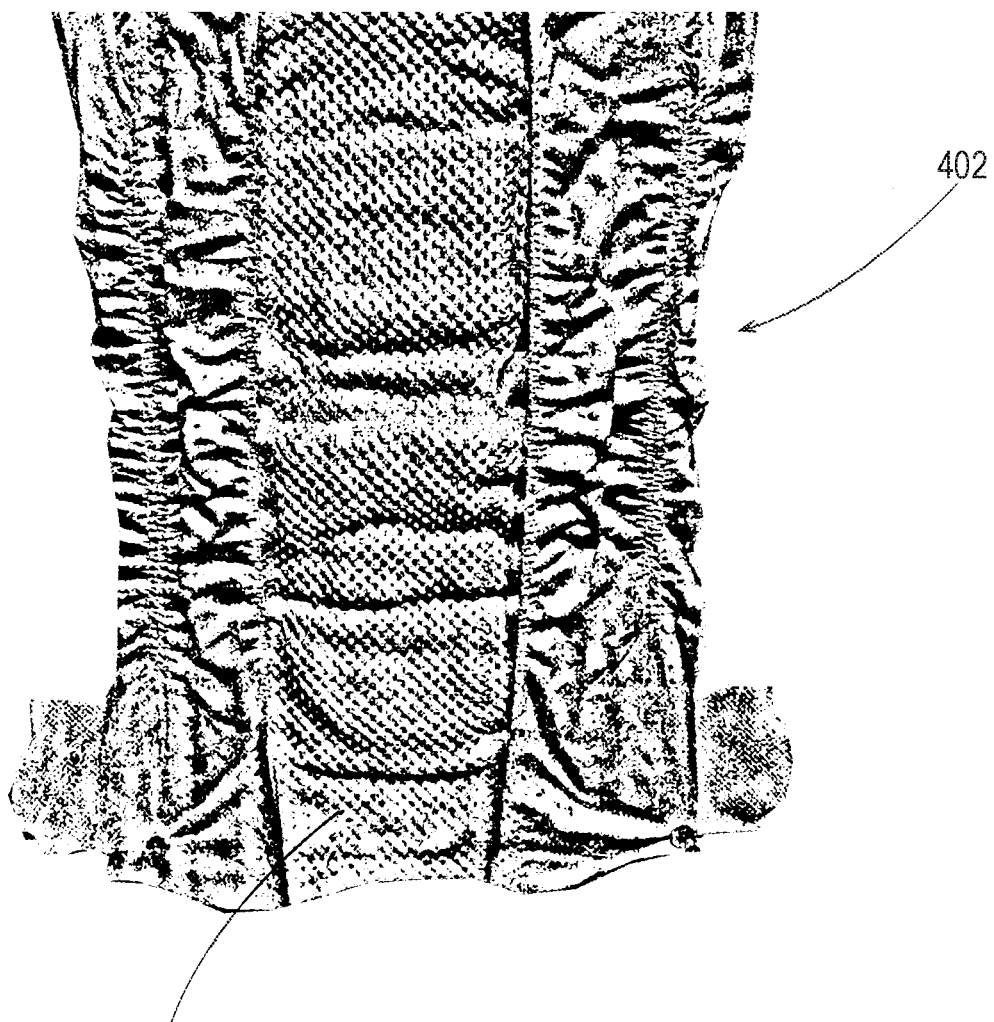
FIG. 13 is another enlarged top view of a portion of the liquid permeable substrate of FIG. 10 in accordance with the present disclosure.

Referring to FIGS. 10-13, a three-dimensional, liquid permeable substrate 400 (referred to herein both as a three-dimensional substrate or a liquid permeable substrate) is illustrated an on absorbent article 402. FIG. 10 is a top view of the absorbent article 402 with the wearer-facing surface facing the viewer. FIG. 11 is a perspective view of the absorbent article 402 with the wearer-facing surface facing the viewer. FIG. 12 is a top view of a portion of the liquid preamble substrate 400 on the absorbent article with the wearer-facing surface facing the viewer. FIG. 13 is another top view of a portion of the liquid permeable substrate 400 on the absorbent article 402 with the wearer-facing surface facing the viewer.

In one form, the liquid permeable substrate 400, or other liquid permeable substrates described herein, may comprise a patch or strip positioned on and/or joined to a topsheet of the absorbent article 402. The patch or strip may be bonded to the topsheet, adhesively attached to the topsheet, cold-pressure welded to the topsheet, ultrasonically bonded to the topsheet, and/or otherwise joined to the topsheet. Alternatively, the liquid permeable substrates of the present disclosure may comprise the topsheet (e.g., topsheet 24), form all of the topsheet, or form a portion of the topsheet. Also, the topsheet 24 may be comprised only of one or more of the liquid permeable substrates of the present disclosure. In any of the various configurations, the liquid permeable substrates of the present disclosure are intended to form at least a portion of the wearer-facing surface of an absorbent article and be in at least partial contact with the skin of a wearer.

Figure 14:
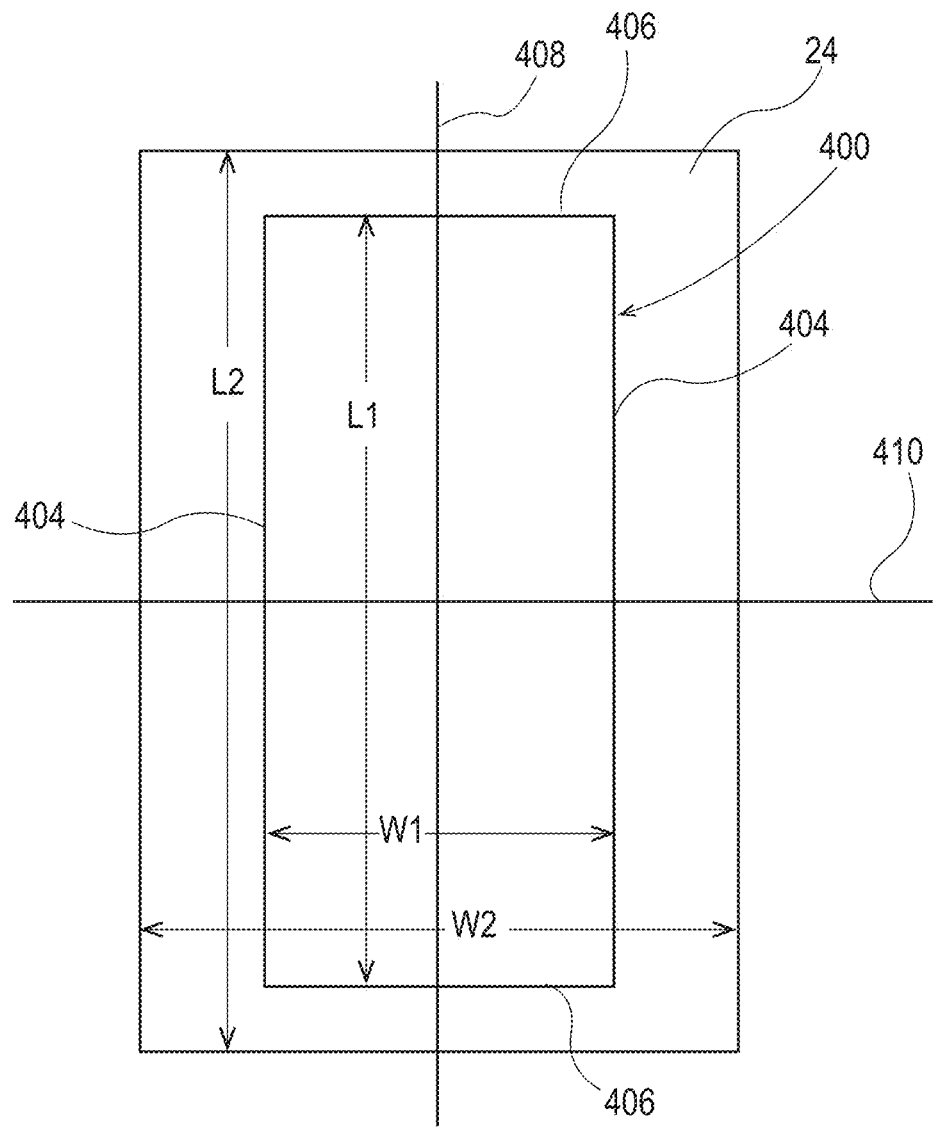
FIG. 14 is a schematic illustration of a three-dimensional, liquid permeable substrate positioned on and/or joined to a topsheet for an absorbent article in accordance with the present disclosure.
Figure 15:
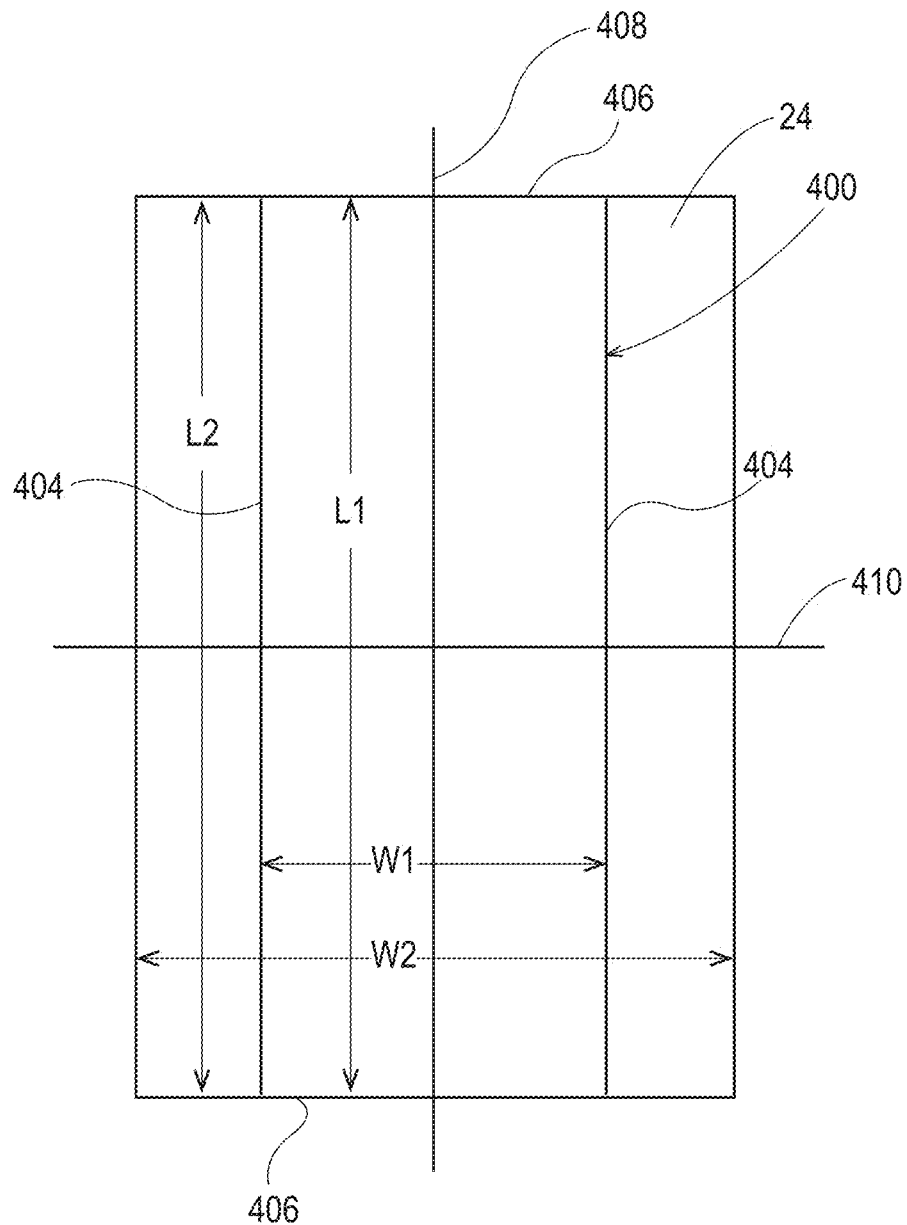
FIG. 15 is another schematic illustration of a three-dimensional, liquid permeable substrate positioned on and/or joined to a topsheet for an absorbent article in accordance with the present disclosure.
Figure 16:
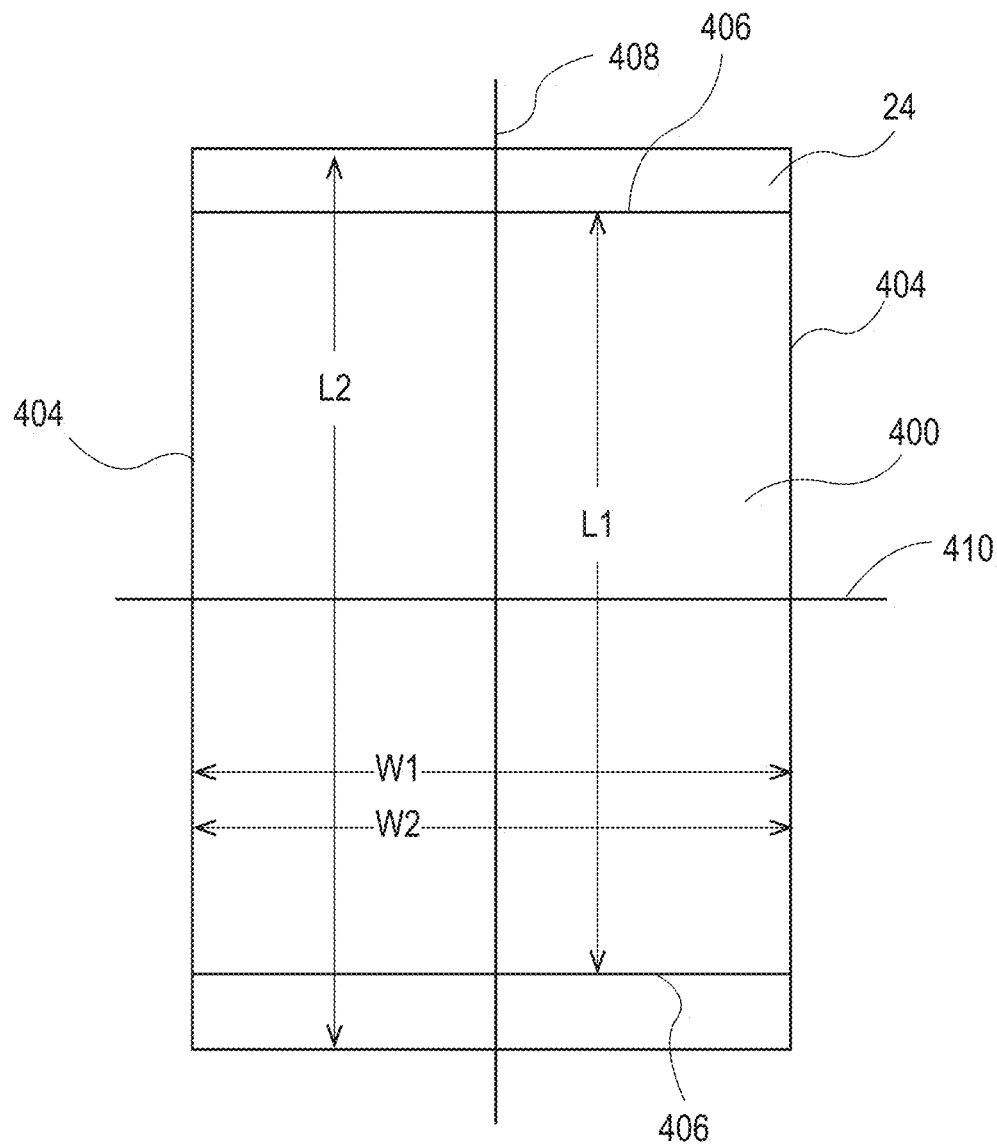
FIG. 16 is another schematic illustration of a three-dimensional, liquid permeable substrate positioned on and/or joined to a topsheet for an absorbent article in accordance with the present disclosure.

Referring to FIGS. 14-16, the liquid permeable substrate 400, or other liquid permeable substrates described herein, in a patch or strip form joined to the topsheet 24, may have a cross machine directional width of W1, while the topsheet 24 may have a cross machine directional width of W2. W1 may be less than, the same as, substantially the same as, or greater than (not illustrated) the width W2. The width W1 may also vary or be constant throughout a longitudinal length of the liquid permeable substrates. Still referring to FIGS. 14-16, the liquid permeable substrate 400, or other liquid permeable substrates described herein, in a patch or strip form, may have a machine directional length of L1, while the topsheet 24 may have a machine directional length of L2. L1 may be less than, the same as, substantially the same as, or greater than (not illustrated) the length L2. The length L1 may vary or be constant across the width W1 of the liquid permeable substrates. Although not illustrated in FIGS. 14-16, the lengths and widths of the topsheet 24 and the liquid permeable substrates may be the same, or substantially the same.

Although the patch or strip of the liquid permeable substrate 400 is illustrated as being rectangular in FIGS. 14-16, the liquid permeable substrates of the present disclosure may also have any other suitable shapes, such a front/back profiled shape (i.e., wider in the front, wider in the back, and/or narrower in the crotch), a square shape, an ovate shape, or other suitable shape. The side edges 404 and/or the end edge 406 of the liquid permeable substrate 400 may have one or more arcuate portions, designs, and/or shapes cut out from them to provide an aesthetically pleasing look to the liquid permeable substrate 400. One side edge 404 may be symmetrical or asymmetrical to another side edge 404 about a longitudinal axis, 408, of the topsheet 24. Likewise, one end edge 406 may be symmetrical or asymmetrical to another side edge 406 about a lateral axis, 410 of the topsheet 24.

The liquid permeable substrate 400 may comprise one or more layers. If more than one layer is provided, the layers may be joined together or attached to each other through mechanical bonding, adhesive bonding, pressure bonding, heat bonding, passing heated air through both layers, or by other methods of joining to form the multilayer substrate 400. Alternatively, the layers are formed in subsequent fiber laydown steps, such as a first and a second carding operation for a first type and a second type of staple fibers or two subsequent beams of spunlaying polymeric filaments comprising additives. The first layer may comprise one or more hydrophobic materials, or may be fully hydrophobic, and the second layer may comprise one or more hydrophilic materials, or may be fully hydrophilic. Instead of one layer comprising a hydrophobic material and the other layer comprising a hydrophilic material, one layer may comprise a material that is more hydrophobic or more hydrophilic than the material that comprises the other layer (e.g., both layers are hydrophilic, but one layer is more hydrophilic or both layers are hydrophobic, but one layer is more hydrophobic). The first layer may comprise a hydrophobic layer and the second layer may comprise a hydrophilic layer or vice versa. The first layer may be used as a portion of, or all of, the wearer-facing surface of the absorbent article. Alternatively, the second layer may be used as a portion of, or all of, the wearer-facing surface of the absorbent article.

The rationale for having the first layer (or wearer-facing layer) being comprised of a hydrophobic material is twofold. First, if the liquid permeable substrate is apertured, the hydrophobic layer will not retain as much liquid as the hydrophilic second layer and thus, there will be less fluid (e.g., urine) in direct contact with the skin of a wearer. Second, projections (described below) in the first and second layers generally form hollow portions or arches on a garment-facing side of the liquid permeable substrate that do not have direct contact with the ADS or core, so fluids can get caught in the hollow arches. Without good connectivity of the hollow arches to the ADS or the core, the liquid permeable substrate may retain more fluid and feel wetter to the wearer. With a hydrophobic first layer, however, any liquid that is wicked into the hollow arches will be mostly on the garment-facing, or downward-facing hydrophilic side of the liquid permeable substrate, thereby leaving the first hydrophobic layer dryer. In principle, this may be achieved with a hydrophilic or capillary gradient from the first layer to the second layer (e.g. finer fibers in the second layer with same hydrophilic properties (i.e., contact angle with the liquid)). The apertures in the substrate may play an important role to enable initial and fast fluid flow (strike-through) despite the first hydrophobic layer. Therefore, the first hydrophobic layer works in concert with the protrusions, hollow arches, and the apertures to reduce wetness on the wearer-facing surface of the liquid permeable substrate. In other instances, the second layer may be used as a portion of the wearer-facing surface.

The first layer may comprise a plurality of first fibers and/or filaments (hereafter together referred to as fibers). The plurality of first fibers may comprise fibers that are the same, substantially the same, or different in size, shape, composition, denier, fiber diameter, fiber length, and/or weight. The second layer may comprise a plurality of second fibers. The plurality of second fibers may comprise fibers that are the same, substantially the same, or different in size, shape, composition, denier, fiber diameter, fiber length, and/or weight. The plurality of first fibers may be the same as, substantially the same as, or different than the plurality of second fibers. Additional layers may have the same or different configurations.

The first layer and/or the second layer may comprise bicomponent fibers having a sheath and a core. The sheath may comprise polyethylene and the core may comprise polyethylene terephthalate (PET). The sheath and the core may also comprise any other suitable materials known to those of skill in the art. The sheath and the core may each comprise about 50% of the fibers by weight of the fibers, although other variations (e.g., sheath 60%, core 40%; sheath 30%, core 70% etc.) are also within the scope of the present disclosure. The bicomponent fibers or other fibers that make up the first and/or second layers may have a denier in the range of about 0.5 to about 6, about 0.5 to about 4, about 0.5 to about 3, about 1 to about 3, about 1.0 to about 4, about 1.5 to about 4, about 1.5 to about 3, about 1.5 to about 2.5, or about 2, specifically including all 0.1 denier increments within the specified ranges and all ranges formed therein or thereby. Denier is defined as the mass in grams per 9000 meters of a fiber length. In other instances, the denier of the fibers of the first layer may be in the range of about 1.5 denier to about 6 denier or about 2 denier to about 4 denier and the denier of the fibers of the second layer may be in the range of about 1.2 denier to about 3 denier or about 1.5 denier to about 3 denier, specifically reciting all 0.1 denier increments within the specified ranges and all ranges formed therein or thereby. In certain instances, the fibers of the first layer may be at least 0.5 denier, at least 1 denier, at least 1.5 denier, or at least 2 denier greater than the denier of the fibers of the second layer depending at least in part on the particular acquisition and/or distribution system in use in a certain absorbent article. By providing the fibers of the first layer with a denier higher than a denier of the fibers of the second layer, a pore gradient is provided in the liquid permeable substrate. This pore gradient may provide better dryness and/or acquisition in the liquid permeable substrate. The fibers having the larger denier in the first layer provide larger pores than the fibers having the smaller denier in the second layer, thereby producing the pore gradient between the layers.

The plurality of first and second fibers may also comprise any other suitable types of fibers, such as polypropylene fibers, other polyolefins, other polyesters besides PET such as polylactic acid, thermoplastic starch-containing sustainable resins, other sustainable resins, bio-PE, bio-PP, and Bio-PET, viscose fibers, rayon fibers, or other suitable nonwoven fibers, for example. These fibers may have any suitable deniers or denier ranges and/or fiber lengths or fiber length ranges. In an instance where the plurality of first and second fibers are the same or substantially the same, the plurality of second fibers may be treated with a hydrophilic agent, such as a surfactant, to cause the plurality of second fibers to become hydrophilic or at least less hydrophobic. The plurality of first fibers may not be treated with the surfactant such that they remain in their natural hydrophobic state or the plurality of first fibers may be treated with a surfactant to become less hydrophobic.

The first layer may have a basis weight in the range of about 10 gsm to about 25 gsm. The second layer may have a basis weight in the range of about 10 gsm to about 45 gsm. The basis weight of the substrate (both first and second layers) may be in the range of about 20 gsm to about 70 gsm, about 20 gsm to about 50 gsm, about 20 gsm to about 60 gsm, about 25 gsm to about 50 gsm, about 30 gsm to about 40 gsm, about 30 gsm, about 35 gsm, or about 40 gsm, for example.

In a form, the basis weight of the substrate may be about 30 gsm to about 40 gsm or about 35 gsm. In such an example, the first layer may have a basis weight in the range of about 10 gsm to about 20 gsm, or about 15 gsm, and the second layer may have a basis weight in the range of about 15 gsm to about 25 gsm, or about 20 gsm. In another example, the basis weight of the substrate may be about 20 gsm. In such an example, the first layer may have a basis weight of about 10 gsm and the second layer may have a basis weight of about 10 gsm. In still another example, the basis weight of the substrate may be about 60 gsm. In such an example, the first layer may have a basis weight of about 24 gsm, and the second layer may have a basis weight of 36 gsm. All other suitable basis weight ranges for the first and second layers and the substrates are within the scope of the present disclosure. Accordingly, the basis weight of the layers and the substrates may be designed for specific product requirements.

Specifically recited herein are all 0.1 gsm increments within the above-specified ranges of basis weight and all ranges formed therein or thereby.

In some instances, it may be desirable to have a higher basis weight in the first layer compared to the second layer. For instance, the first layer's basis weight may be at least about 1 to about 4 times, at least about 1 to about 3.5 times, about 1.5 to about 3 times, about 1.5 times to about 3 times, about 2 times, about 2.5 times, or about 3 times greater than the second layer's basis weight. In some instances, the basis weight of the first layer may be in the range of about 20 gsm to about 30 gsm, and the basis weight of the second layer may be in the range of about 10 gsm to about 20 gsm, for example. Specifically recited herein are all 0.1 gsm increments within the above-specified ranges of basis weight and all ranges formed therein or thereby. By providing the first layer (hydrophobic) with a higher basis weight than the second layer (hydrophilic), more hydrophobic material than hydrophilic material is provided in the liquid permeable substrate. Upon information and belief, more hydrophobic material and less hydrophilic material in the liquid permeable substrate provides for better acquisition and/or dryness. The surface tension of the hydrophilic layer may be reduced to at least inhibit the hydrophilic layer (second layer) from contaminating the hydrophobic layer (first layer) (and making it more hydrophilic) upon the liquid permeable substrate receiving one or more gushes.

The liquid permeable substrates of the present disclosure may also form a portion of, or all of, the outer cover 23 which is joined to at least a portion of the backsheet 25. In other instances, the outer cover 23 may comprise a pattern (e.g., embossed pattern, printed pattern) and/or three-dimensional structure that is the same as, or similar in appearance to, the liquid permeable substrates of the present disclosure. In general, the appearance of at least a portion of a liquid permeable substrate on the wearer-facing surface may match, or substantially match, at least a portion of the outer cover 23 or another portion of absorbent article.

Figure 25:
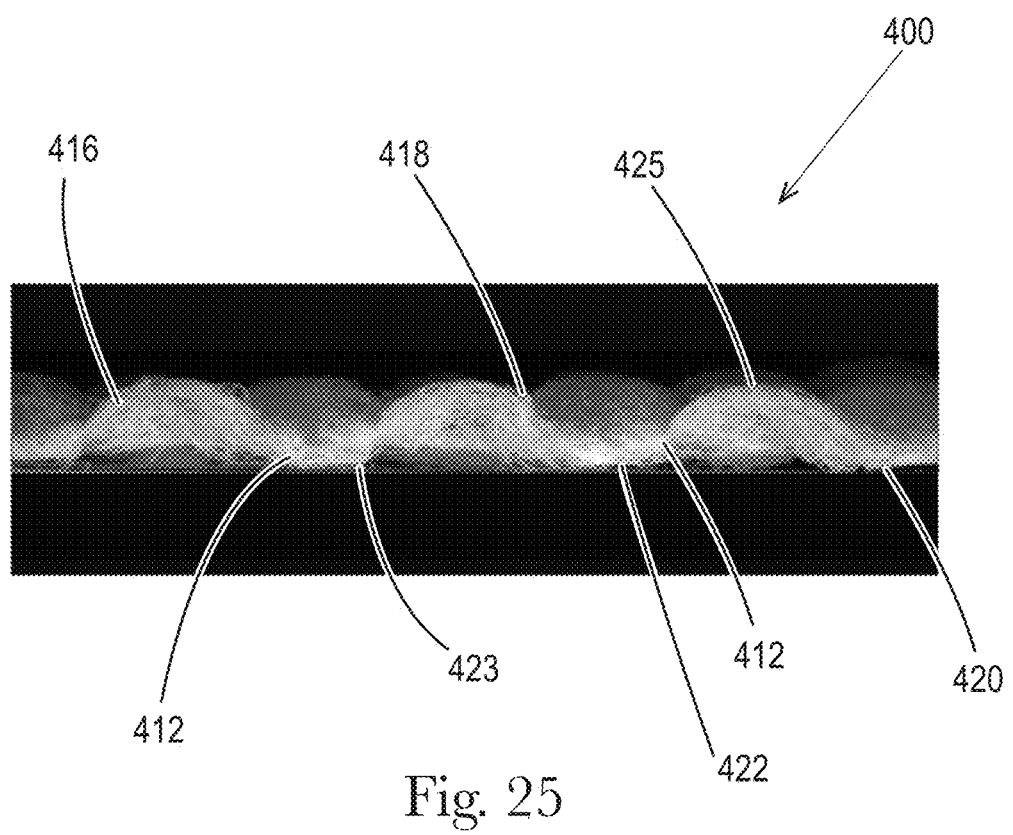
FIG. 25 is a cross-sectional view of the liquid permeable substrate in accordance with the present disclosure.

FIG. 17 is a front view of a portion of a three-dimensional, liquid permeable substrate, wearer-facing surface facing the viewer. FIG. 18 is a front perspective view of the portion of the three-dimensional, liquid permeable substrate of FIG. 17. FIG. 19 is another front view of a portion of a three-dimensional, liquid permeable substrate, wearer-facing surface facing the viewer. FIG. 20 is a front perspective view of the portion of the liquid permeable substrate of FIG. 19. FIG. 21 is a back view of a portion of a three-dimensional, liquid permeable substrate, wearer-facing surface facing the viewer. FIG. 22 is a back perspective view of the portion of the three-dimensional, liquid permeable substrate of FIG. 21. FIG. 23 is another back view of a portion of a three-dimensional, liquid permeable substrate, wearer-facing surface facing the viewer. FIG. 24 is a back perspective view of the portion of the liquid permeable substrate of FIG. 23. FIG. 25 is a cross-sectional view of the liquid permeable substrate.

Referring generally to FIGS. 17-25, the liquid permeable substrate 400 may comprise a first layer and a second layer, or more than two layers or one layer. The substrate 400 may comprise a plurality of land areas 412, a plurality of recesses 414, and a plurality of projections 416. The plurality of projections 416 may form the first elements having the first z-directional height, and the land areas 412 may form the second elements having the second z-direction height, as described above. The plurality of land areas 412, the plurality of recesses 414, and the plurality of projections 416 may together form a first three-dimensional surface on a first side 418 of the substrate 400. The plurality of land areas 412, the plurality of recesses 414, and the plurality of projections 416 may also form a second three-dimensional surface on a second side 420 of the substrate 400. The projections 416 may be generally dome shaped on a wearer-facing surface of the liquid permeable substrate 400 and may be hollow arch-shaped on the garment-facing surface of the substrate 400. All of, or a majority of (i.e., more than 50% of, or more than 75% of), or substantially all of, the recesses 414 may define an aperture 422 therein at a location most distal from a top peak 425 of an adjacent projection 416. A perimeter 423 of a majority of, or all of, the apertures 422 may form a bottommost portion or plane of the substrate 400, while the top peak 425 (i.e., uppermost portion) of a majority of, or all of, the projections 416 may form a topmost portion or plane of the substrate 400. In other instances, the substrate may not have apertures within the recesses 414 and the portion of the recesses 414 most distal from the top peaks 425 of the projections 416 may form the bottommost portion or plane of the substrate 400. The apertures 422 may extend through the first and the second layers of the substrate 400.

The land areas 412 may be positioned intermediate: (1) adjacent projections 416, (2) adjacent recesses 414 and/or adjacent apertures 422. The land areas 412 may also surround at least a portion of, or all of, a majority of, or all of, the recesses 414 and/or the apertures and at least a majority of, or all of, the projections 416. The land areas 412 may be positioned between a plane of a perimeter of at least a majority of the apertures 422 and a plane of at least a majority of the top peaks 425 of the projections 416.

The projections 416 may alternate with the recesses 414 and/or the apertures 422 in a direction generally parallel with a lateral axis 424 of the liquid permeable substrate 400. The lateral axis 424 is generally parallel with the lateral axis 410 illustrated in FIGS. 14-16. The projections 416 may also alternate with the recesses 414 and/or apertures 422 in a direction generally parallel with a longitudinal axis 426 of the liquid permeable substrate 400. The longitudinal axis 426 is generally parallel with the longitudinal axis 408 illustrated in FIGS. 14-16. In such a configuration, in a direction generally parallel with the lateral axis 424 or in a direction generally parallel with the longitudinal axis 426, the projections 416 and the recesses 414 and/or apertures 422 alternate (i.e., projection, recess and/or apertures, projection, recess and/or aperture). This feature provides better softness to the substrate 400 in that there is a soft projection peak 425 intermediate most of, or all of, adjacent recesses 414 and/or apertures 422. This feature also helps maintain the skin of a wearer away from fluids in the land areas 412 and/or the recesses 414, since the projections 416 essentially create a spacer between the skin and the fluids.

Two or more adjacent projections 416 may be separated from each other by a recess 414 and/or an aperture 422 and one or more land areas 412 in a direction generally parallel to the lateral axis 424 or in a direction generally parallel to the longitudinal axis 426. Two or more adjacent recesses 414 and/or apertures 422 may be separated by a projection 416 and one or more land areas 412 in a direction generally parallel to the lateral axis 424 or in a direction generally parallel to the longitudinal axis 426. The land areas 412 may fully surround the apertures 422 and the projections 416. The land areas 412 may together form a generally continuous grid through the substrate 400, while the projections 416 and the recesses 414 and/or the apertures 422 may be discrete elements throughout the substrate.

In some instances, two or more, such as four projections 416 may be positioned around at least a majority of, substantially all of, or all of, the recesses 414 and/or the apertures 422 (this does not include the land areas 412 intermediate the projections 416 and the recesses 414 and/or the apertures 422). Two or more recesses 414 and/or apertures 422, such as four, may be positioned around at least a majority of, substantially all of, or all of, the projections 416 (this does not include the land areas 412 intermediate the recesses 414 and/or the apertures 422 and the projections 416). The projections 416, recesses 414, apertures 422, and land areas 412 may all be formed of portions of the first and second layers of the substrate. If more than two layers are provided in a substrate, the projections 416, recesses 414, apertures 422, and land areas 412 may all be formed of portions of the first, second and third layers of the substrate. The same may be true if more than three layers are provided in a particular substrate. In other instances, the land areas 412 may only be formed in the first layer.

The apertures 422 and/or the recesses 414 may comprise a first set of apertures and/or recesses 414 together forming a first line in the substrate 400 and a second set of apertures 422 and/or recesses 414 together forming a second line in the substrate 400. The first line may be generally parallel with or generally perpendicular to the second line. The first line may also form an acute or obtuse angle with the second line. The projections 416 may comprise a first set of projections 416 together forming a first line in the substrate 400 and a second set of projections 416 together forming a second line in the substrate 400. The first line may be generally parallel with or generally perpendicular to the second line. The first line may also form an acute or obtuse angle with the second line.

The substrate 400 may be generally symmetrical about the lateral axis 424 and/or generally symmetrical about the longitudinal axis 426. In other instances, the substrate may not be symmetrical about the lateral axis 424 and/or the longitudinal axis 426.

In one form, the substrate 400 may comprise a first line comprising alternating apertures 422 and projections 416 extending in a direction parallel to the lateral axis 424 and a second adjacent line comprising alternating apertures 422 and projections 416 extending in the direction generally parallel to the lateral axis 424. The lines will run through the center of the apertures 422 and the projections 416. See for, example, FIG. 17, lines A and B. If a line, C, is drawn in a direction generally parallel to the longitudinal axis 426 and that intersects lines A and B, an aperture 422 will be located at the intersection of lines A and C and a projection 416 will be located at the intersection of the lines B and C. The same is true if lines A and B are drawn in a direction parallel to the longitudinal axis 426 and line C is draw in a direction generally parallel to the lateral axis 424, as illustrated in FIG. 19. If the lines are drawn at different locations, the intersection of lines A and C may have a projection 416 and the intersection of lines B and C may have an aperture 422. The main point being that the rows of apertures and the rows of projections are staggered. By staggering the apertures and projections in this fashion, better softness is achieved in the wearer-facing surface of the substrate 400 owing to a soft projection or projection crest being intermediate two apertures.

Parameters of the Three-Dimensional Substrates (or Topsheets)

The absorbent articles of the present disclosure may have a modified fluid acquisition less than about 250 seconds, less than about 200 seconds, less than about 175 seconds, less than about 160 seconds, less than about 150 seconds, less than about 140 seconds, less than about 135 seconds, less than about 130 seconds, less than about 125 seconds, less than about 120 seconds, less than about 115 seconds, less than about 110 seconds, or may be in the range of about 50 seconds to about 250 seconds, about 70 seconds to about 200 seconds, about 70 seconds to about 175 seconds, about 70 seconds to about 150 seconds, about of about 70 seconds to about 140 seconds, about 80 seconds to about 140 seconds, about 90 seconds to about 135 seconds, or about 100 seconds to about 130 seconds, all according to the Modified Fluid Acquisition Test herein, specifically reciting all 0.5 second increments with the above specified-ranges and all ranges formed therein or thereby.

The absorbent articles of the present disclosure may have a collagen rewet less than about 140 mg, less than about 130 mg, less than about 120 mg, less than about 110 mg, less than about 100 mg, less than about 90 mg, less than about 80 mg, less than about 75 mg, less than about 70 mg, less than about 68 mg, less than about 65 mg, less than about 63 mg, or may be in the range of about 25 mg to about 140 mg, about 30 mg to about 120 mg, about 30 mg to about 110 mg, about 30 mg to about 100 mg, about 35 mg to about 90 mg, about 40 mg to about 80 mg, about 50 mg to about 75 mg, or about 55 mg to about 70 mg, all according to the Collagen Rewet Test herein, specifically reciting all 0.1 mg increments with the above-specified ranges and all ranges formed therein or thereby.

The absorbent articles of the present disclosure may have a light touch dryness of less than about 100 mg, less than about 90 mg, less than about 80 mg, less than about 70 mg, less than about 60 mg, less than about 55 mg, less than about 50 mg, less than about 45 mg, less than about 40 mg, less than about 36 mg, or may be in the range of about 10 mg to about 90 mg, about 15 mg to about 80 mg, about 20 mg to about 70 mg, about 20 mg to about 60 mg, about 20 mg to about 50 mg, about 25 mg to about 45 mg, or about 30 mg to about 40 mg, all according to the Light Touch Dryness Test herein, specifically reciting all 0.1 mg increments with the above-specified ranges and all ranges formed therein or thereby.

All or a majority of the projections 416 may have a z-directional height in the range of about 300 µm to about 6000 µm, about 500 µm to about 5000 µm, about 500 µm to about 4000 µm, about 300 µm to about 3000 µm, about 500 µm to about 3000 µm, about 500 µm to about 2000 µm, about 750 µm to about 1500 µm, about 800 µm to about 1400 µm, about 900 µm to about 1300 µm, about 1000 µm to about 1300 µm, about 1100 µm to about 1200 µm, about 1165, about 1166, about 1167, or about 1150 µm to about 1200 µm, specifically reciting all 1 µm increments within the above-specified ranges and all ranges formed therein or thereby. The z-directional height of the projections 416 are measured according to the Projection Height Test described herein.

All or a majority of the recesses 414 may have a z-directional height in the range of about 200 µm to about 3000 µm, about 300 µm to about 2000 µm, about 100 µm to about 2000 µm, about 500 µm to about 2000 µm, about 500 µm to about 1500 µm, about 700 µm to about 1300 µm, about 800 µm to about 1200 µm, about 900 µm to about 1100 µm, about 900 µm to about 1000 µm, about 970 µm, or about 950 µm to about 1000 µm, specifically reciting all 1 µm increments within the above-specified ranges and all ranges formed therein or thereby. The z-directional height of the recesses 416 are measured according to the Recess Height Test described herein.

The substrate (or topsheet), 400, or portions thereof, may have an overall z-directional height in the range of about 500 µm to about 6000 µm, about 600 µm to about 6000 µm, about 750 µm to about 4000 µm, about 1000 µm to about 6000 µm, about 1500 µm to about 6000 µm, about 1000 µm to about 3000 µm, about 1500 µm to about 2500 µm, about 1750 µm to about 2300 µm, about 1900 µm to about 2300 µm, about 2000 µm to about 2300 µm, about 2100 µm to about 2250 µm, about 2136 µm, or about 2135 µm, specifically reciting all 1 µm increments within the above-specified ranges and all ranges formed therein or thereby. The overall z-directional height of the substrate 400, or portions thereof, is measured according to the Overall Substrate Height Test described herein.

The topsheet 24 may have an Equilibrium Capillary Suction Sorbent Capacity (CSSC) greater than 10 g/g at 100% saturation, according to the Capillary Sorption Test herein. The topsheet 24 may have a CSSC greater than 10 g/g at 100% saturation and less than 35 g/g at 100% saturation, according to the Capillary Sorption Test herein, specifically reciting all 0.1 g/g increments within the specified range. The acquisition layer 52, or layer under the topsheet, may have a CSSC of less than 7 g/g at 100% saturation, according to the Capillary Sorption Test herein. The acquisition layer 52, or other material under the topsheet, may have a CSSC of less than 7 g/g at 100% saturation and greater than 1 g/g at 100% saturation, according to the Capillary Sorption Test herein, specifically reciting all 0.1 g/g increments within the specified range. The topsheet 24 may have a greater CSSC at 100% saturation than the CSSC at 100% saturation of the acquisition layer 52 or other material under the topsheet.

A majority of, or all of, the apertures 422 may have an effective aperture area in the range of about 0.4 mm$^2$ to about 10 mm$^2$, about 0.5 mm$^2$ to about 8 mm$^2$, about 0.5 mm$^2$ to about 3 mm$^2$, about 0.5 mm$^2$ to about 4 mm$^2$, about 0.5 mm$^2$ to about 5 mm$^2$, about 0.7 mm$^2$ to about 6 mm$^2$, about 0.7 mm$^2$ to about 3 mm$^2$, about 0.8 mm$^2$ to about 2 mm$^2$, about 0.9 mm$^2$ to about 1.4 mm$^2$, about 1 mm$^2$, about 1.1 mm$^2$, about 1.2 mm$^2$, about 1.23 mm$^2$, about 1.3 mm$^2$, or about 1.4 mm$^2$, specifically reciting all 0.1 mm$^2$ increments within the above-specified ranges and all ranges formed therein or thereby. The effective aperture area of the apertures is measured according to the Aperture Test described herein.

A majority of, or all of, the apertures 422 may have a feret (length of aperture) in the range of about 0.5 mm to about 4 mm, about 0.8 mm to about 3 mm, about 1 mm to about 2 mm, about 1.2 mm to about 1.8 mm, about 1.4 mm to about 1.6 mm, about 1.49, or about 1.5 mm specifically reciting all 0.1 mm increments within the above-specified ranges and all ranges formed therein or thereby. The aperture feret is measured according to the Aperture Test described herein.

A majority of, or all of, the apertures 422 may have a minimum feret (width of aperture) in the range of about 0.5 mm to about 4 mm, about 0.7 mm to about 3 mm, about 0.8 mm to about 2 mm, about 0.9 mm to about 1.3 mm, about 1 mm to about 1.2 mm, about 1 mm, about 1.1 mm, about 1.11 mm, about 1.2 mm, or about 1.3 mm, specifically reciting all 0.1 mm increments within the above-specified ranges and all ranges formed therein or thereby. The aperture minimum feret is measured according to the Aperture Test described herein.

A majority of, or all of, the apertures 422 may have a feret to minimum feret ratio in the range of about 0.3 to about 2.5, about 0.5 to about 2, about 0.8 to about 1.6, about 1 to about 1.5, about 1.1 to about 1.5, about 1.2, about 1.3, about 1.35, about 1.4, or about 1.5, specifically reciting all 0.1 increments within the above-specified ranges and all ranges formed therein or thereby. The feret ratio is calculated by dividing the aperture feret by the aperture minimum feret.

The average lateral axis center-to-center aperture spacing of a majority of, or all of, adjacent apertures, measuring across a projection, is in the range of about 2 mm to about 20 mm, about 2 mm to about 15 mm, about 3 mm to about 12 mm, about 3 mm to about 10 mm, about 3 mm to about 8 mm, about 3 mm to about 7 mm, about 4 mm, about 5 mm, about 6 mm, about 7 mm, about 4 mm to about 6 mm, about 5 mm to about 6 mm, about 4.8 mm, about 4.9 mm, about 5.0 mm, about 5.1 mm, about 5.2 mm, about 5.3 mm, about 5.4 mm, about 5.5 mm, about 5.6 mm, about 5.7 mm, about 5.8 mm, or about 5.9 mm, specifically reciting all 0.1 mm increments within the above-specified ranges and all ranges formed therein or thereby. The average lateral axis center-to-center spacing of adjacent apertures is measured according to the Average Aperture Spacing Test (Lateral Axis Aperture Spacing) described herein.

The average longitudinal axis center-to-center aperture spacing of a majority of, or all of, adjacent apertures, measuring across a projection, is in the range of about 2 mm to about 20 mm, about 2 mm to about 15 mm, about 3 mm to about 12 mm, about 3 mm to about 10 mm, about 3 mm to about 8 mm, about 3 mm to about 7 mm, about 4 mm, about 5 mm, about 6 mm, about 7 mm, about 4 mm to about 6 mm, about 5 mm to about 6 mm, about 4.8 mm, about 4.9 mm, about 5.0 mm, about 5.1 mm, about 5.2 mm, about 5.3 mm, about 5.4 mm, about 5.5 mm, about 5.6 mm, about 5.7 mm, about 5.8 mm, or about 5.9 mm, specifically reciting all 0.1 mm increments within the above-specified ranges and all ranges formed therein or thereby. The average longitudinal axis center-to-center spacing of adjacent apertures is measured according to the Average Aperture Spacing Test (Longitudinal Axis Aperture Spacing) described herein.

A majority of, or all of, the projections 416 may have a widest cross-sectional diameter, taken in a direction parallel to the lateral axis of the absorbent article, in the range of about 1, to about 15 mm, about 1 mm to about 10 mm, about 1 mm to about 8 mm, about 1 mm to about 6 mm, about 1.5 mm to about 6 mm, about 2 mm to about 5 mm, specifically reciting all 0.1 mm increments within the above-specified ranges and all ranges formed therein or thereby.

A majority of, or all of, the projections 416 may have a widest cross-sectional diameter, taken in a direction parallel to the longitudinal axis of the absorbent article, in the range of about 1 mm to about 15 mm, about 1 mm to about 10 mm, about 1 mm to about 8 mm, about 1 mm to about 6 mm, about 1.5 mm to about 6 mm, about 2 mm to about 5 mm, specifically reciting all 0.1 mm increments within the above-specified ranges and all ranges formed therein or thereby.

The substrates or topsheets of the present disclosure may have a % effective open area in the range of about 1% to about 50%, about 1% to about 40%, about 3% to about 35%, about 5% to about 25%, about 5% to about 20%, about 6% to about 18%, about 5% to about 15%, about 5% to about 8%, about 9%, about 9.5%, about 10%, about 10.5%, about 11%, or about 12%, specifically reciting all 0.1% increments within the above-specified ranges and all ranges formed therein or thereby. The % effective open area of the substrates is measured according to the Aperture Test described herein.

The substrates or topsheets of the present disclosure may have apertures having a perimeter in the range of about 1 mm to about 50 mm, about 1 mm to about 30 mm, about 2 mm to about 20 mm, about 2 mm to about 15 mm, about 2 mm to about 10 mm, about 3 mm to about 8 mm, about 4 mm, about 5 mm, about 5.42 mm, about 6 mm, or about 7 mm, specifically reciting all 0.1 mm increments within the above-specified ranges and all ranges formed therein or thereby. The perimeter of the apertures is measured according to the Aperture Test described herein.

The first side 418 of the substrates 400 of the present disclosure may have geometric roughness value in the range of about 2 to about 4.5, about 2.5 to about 4, about 3 to about 4, about 3.1 to about 3.5, about 3.2 to about 3.3, about 3.31, about 3.35, about 3.4, or about 3.5, specifically reciting all 0.1 increments within the above-specified ranges and all ranges formed therein or thereby. The geometric roughness values of the first side 418 of the substrates 400 of the present disclosure are measured according to the Descriptive Analysis Roughness Test described herein. The first side 418 of the substrates 400 of the present disclosure may have a coefficient of friction value in the range of about 0.2 to about 0.4, about 0.25 to about 0.35, about 0.27 to about 0.31, about 0.27, about 0.28, about 0.29, about 0.30, or about 0.31, specifically reciting all 0.01 increments within the above-specified ranges and all ranges formed therein or thereby. The coefficient of friction values of the first side 418 of the substrates 400 of the present disclosure are measured according to the Descriptive Analysis Roughness Test described herein. The first side 418 of the substrates 400 of the present disclosure may have a slip stick value in the range of about 0.010 to about 0.025, about 0.015 to about 0.020, about 0.015, about 0.016, about 0.017, about 0.018, or about 0.019, specifically reciting all 0.001 increments within the above-specified ranges and all ranges formed therein or thereby. The coefficient of friction values of the first side 418 of the substrates 400 of the present disclosure are measured according to the Descriptive Analysis Roughness Test described herein.

The second side 420 of the substrates 400 of the present disclosure may have geometric roughness value in the range of about 2 to about 4.0, about 2.3 to about 3.5, about 2.5 to about 3.3, about 2.6 to about 3.1, about 2.6, about 2.7, about 2.8, about 2.83, about 2.9, or about 3.0, specifically reciting all 0.1 increments within the above-specified ranges and all ranges formed therein or thereby. The geometric roughness values of the second side 420 of the substrates 400 of the present disclosure are measured according to the Descriptive Analysis Roughness Test described herein. The second side 420 of the substrates 400 of the present disclosure may have a coefficient of friction value in the range of about 0.2 to about 0.4, about 0.25 to about 0.35, about 0.27 to about 0.31, about 0.27, about 0.28, about 0.29, about 0.30, or about 0.31, specifically reciting all 0.01 increments within the above-specified ranges and all ranges formed therein or thereby. The coefficient of friction values of the second side 420 of the substrates 400 of the present disclosure are measured according to the Descriptive Analysis Roughness Test described herein. The second side 420 of the substrates 400 of the present disclosure may have a slip stick value in the range of about 0.010 to about 0.025, about 0.011 to about 0.018, about 0.012, about 0.013, about 0.014, about 0.015, or about 0.016, specifically reciting all 0.001 increments within the above-specified ranges and all ranges formed therein or thereby. The coefficient of friction values of the second side 420 of the substrates 400 of the present disclosure are measured according to the Descriptive Analysis Roughness Test described herein.

Ratios

The ratio of the height of the projections (μm) to the % effective open area may be in the range of about 70 to about 160, about 80 to about 150, about 100 to about 145, about 95 to about 150, about 100 to about 140, about 110 to about 130, about 115 to about 130, about 118 to about 125, about 120, about 121, about 122, about 122.74, about 123, or about 124, specifically reciting all 0.1 increments within the specified ranges and all ranges formed therein or thereby.

The ratio of the overall substrate height (μm) to the % effective open area may be in the range of about 125 to about 350, about 150 to about 300, about 175 to about 275, about 200 to about 250, about 215 to about 235, about 220 to about 230, or about 225, specifically reciting all 0.1 increments within the specified ranges and all ranges formed therein or thereby.

The ratio of the height of the projections (μm) to the geometric roughness of a surface (e.g., first or second; 418 or 420) of the three-dimensional substrates may be in the range of about 250 to about 600, about 300 to about 500, about 325 to about 450, about 325 to about 425, about 350, about 352, about 410, or about 412, specifically reciting all 0.1 increments within the specified ranges and all ranges formed therein or thereby.

The ratio of the overall substrate height (μm) to the geometric roughness of a surface (e.g., first or second; 418 or 420) of the three-dimensional substrates may be in the range of about 500 to about 900, about 600 to about 800, about 645, about 650, about 700, about 750 m, or about 755, specifically reciting all 0.1 increments within the specified ranges and all ranges formed therein or thereby.

The substrates or topsheets of the present disclosure may comprise one or more colors, dyes, inks, indicias, patterns, embossments, and/or graphics. The colors, dyes, inks, indicias, patterns, and/or graphics may aid the aesthetic appearance of the substrates.

The substrates of the present disclosure may be used as a portion of, or all of, any suitable products, such as dusters, wipes (wet or dry), makeup removal substrates, paper towels, toilet tissue, facial tissue, medical gowns, surgical substrates, wraps, filtration substrates, or any other suitable products.

EXAMPLES

TABLE 2

| Product | P&G--Greater China (Flat Topsheet) | Kao Greater China and Japan (Three Dimesional Topsheet) | Present Disclosure | P&G Greater China and Japan (Apertured Topsheet) |
|---|---|---|---|---|
| Brand Name | Pampers Premium Care | Merries | NA | Pampers Premium Care (Japan import) |
| Product Acquisition Date from Market | July 2015 | 2012 | | March 2016 |
| ModifiedFluid Acquisition Test (seconds) | 126.8 sec | 518.9 sec | 119.8 sec | 191.1 sec |
| Collagen Rewet (mg) | 74 mg | 121 mg | 62 mg | 42 (10) mg |
| Light Touch Dryness (mg) | 102 mg | 25 mg | 35 mg | N/A |

As can been seen in Table 2 above, three commercially available products were tested and compared to the absorbent articles of the present disclosure. All of the absorbent articles tested were size 2. The absorbent articles of the present disclosure achieved the fastest modified fluid acquisition test, a decent collagen rewet, and a low light touch dryness ("LTD") (i.e., dryness of the topsheet). The methods for Modified Fluid Acquisition Test, Collagen Rewet, and Light Touch Dryness are set forth below.

Method of Making the Three-Dimensional Substrates or Absorbent Articles Comprising the Three-Dimensional Substrates The three-dimensional substrates and absorbent articles comprising three-dimensional substrates of the present disclosure may be made by any suitable methods known in the art. In particular, the articles may be hand-made or industrially produced at high speed.

Figure 26:
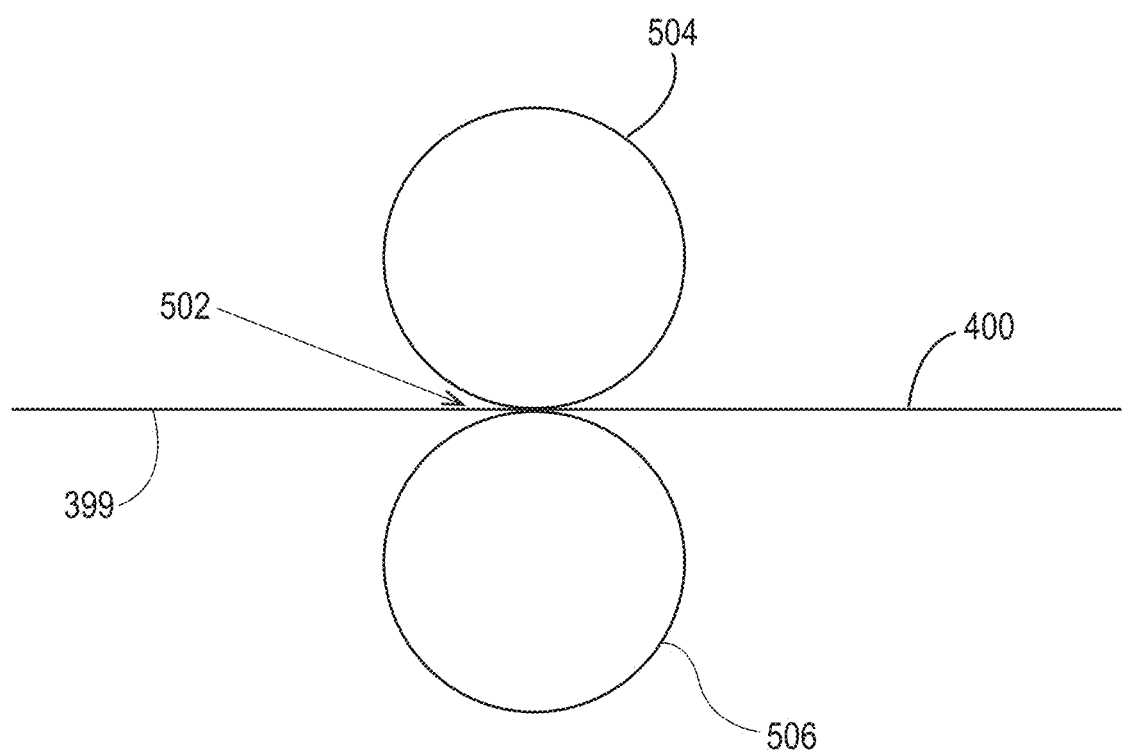
FIG. 26 is a schematic illustration of one example process for forming the substrates of the present disclosure.
Figure 27:
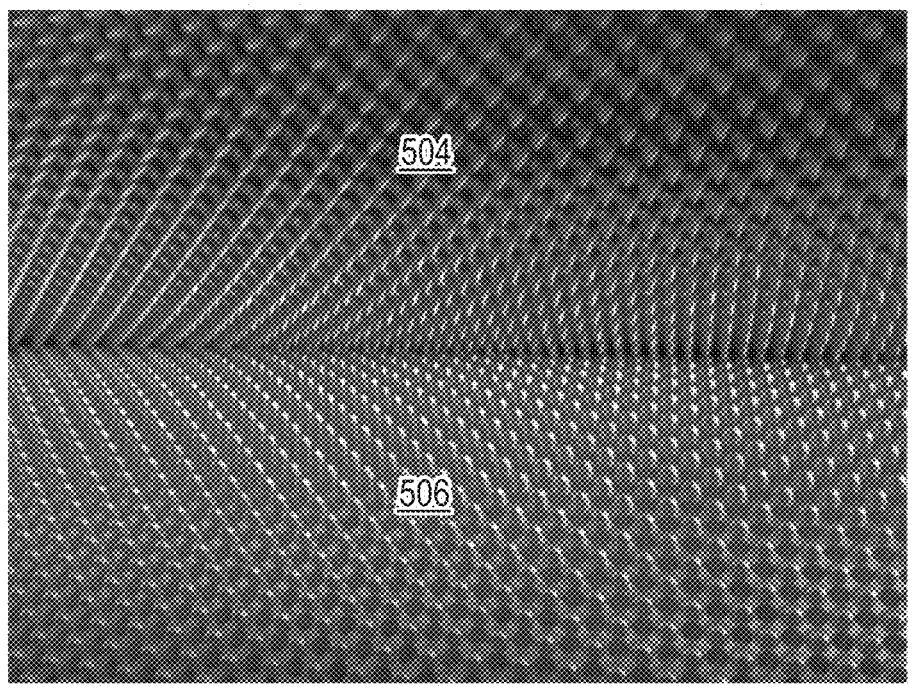
FIG. 27 is a view of intermeshing engagement of portions of first and second rolls in accordance with the present disclosure.
Figure 28:
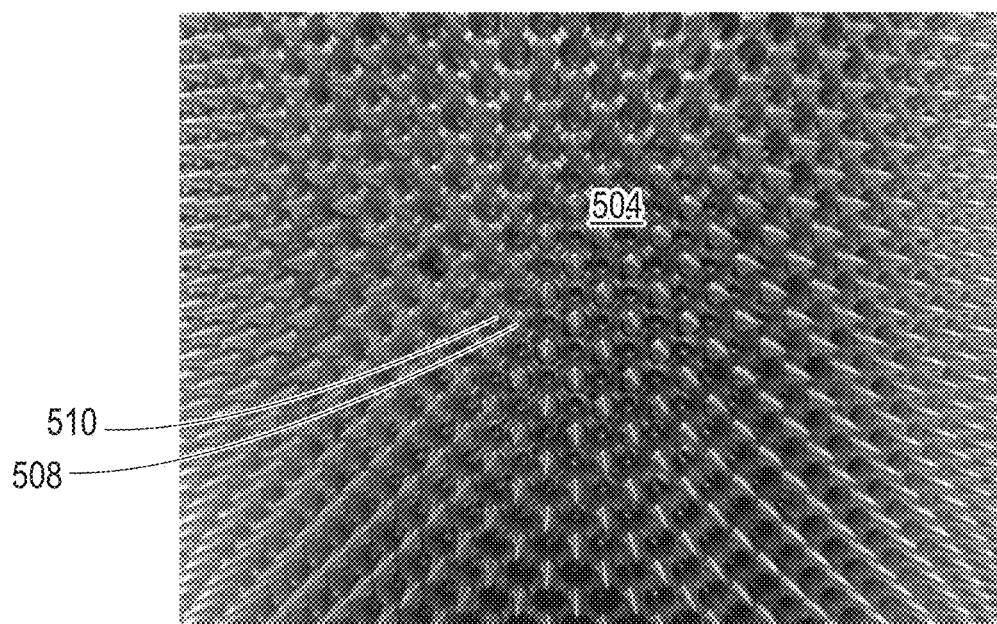
FIG. 28 is a view of a portion of the first roll in accordance with the present disclosure.
Figure 29:
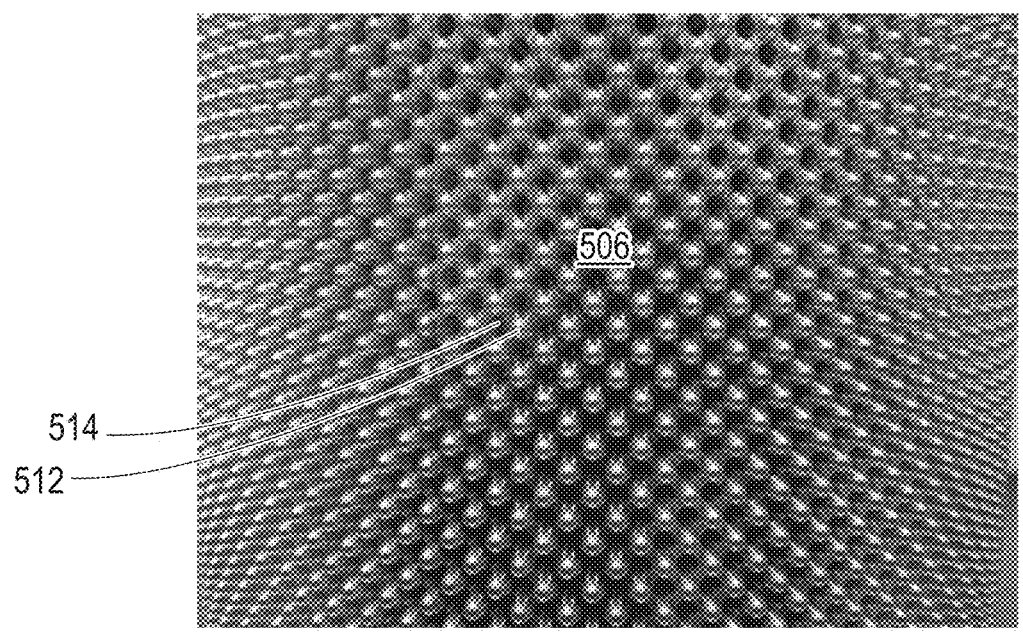
FIG. 29 is a view of a portion of the second roll in accordance with the present disclosure.

FIG. 26 is a schematic illustration of one example process for forming the substrates of the present disclosure. FIG. 27 is a view of intermeshing engagement of portions of first and second rolls. FIG. 28 is a view of a portion of the first roll. FIG. 29 is a view of a portion of the second roll.

Referring to FIGS. 26-29, the substrates of the present disclosure may be formed by passing a one or more layer substrate 399 (non-three dimensional) through a nip 502 formed by two intermeshing rolls 504 and 506 to form a three-dimensional substrate 400. The rolls 504 and 506 may be heated. A first roll 504 may create the apertures 422 and the recesses 414 in the substrate 400 (in combination with the second roll) and a second roll 506 may create the projections 416 in the substrate 400 (in combination with the first roll). The first roll 504 may comprise a plurality of conically-shaped protrusions 508 extending radially outwardly from the first roll 504. The first roll 504 may also comprise a plurality of recesses 510 formed in a radial outer surface of the first roll 504. The second roll 506 may comprise a plurality of dome-shaped protrusions 512 extending radially outwardly from the second roll 506. The second roll 506 may also comprise a plurality of recesses 514 formed in the radial outer surface of the second roll 506. The protrusions 508 on the first roll 504 may have a different size, shape, height, area, width and/or dimension than the protrusions 512 on the second roll 506. The recesses 510 formed in the first roll 504 may have a different size, shape, height, area, width, and/or dimension than the recesses 514 formed in the second roll 506. The recesses 510 in the first roll 504 may be configured to at least partially receive the dome-shaped protrusions 512, thereby creating the projections 414 in the substrate 400. The recesses 510 may be deep enough so that the portions of the substrate forming the projections 414 and projection peaks 425 will not be compressed, or sufficiently compressed. Specifically, as the dome-shaped protrusions 512 engage into the recesses 510, there is sufficient depth left in the space between the surfaces in a radial direction so that the thickness of the substrate in the projections 414 is higher than the thickness of the recesses 510. This feature provides projections 414 with a softer feel and a greater height compared to compressing the portions of the substrate forming the projections. The recesses 514 in the second roll 506 may be configured to at least partially receive the conically-shaped protrusions 508 thereby creating the recesses 414 and the apertures 422 in the substrate 400.

The substrates of the present disclosure may also be formed by any other suitable methods known to those of skill in the art.

The Topsheet Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 30:
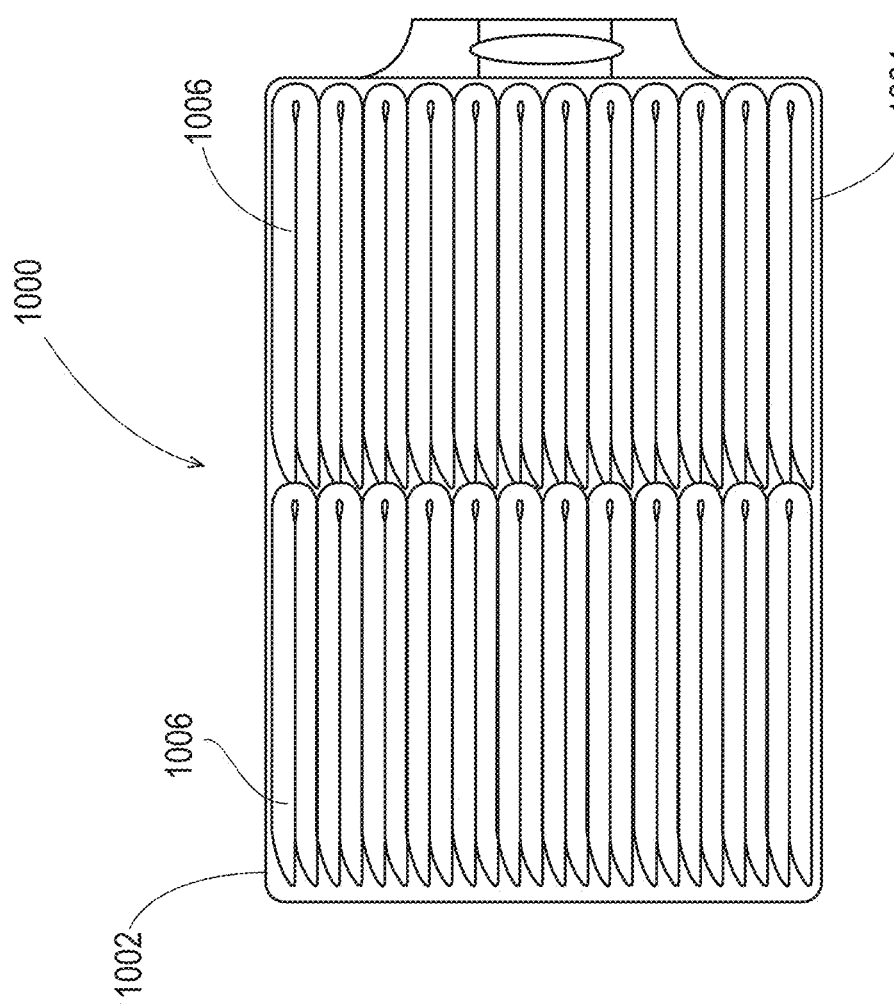
FIG. 30 is a side view of a package of absorbent articles in accordance with the present disclosure. The outer surface is illustrated as transparent for purposes of clarity.

FIG. 30 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Test Methods

Condition all samples at about 23° C.±2 C.° and about 50%±2% relative humidity for 2 hours prior to testing.

Aperture Test

Aperture dimensions, effective aperture area, and % effective open area measurements are performed on images generated using a flat-bed scanner capable of scanning in reflectance mode at a resolution of 6400 dpi and 8 bit grayscale (a suitable scanner is the Epson Perfection V750 Pro, Epson, USA). Analyses are performed using ImageJ software (v.s 1.46, National Institute of Health, USA) and calibrated against a ruler certified by NIST. A steel frame (100 mm square, 1.5 mm thick with an opening 60 mm square) is used to mount the specimen and a black glass tile (P/N 11-0050-30, available from HunterLab, Reston, Va.) is used as the background for the scanned images.

Take the steel frame and place double-sided adhesive tape on the bottom surface surrounding the interior opening. To obtain a specimen, lay the absorbent article flat on a lab bench with the wearer-facing surface directed upward. Remove the release paper of the tape, and adhere the steel frame to the topsheet (substrates described herein may only form a portion of the topsheet, e.g., by being positioned on the topsheet—the three-dimensional material is what is sampled) of the absorbent article. Using a razor blade, excise the top sheet from the underling layers of the absorbent article around the outer perimeter of the frame. Carefully remove the specimen such that its longitudinal and lateral extension is maintained. A cryogenic spray (such as Cyto-Freeze, Control Company, Houston Tex.) can be used to remove the topsheet specimen from the underling layers, if necessary. Five replicates obtained from five substantially similar absorbent articles are prepared for analysis.

Place the ruler on the scanner bed, close the lid and acquire a 50 mm by 50 mm calibration image of the ruler in reflectance mode at a resolution of 6400 dpi and 8 bit grayscale. Save the image as an uncompressed TIFF format file. Lift the lid and remove the ruler. After obtaining the calibration image, all specimens are scanned under the same conditions and measured based on the same calibration file. Next, place the framed specimen onto the center of the scanner bed with the wearer-facing surface of the specimen facing the scanner's glass surface. Place the black glass tile on top of the frame covering the specimen, close the lid and acquire a scanned image. In like fashion scan the remaining four replicates.

Open the calibration file in ImageJ and perform a linear calibration using the imaged ruler, with the scale set to Global so that the calibration will be applied to subsequent specimens. Open a specimen image in ImageJ. View the histogram and identify the gray level value for the minimum population located between the dark pixel peak of the holes and the lighter pixel peak of the nonwoven. Threshold the image at the minimum gray level value to generate a binary image. In the processed image, the apertures appear as black and nonwoven as white.

Select the analyze particles function. Set the minimum aperture area exclusion limit to 0.3 mm$^2$ and for the analysis to exclude the edge apertures. Set the software to calculate: effective aperture area, perimeter, feret (length of the aperture) and minimum feret (width of the aperture). Record the average effective aperture area to the nearest 0.01 mm$^2$, and the average perimeter to the nearest 0.01 mm. Again select the analyze particles function, but his time set the analysis to include the edge holes as it calculates the effective aperture areas. Sum the effective aperture areas (includes whole and partial apertures) and divide by the total area included in the image (2500 mm$^2$). Record as the % effective open area to the nearest 0.01%.

In like fashion analyze the remaining four specimen images. Calculate and report the average effective aperture area to the nearest 0.01 mm$^2$, the average aperture perimeter to the nearest 0.01 mm, feret and minimum feret to the nearest 0.01 mm, and the % effective open area to the nearest 0.01% for the five replicates.

Height Tests

Substrate projection heights and overall substrate heights are measured using a GFM MikroCAD Premium instrument commercially available from GFMesstechnik GmbH, Teltow/Berlin, Germany. The GFM MikroCAD Premium instrument includes the following main components: a) a DLP projector with direct digital controlled micro-mirrors; b) a CCD camera with at least a 1600×1200 pixel resolution; c) projection optics adapted to a measuring area of at least 60 mm×45 mm; d) recording optics adapted to a measuring area of at least 60 mm×45 mm; e) a table tripod based on a small hard stone plate; f) a blue LED light source; g) a measuring, control, and evaluation computer running ODSCAD software (version 6.2, or equivalent); and h) calibration plates for lateral (x-y) and vertical (z) calibration available from the vendor.

The GFM MikroCAD Premium system measures the surface height of a sample using the digital micro-mirror pattern fringe projection technique. The result of the analysis is a map of surface height (z-directional or z-axis) versus displacement in the x-y plane. The system has a field of view of 60×45 mm with an x-y pixel resolution of approximately 40 microns. The height resolution is set at 0.5 micron/count, with a height range of +/−15 mm. All testing is performed in a conditioned room maintained at about 23±2° C. and about 50±2% relative humidity.

A steel frame (100 mm square, 1.5 mm thick with an opening 70 mm square) is used to mount the specimen. Take the steel frame and place double-sided adhesive tape on the bottom surface surrounding the interior opening. To obtain a specimen, lay the absorbent article flat on a bench with the wearer-facing surface directed upward. Remove the release paper of the tape, and adhere the steel frame to the topsheet (substrates described herein may only form a portion of the topsheet, e.g., by being positioned on the topsheet—the three-dimensional material is what is sampled) of the absorbent article. Using a razor blade, excise the topsheet from the underling layers of the absorbent article around the outer perimeter of the frame. Carefully remove the specimen such that its longitudinal and lateral extension is maintained. A cryogenic spray (such as Cyto-Freeze, Control Company, Houston Tex.) can be used to remove the topsheet specimen from the underling layers, if necessary. Five replicates obtained from five substantially similar absorbent articles are prepared for analysis.

Calibrate the instrument according to manufacturer's specifications using the calibration plates for lateral (x-y axis) and vertical (z axis) available from the vendor.

Place the steel plate and specimen on the table beneath the camera, with the wearer-facing surface oriented toward the camera. Center the specimen within the camera field of view, so that only the specimen surface is visible in the image. Allow the specimen to lay flat with minimal wrinkles.

Collect a height image (z-direction) of the specimen by following the instrument manufacturer's recommended measurement procedures. Select the Technical Surface/Standard measurement program with the following operating parameters: Utilization of fast picture recording with a 3 frame delay. Dual phaseshifts are used with 1) 16 pixel stripe width with a picture count of 12 and 2) 32 pixel stripe width with a picture count of 8. A full Graycode starting with pixel 2 and ending with pixel 512. After selection of the measurement program, continue to follow the instrument manufacturer's recommended procedures for focusing the measurement system and performing the brightness adjustment. Perform the 3D measurement then save the height image and camera image files.

Load the height image into the analysis portion of the software via the clipboard. The following filtering procedure is then performed on each image: 1) removal of invalid points; 2) removal of peaks (small localized elevations); 3) polynomial filtering of the material part with a rank of n=5, with exclusion of 30% of the peaks and 30% of the valleys from the material part, and 5 cycles.

Projection Height Test

Draw a line connecting the peaks of a series of projections, with the line crossing a non-apertured land area located between each of the projections. Generate a sectional image of the height image along the drawn line. Along the sectional line, measure the vertical height (z-direction) difference between the peak of the projection and the adjacent valley of the land area. Record the height to the nearest 0.1 µm. Average together 10 different projection peak to land area height measures and report this value to the nearest 0.1 µm. This is the projection height.

Recess Height Test

Subtract the projection height from the overall substrate height to obtain the recess height. This should be done with each of the ten measurements from the Projection Height Test and the Overall Substrate Height Test. Average together the ten recess heights and report this value to the nearest 0.1 µm. This is the recess height.

Overall Substrate Height Test

Draw a line connecting the peaks of a series of projections, with the line crossing the center of an aperture located between each of the projections and within a recess. Generate a sectional image of the height image along the drawn line. Along the sectional line, measure the vertical height difference between the peak of the projection and the adjacent base of the recess. Record the height to the nearest 0.1 µm. Average together 10 different projection peak to base of recess height measures and report this value to the nearest 0.1 µm. This is the overall substrate height.

Average Aperture Spacing Test

Lateral Axis Aperture Spacing and Longitudinal Axis Aperture Spacing are performed on images generated using a flatbed scanner capable of scanning in reflectance mode at a resolution of 6400 dpi and 8 bit grayscale (a suitable scanner is the Epson Perfection V750 Pro, Epson, USA). Analyses are performed using ImageJ software (v.s 1.46, National Institute of Health, USA) and calibrated against a ruler certified by NIST. A steel frame (100 mm square, 1.5 mm thick with an opening 60 mm square) is used to mount the specimen and a black glass tile (P/N 11-0050-30, available from HunterLab, Reston, Va.) is used as the background for the scanned images. Testing is performed at about 23° C.±2 C.° and about 50%±2% relative humidity.

Take the steel frame and place double-sided adhesive tape on the bottom surface surrounding the interior opening. To obtain a specimen, lay the absorbent article flat on a lab bench with the wearer-facing surface directed upward. Remove the release paper of the tape, and adhere the steel frame to the topsheet of the absorbent article. Using a razor blade excise the topsheet (i.e., the three dimensional substrate that forms all of or part of the wearer-facing surface) from the underling layers of the absorbent article around the outer perimeter of the frame. Carefully remove the specimen such that its longitudinal and lateral extension is maintained. A cryogenic spray (such as Cyto-Freeze, Control Company, Houston Tex.) can be used to remove the topsheet specimen from the underling layers, if necessary. Five replicates obtained from five substantially similar absorbent articles are prepared for analysis. Condition the samples at about 23° C.±2 C.° and about 50%±2% relative humidity for 2 hours prior to testing.

Place the ruler on the scanner bed, close the lid and acquire a 50 mm by 50 mm calibration image of the ruler in reflectance mode at a resolution of 6400 dpi and 8 bit grayscale. Save the image as an uncompressed TIFF format file. Lift the lid and remove the ruler. After obtaining the calibration image, all specimens are scanned under the same conditions and measured based on the same calibration file. Next, place the framed specimen onto the center of the scanner bed with the wearer-facing surface of the specimen facing the scanner's glass surface. Place the black glass tile on top of the frame covering the specimen, close the lid and acquire a scanned image. In a like fashion, scan the remaining four replicates.

Open the calibration file in ImageJ and perform a linear calibration using the imaged ruler, with the scale set to Global so that the calibration will be applied to subsequent specimens. Open a specimen image in ImageJ and perform the following measures:

Lateral Axis Aperture Spacing

Measure from a center point of one aperture to a center point of an adjacent aperture on the other side of a projection, wherein the projection is positioned between the two apertures. The measurement will be taken in a direction parallel to a lateral axis of the specimen across the projection. Report each distance to the nearest 0.1 mm. Take 5 random measurements in the specimen. Average the five values to and report the average lateral axis center to center spacing to the nearest 0.1 mm. Repeat this procedure for the additional four samples.

Longitudinal Axis Aperture Spacing

Measure from a center point of one aperture to a center point of an adjacent aperture on the other side of a projection, wherein the projection is positioned between the two apertures. The measurement will be taken in a direction parallel to a longitudinal axis of the specimen across the projection. Report each distance to the nearest 0.1 mm. Take 5 random measurements in the specimen. Average the five values to and report the average longitudinal axis center to center spacing to the nearest 0.1 mm. Repeat this procedure for the additional four samples.

Basis Weight Test

Basis weight of the three-dimensional substrates may be determined by several available techniques but a simple representative technique involves taking an absorbent article, removing any elastic which may be present and stretching the absorbent article to its full length. A punch die having an area of 45.6 cm$^2$ is then used to cut a piece of the substrate forming a topsheet, positioned on the topsheet, or forming a portion of the topsheet (the "topsheet" in this method), from the approximate center of the diaper or absorbent product in a location which avoids to the greatest extent possible any adhesive which may be used to fasten the topsheet to any other layers which may be present and removing the topsheet layer from other layers (using cryogenic spray, such as Cyto-Freeze, Control Company, Houston, Tex. if needed). The sample is then weighed and dividing by the area of the punch die yields the basis weight of the topsheet. Results are reported as a mean of 5 samples to the nearest 0.1 gram per square meter.

Descriptive Analysis Roughness Method

Surface Geometrical Roughness is measured using a Kawabata Evaluation System KES FB4 Friction tester with Roughness Sensor (available from Kato Tech Co., Japan). The instrument measures both surface friction and geometric roughness simultaneously, but herein only the geometric roughness (SMD value) is reported. All testing is performed at about 23° C.±2 C.° and about 50%±2% relative humidity. Samples are preconditioned at about 23° C.±2 C.° and about 50%±2% relative humidity for 2 hours prior to testing. The instrument is calibrated as per the manufacturer's instructions.

The absorbent article is placed, wearer-facing surface upward, onto a lab bench. The absorbent article's cuffs are clipped with scissors to facilitate the article lying flat. With scissors or a scalpel excise a specimen of the topsheet 20 cm long in the longitudinal direction of the absorbent article and 10 cm wide in the lateral direction of the absorbent article. Care should be taken in removing the specimen as to not distort the dimensions in either the longitudinal or lateral direction. Specimens are collected from a total of five substantially identical absorbent articles.

Turn on the KES FB4. The instrument should be allowed to warm up for at least 10 minutes before use. Set the instrument to a SMD sensitivity of 2×5, a testing velocity of 0.1, and a compression area of 2 cm. The roughness contractor compression (contact force) is adjusted to 10 gf. Place the topsheet specimen on the tester with the wearer-facing surface facing upward and the longitudinal dimension aligned with the test direction of the instrument. Clamp the specimen with an initial tension of 20 gf/cm. Initiate the test. The instrument will automatically take 3 measurements on the specimen. Record the MIU (Coefficient of Friction), MMD (Slip Stick), and SMD (Geometrical Roughness) value from each of the three measurements to the nearest 0.001 micron. Repeat in like fashion for the remaining four specimens.

Report Coefficient of Friction as an average of the 15 recorded values to the nearest 0.01. Report Slip Stick as an average of the 15 recorded values to the nearest 0.001. Report the Geometrical Roughness as an average of the 15 recorded values to the nearest 0.01 micron.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 30). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Thickness Test

The thickness of the material sample is measured using a dial gauge or digital equivalent with a resolution of ±°10 μm and a circular "foot" having a flat bottom circular surface with a diameter of 56 mm. The gauge is mounted over a base having a horizontal flat rigid upper surface, such that the entire bottom surface of the foot contacts the upper surface of the base.

The downward force exerted by the foot on the base or on a material sample inserted between the foot and the base is depending on the weight of the foot, i.e. depending on the exact equipment used.

The weight exerted by the foot of the gauge can be measured by mounting the gauge over a suitable top-loading balance such that the balance pan is in the same relative position to the gauge as the base. It is independent of the thickness of the material sample. The force is adjusted by adding weight to the foot such that the total weight is 518 g, i.e. the pressure exerted by the foot of 56 mm diameter is 2065±10 Pa.

The gauge is calibrated according to the manufacturer's instructions.

The material sample is cut from a respective topsheet or acquisition layer precursor material as a circle of 6 cm diameter. Such material sample is placed on the base such that the foot is completely in contact with the material sample.

The thickness of the material sample is determined by reading the gauge with the foot resting on the base (G0). The foot of the gauge is then raised and the material sample is laid flat on the base. The foot is lowered gently onto the material sample and the gauge reading is taken 5 seconds after that the foot comes into contact with the material sample (GT). The thickness of the material sample at that location is the difference between the two readings (GT−G0). The thickness is the average of three replicates and is reported in millimeters rounded to the nearest 0.01 mm.

Capillary Sorption Test

The phenomenon of capillary sorption is well recognized. See A. A. Burgeni and C. Kapur, "Capillary Sorption Equilibria in Fiber Masses," Textile Research Journal, 37 (1967), pp. 356-366, and P. K. Chatterjee, Absorbency, Textile Science and Technology Vol. 7, Chapter II, "Mechanism of Liquid Flow and Structure Property Relationships", pp. 29-84, Elsevier Science Publishers B.V., 1985 for a discussion of capillary sorption of absorbent structures.

A porous glass frit is connected via an uninterrupted column of fluid to a fluid reservoir, monitored on a balance. The test fluid is degassed 0.9% saline. The sample, mounted on the porous glass frit, is maintained under constant confining pressure during the experiment. As the porous structure absorbs/desorbs fluid, the weight of the balance reservoir is recorded. The data are used to determine equilibrium capacity as a function of capillary suction height. Absorption occurs during the incremental lowering of the frit (i.e. decreasing capillary suction height). Desorption occurs during the incremental raising of the frit (i.e., increasing capillary suction height). The data are corrected for the capillary sorption of the porous frit and for evaporation of fluid during the experiment.

Figure 31:
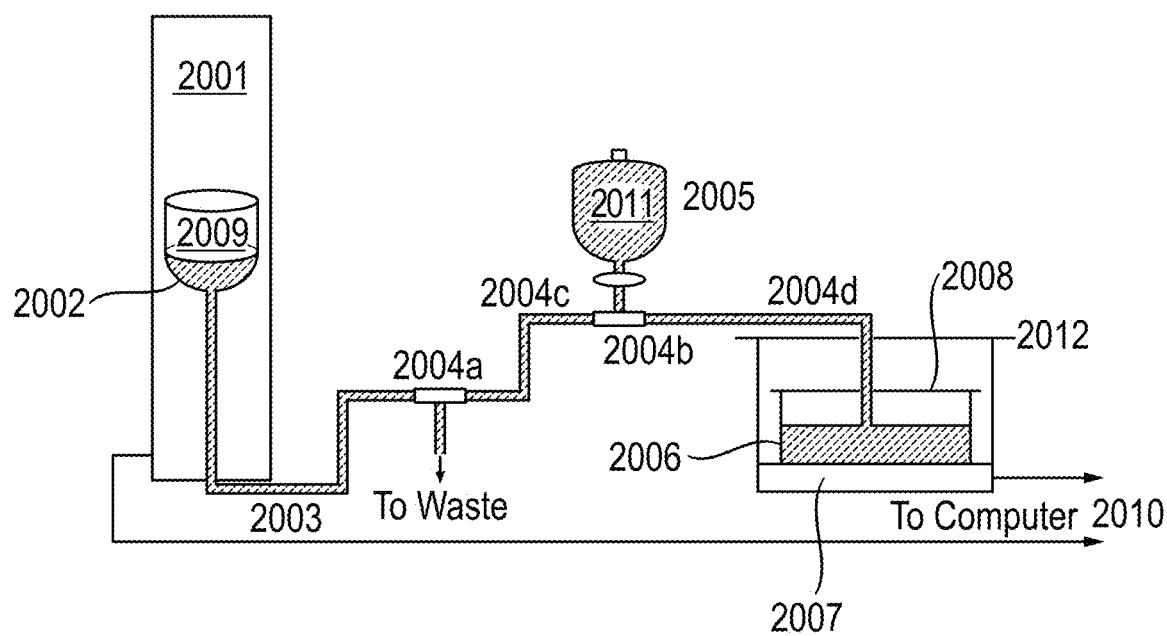
FIG. 31 illustrates an equipment assembly used in the Capillary Sorption Test.

The capillary sorption equipment, as shown in FIG. 31, is set up and operated under lab conditions (23±2° C., 50±5% RH). The sample is placed in a movable sample assembly 2002 that is connected hydraulically to a fluid reservoir 2006 that rests on a balance 2007. The balance 2007 should read to within ±0.001 g and be capable of being interfaced to a computer system 2010 for collection of data. A suitable balance is available from Mettler Toledo as PR1203. The specific fluid path of the system is as follows: The bottom of the sample assembly 2002 is connected to a three-way glass stopcock 2004a via Tygon® tubing 2003. The stopcock 2004a is connected either to drain or via glass tubing 2004c to a second three-way glass stopcock 2004b. This stopcock 2004b switches between a filling reservoir 2005 or the balance reservoir 2006.

The balance reservoir 2006 is a lightweight dish of 11 cm diameter and has a plastic cover 2008. The cover 2008 has a hole in its center through which the glass tubing 2004d contacts the fluid in the balance reservoir 2006. The hole is slightly larger than the outer diameter of the glass tubing 2004d. The glass tubing 2004d must not touch the cover 2008, or the balance reading will be invalid. The balance 2007 and balance reservoir 2006 are further enclosed in a Plexiglas® box 2012 to minimize evaporation of the test fluid from the reservoir 2006 and enhance balance stability during the procedure. The box 2012 has a top and walls, where the top has a hole through which the tubing 2004d is inserted. The hole is as small as practicable in order to minimize evaporation.

Figure 32:
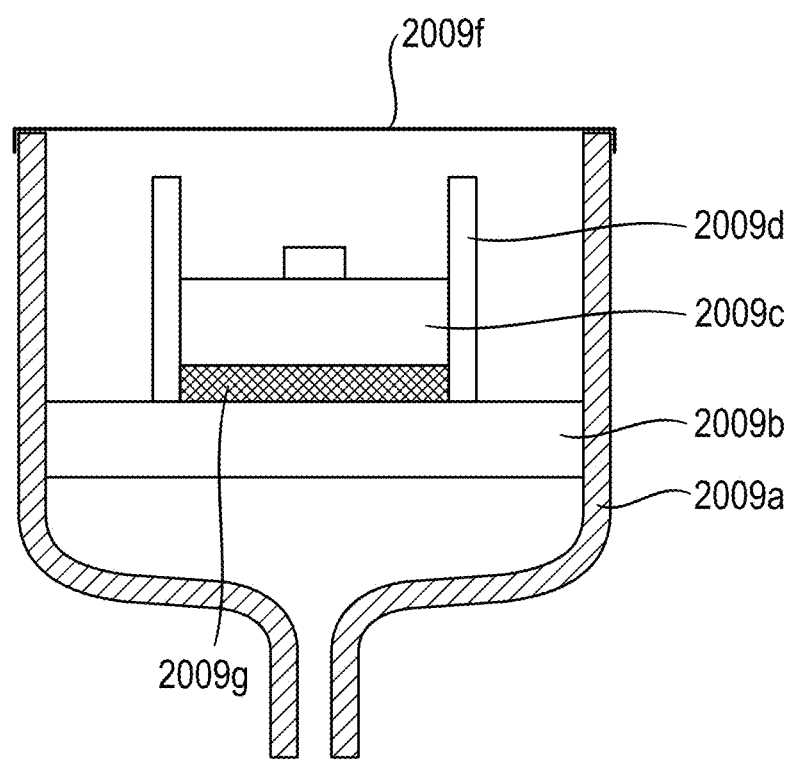
FIG. 32 illustrates an equipment assembly used in the Capillary Sorption Test.
Figure 33:
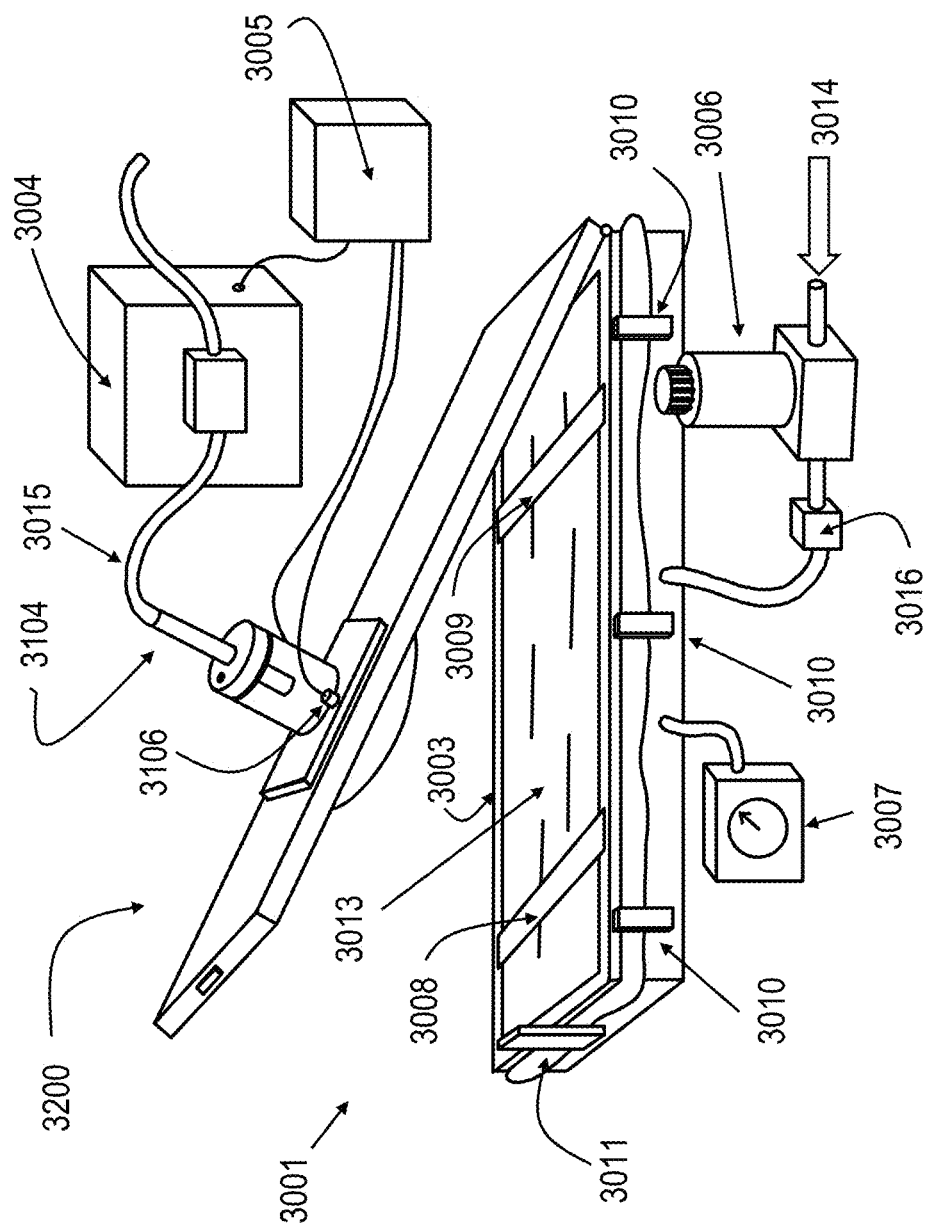
FIG. 33 illustrates an apparatus used in the Modified Fluid Acquisition Test.

As shown in FIG. 32, the sample assembly 2002 comprises a Buchner type funnel 2009a fitted with a glass fritted disc 2009b, and a weight/cylinder apparatus 2009c, 2009d that provides a small confining pressure to a test sample 2009g. The fritted disc funnel 2009a has a capacity of approximately 500 mL with the glass fritted disc 2009b specified as having 10-16 µm pores (available from ROBU VitaPOR® Glasfilter POR4). The pores are fine enough to keep the frit surface wetted at the capillary suction heights specified (i.e., the fritted disc does not allow air to enter the continuous column of test liquid below the frit).

The cylinder apparatus 2009d is fabricated from Lexan® or similar rigid material, and has an outer diameter of 7.0 cm, an inner diameter of 6.0 cm and a height of 6.5 cm. The weight apparatus 2009c applies a pressure of 2.1 Kpa (0.3 psi) and has a diameter of about 0.020 cm less than the inner diameter of cylinder 2009d. To prevent excessive evaporation of test fluid, a lid 2009f covers the fritted disc funnel 2009a. In order to allow for pressure equilibration, lid 2009f should not form an air-tight seal with fritted disc funnel 2009a. This may require a pin-hole or equivalent small opening in the lid.

As shown in FIG. 31, the sample assembly 2002 is mounted on a vertical slide 2001 which is used to adjust the vertical height of the sample. The vertical slide 2001 may be a rodless actuator under computer control. A preferred actuator and motor drive control interface unit is available from Parker Hannifin Corp (5500 Business Park Drive, Rohnert Park, Calif. 94928; as item Compumotor SX83-135).

Data from the balance are collected via computer 2010 throughout the capillary sorption experiment. While the sample is at each capillary suction height, balance readings are taken every 5 seconds. When the change in weight of the balance reservoir 2006 is less than 0.008 g per 5 second interval for 20 consecutive intervals, the system is considered to have reached equilibrium.

A topsheet or an acquisition material is used for the test method. A test specimen for these materials is obtained by punching out a 6 cm diameter circle from the materials, using an arch punch. In most cases, the materials will first have to be separated from an absorbent article using freeze spray.

A test specimen for the distribution material is also obtained from a disposable absorbent article by attaching the absorbent product to a flat surface in a taut planar configuration with the topsheet side facing up. Any leg or cuff elastics are severed in order to allow the absorbent product to lie flat. The midpoint of the longitudinal centerline of the product is marked. Using scissors, two longitudinal cuts are made through all layers above the storage core (i.e. the layer containing more than 20% of superabsorbent polymer by total weight of the absorbent material) along the complete length of the diaper. Two transverse cuts are made though the same layers near the front and back waist edges. The central portion of the topsheet and any other layers above the storage core are then removed without perturbing the structure. Freeze spray (e.g. CRC Freeze Spray manufactured by CRC Industries, Inc. 885 Louis Drive, Warminster, Pa. 18974, USA), or equivalent aid may be used to facilitate removal of the uppermost layers from the absorbent product. The distribution layer is then separated from any other layers using freeze spray if necessary. A test specimen of the distribution layer is obtained by punching out a 6 cm diameter circle from the separated distribution layer centered on the midpoint of the longitudinal centerline of the article, using an arch punch.

After all layers above the absorbent core have been removed, remove the film backsheet and nonwoven outer cover from the core using freeze spray, as needed. A test specimen of the core is obtained by punching out a 6 cm diameter circle from the separated core layer centered on the midpoint of the longitudinal centerline of the article, using an arch punch.

The thickness of the test specimen for the topsheet, for the acquisition layer, for the distribution layer, and for the absorbent core is measured according to the Thickness Test. If the thickness of the test specimen is 0.50 mm or greater, the specimen is tested as-is. If the thickness of the test specimen is less than 0.50 mm, then four additional test specimens are obtained as described above from identical absorbent products, and the five specimens are stacked in the same orientation as they occur in the product. The stack of 5 layers is then used as the test specimen.

In the test method, the term "test sample" refers to test specimen for the topsheet, for the acquisition layer or for the test specimen for the distribution layer.

The Capillary Sorption Test is done on the test specimen for the topsheet, on the test specimen for the acquisition layer, the test specimen for the distribution layer, and the test specimen for the absorbent core.

Experimental Set-Up:
Saline Degassing
1. The water in an ultrasonic water bath (e.g. Bandelin Sonorex Super 10P DK514BP; volume 18.7 L, 325× 300×200 mm) is heated up to 50° C.
2. A 10 L volumetric flask, filled with about 9 L of 0.9% saline solution, loosely covered with Parafilm®, is placed in 50° C. ultrasonic water bath. About ⅔ of saline solution should be covered by 50° C. water. Ultrasound is applied for at least 90 minutes.
3. Degassed saline is cooled down to room temperature before use.

Fritted Disc Funnel 9a Degassing
1. A large plastic container, filled with degassed 0.9% Saline, is placed in a vacuum desiccator.
2. The cleaned fritted disc funnel 2009a is placed inside the container and covered completely with degassed saline. Then a vacuum of 8 mbar or below is applied.
3. From time to time, the vacuum in the desiccator is released, allowing air bubbles inside the glass frit 2009b to escape. Air bubbles below the glass frit 2009b are removed by turning the frit upside down.
4. Degassing is completed after 5 hours.

Set-Up
1. Set up the apparatus components as shown in FIG. 31, with the exception of the sample assembly 2002.
2. Place the balance reservoir 2006 on the balance 2007. Place the Plexiglas® box 20012 over the balance and fluid reservoir, aligning the holes such that the glass tube 2004d can be inserted down through the box 2012 and through the cover 2008 without touching the balance reservoir 2006 or the cover 2008.
3. Fill filling reservoir 2005 with degassed 0.9% saline. Turn stopcocks 2004a and 2004b to allow tubing 2003, 2004c and 2004d, and balance reservoir 2006 to be filled with liquid. Allow any air bubbles to escape through the drain of stopcock 2004a. Close stopcocks 2004a and 2004b.
4. Connect the cleaned and degassed fritted disc funnel 2009a to the Tygon® tubing 2003 without introducing bubbles. Open stopcocks 2004a and 2004b to flush frit 2009b with the saline solution from filling reservoir 2005. During the flushing procedure, the frit 2009b is kept at lower height than the filling reservoir 2005. Fluid is removed from the funnel 2009a (after passing through frit 2009b) by inverting the funnel. Approximately 150 ml of fluid is used to flush the frit.
5. Attach the fritted disc funnel 2009a to the vertical slide 2001.
6. Relevel the glass frit 2009b using a small level that can fit inside the sample funnel 2009a and on the actual surface of the glass frit.
7. Turn stopcocks 2004a, 2004b to connect the fritted disc funnel 2009a with the balance reservoir 2006.
8. Zero the glass frit 2009b such that the surface of the fluid in the balance reservoir 2006 is level with the top surface of the glass frit 2009b. This may be achieved by connecting a suitable glass tube with an inner diameter of about 2006 mm to the "waste" outlet of stopcock 2004a via flexible tubing. The glass tube is held vertically alongside funnel 2009a and stopcock 2004a is set to allow fluid to flow from reservoir 2006 into the glass tube and fritted disc funnel. The top surface of the glass frit 2009b is adjusted to be at the same height as the fluid in the glass tube or less than 1 mm above the fluid in the glass tube. To accomplish this, either adjust the amount of liquid in the balance reservoir 2006, or reset the zero position on the vertical slide 2001. (This establishes the zero capillary suction height position of the frit). Raising the frit from this position by 10 cm would create a capillary suction height of 10 cm. The capillary suction height is the vertical distance between the top surface of the glass frit 2009b and the surface of the fluid in the balance reservoir when the top surface of the frit is at the same height or above the fluid in the balance reservoir). Once the height of the glass frit 200b has been adjusted, stopcock 2004a is reset to connect only the fritted disc funnel 2009a with the balance reservoir 2006. The glass tube and flexible tubing used to aid in adjusting the frit height may be removed.
9. Close the top of the fritted disc funnel 2009a with lid 2009f.
10. Wait for 10 minutes to reach equilibrium, then record the balance 2007 value in grams at 0 cm height.

Capillary Sorption Procedure
1. Position the fritted disc funnel 2009a at 80 cm capillary suction height. Verify that stopcocks 2004a and 2004b connect the fritted disc funnel 2009a with the balance reservoir 2006. (The filling reservoir 2005 is isolated by stopcock 2004b, and the drain is isolated by stopcock 2004a.) Equilibrate fritted disc funnel 2009a for 10 minutes.
2. Place the test sample 2009g concentrically in the cylinder 2009d and both concentrically on the surface of the glass frit 2009b. Insert the weight 2009c (having same diameter as the sample) into the cylinder 2009d.
3. Begin balance and time readings.
4. After reaching equilibrium (determined as described above), the equilibrium balance reading (g), sample time (s) and capillary suction height (cm) are recorded, and the height of the sample assembly 2002 is adjusted to the next capillary suction height in the absorption/desorption cycle. The last balance reading at each capillary suction height is taken as the equilibrium balance reading for that height. The elapsed time between the first balance reading and the last balance reading at each specified capillary suction height is the sample time for that height. The capillary suction heights are as follows (all heights in cm): 80, 70, 60, 50, 40, 35, 30, 25, 20, 15, 10, 9, 8, 7, 6, 5, 4.5, 4.0, 3.5, 3.0, 2.5, 2.0, 1.5, 1.0, 0.5, 0.

Equilibrium Capillary Absorption Values are derived from the data acquired during the decrease in capillary suction height from 80 to 0 cm. The Maximum Capillary Sorption Value is obtained at 0 cm capillary suction height. Desorption data may be obtained by an analogous procedure using the capillary suction heights listed above in reverse order, i.e. starting at 0 cm and ending at 80 cm.

Evaporation Rate

Even after taking all appropriate precautions listed above, some evaporative loss will occur. The evaporation rate is measured for each newly installed glass frit 2009b.

1. Move the sample assembly 2002 such that the glass frit 2009b is at 0 cm. Turn stopcocks 2004a and 2004b to connect the glass frit 2009b with the balance reservoir 2006. Allow the system to equilibrate for 10 minutes.
2. Place the cylinder 2009d concentrically on glass frit 2009b.
3. Record balance reading and time for 5.0 hours.

Glass Frit Correction

Since the glass frit 2009b is a porous structure, its equilibrium capillary sorption value at each capillary suction height must be determined and subtracted from the measured equilibrium capillary sorption value in order to obtain the absolute equilibrium sample capillary sorption value at that capillary suction height. The glass frit correction should be performed for each new glass frit used. Run the capillary sorption procedure as described above, except without test sample, to obtain the blank equilibrium balance reading (g) and blank time (s) at each specified capillary suction height (cm).

Calculations

Measured According to the Capillary Sorption Procedure Section Above:

Equilibrium Capillary Sorption Value(g) at capillary suction height$h$=Tare balance reading(g)−equilibrium balance reading(g) at suction height$h$ Measured According to Evaporation Rate Section Above:

$$\text{Evaporation Rate (g/sec)} = \frac{\text{(balance reading at 1 hr)} - \text{(balance reading at 5 hr)}}{4 \text{ hr} \times 3600 \text{ sec/hr}}$$

Measured According to the Glass Frit Correction Section Above:

Blank Capillary Sorption Value(g) at capillary suction height$h$=Tare balance reading(g)−blank equilibrium balance reading(g) at suction height$h$ Frit Correction Value(g) at height$h$=Blank Capillary Sorption Value(g)−(Blank Time(s)×Evaporation Rate(g/sec))

Equilibrium Capillary Suction Sorbent Capacity (CSSC):

CSSC(g/g) at capillary suction height$h$=(Equilibrium Sorption Value(g)−(Sample Time(s)×Sample Evaporation(g/sec)−Frit Correction Value(g))/Dry Weight of Sample(g)

The CSSC is expressed in grams of test liquid absorbed per gram of dry sample and is calculated for each capillary suction height for absorption.

The Maximum Equilibrium Capillary Sorption Capacity is the CSSC value at 0 cm capillary suction height.

Median Absorption Pressure:

The Median Absorption Pressure (MAP) is the Capillary Suction Height at which the material has 50% of its Maximum Equilibrium Capillary Sorption Capacity in the absorption phase of the measurement, and is expressed in cm (of test fluid).

Modified Fluid Acquisition Test

The Modified Fluid Acquisition ("MFA") Test is designed to measure the speed at which 0.9% saline solution is absorbed into an absorbent article that is compressed at 2.07 kPa. A known volume is introduced four times, each successive dose starting five (5) minutes after the previous dose has absorbed. Times needed to absorb each dose are recorded. All testing is performed in a room also maintained at about 23° C.±2 C.° and about 50%±2% relative humidity. The test fluid is 0.9% w/v saline solution and is prepared by weighing 9.0 g±0.05 g of NaCl into a weigh boat, transferring it into a 1 L volumetric flask, and diluting to volume with de-ionized water.

The MFA apparatus is depicted in FIG. 33 through FIG. 35b. The MFA apparatus comprises a bladder assembly 3001 and a top plate assembly 3200 that includes a deposition assembly 3100. A controller 3005 is used to 1) monitor the impedance across electrodes 3106, recording the time interval 0.9% saline solution is in a cylinder 3102, 2) interface with a liquid pump 3004 to start/stop dispensing, and 3) time intervals between dosing. The controller 3005 is capable of recording time events to ±0.01 sec. A house air supply 3014 is connected to a pressure regulator 3006 capable of delivering air at a suitable flow/pressure to maintain 2.07 kPa in the bladder assembly 3001. A liquid pump 3004 (Ismatec MCP-Z gear pump, available from Cole Palmer, Vernon Hills, Ill. or equivalent) capable of delivering a flow of 10-80 mL at a rate of 3-15 mL/s is attached to a steel tube 3104 of the deposition assembly 3100 via tygon tubing 3015.

The bladder assembly 3001 is constructed of 12.7 mm Plexiglas with an overall dimension of 80 cm long by 30 cm wide by 10 cm tall. A manometer 3007 to measure the pressure inside the assembly and a pressure gauge 3006 to regulate the introduction of air into the assembly are installed through two holes through the right side. A bladder 3013 is assembled by draping a 50 mm by 100 mm piece of silicone film, (thickness 0.02", Shore A durometer value of 20, available as Part #86435K85 from McMaster-Carr, Cleveland, Ohio) over the top of the box with enough slack that the film touches the bottom of the box at its center point. An aluminum frame 3003 with a flange is fitted over the top of the film and secured in place using mechanical clamps 3010. When in place, the assembly should be leak free at a pressure of 3.45 kPa. A front 3008 and back 3009 sample support 5 cm by 30 cm by 1 mm are used to anchor the sample. The absorbent article is attached to the top surface of the sample supports by either adhesive tape or mechanical "hook" fasteners. These supports can be adjusted along the length of the aluminum frame 3003 via a simple pin and hole system to accommodate different size absorbent articles and to correctly align their loading point.

The top plate assembly 3200 is constructed of an 80 cm by 30 cm piece of 12.7 mm Plexiglas reinforced with an aluminum frame 3109 to enhance rigidity. The plate has a cutout 170 mm wide by 201 mm long centered laterally on the plate, 170 mm from the front of the plate 3201 for mounting of the deposition assembly. In addition, the top plate has thirty-six (36) 3.2 mm diameter holes drilled through it distributed as shown in FIG. 35A. The holes prevent air from being trapped under the top plate as the bladder is inflated. The top plate assembly 3200 is connected to the bladder assembly 3001 via two hinges 3012. During use, the top assembly is closed onto the bladder assembly and locked into place using a mechanical clamp 3011.

Figure 34B:
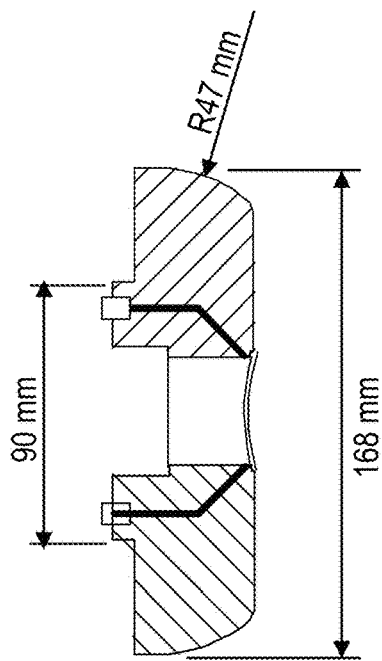
FIG. 34B is an end view of the curved component of FIG. 34A.
Figure 34E:
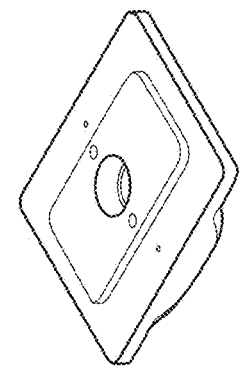
FIG. 34E is a top perspective view of the curved component of FIG. 34.
Figure 34D:
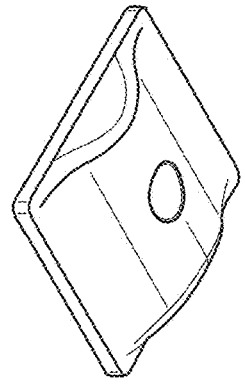
FIG. 34D is a bottom perspective view of the curved component of FIG. 34A.
Figure 34A:
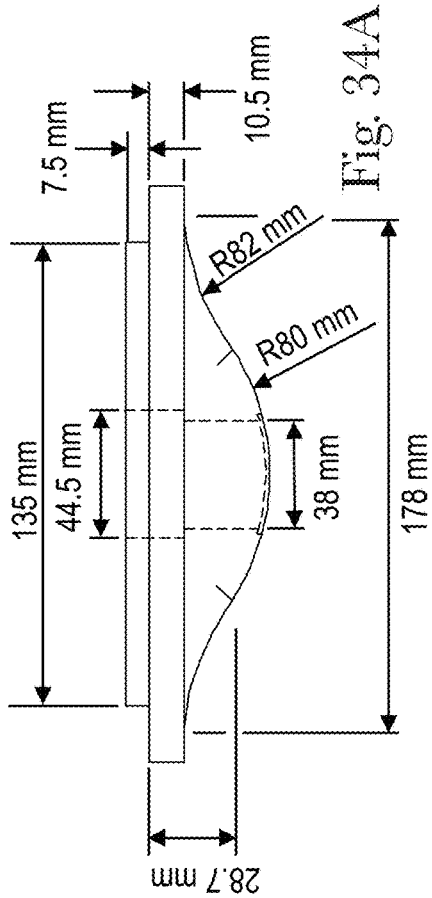
FIG. 34A is a side view of the curved component used in the Modified Fluid Acquisition Test.
Figure 34C:
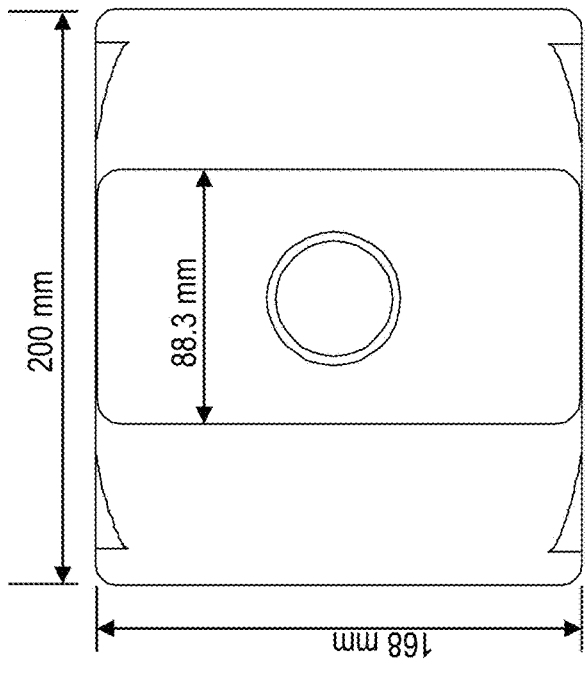
FIG. 34C is a bottom view of the curved component of FIG. 34A.

The deposition assembly 3100 is fitted into the top plate 3200 and includes 1) a liquid introduction cylinder 3102, 2) a curved surface 3101 at the loading point of the absorbent article and 3) electrodes 3106 that are used to detect fluid in the cylinder 3102. The detailed dimensions of the curved component are provided in FIG. 34A to FIG. 34E. FIG. 34A is a side view of the curved component. FIG. 34B is an end view of the curved component. FIG. 34C is a bottom view of the curved component. FIG. 34D is a bottom perspective view of the curved component. FIG. 34E is a top perspective view of the curved component. This curved component can be milled or 3D printed. The top portion of the introduction cylinder is a 50.8 mm O.D. Plexiglas cylinder 3102 with a 38.1 mm I.D. This is fitted into the curved component to give the introduction cylinder a total height of 100 mm. Imbedded electrodes run from connectors on the upper surface of the curved component and terminate flush with an inside wall of the introduction cylinder, 2 mm from the bottom of the cylinder. The two electrodes are positioned 180 degrees apart. A nylon screen 3107 is cut and affixed flush with the bottom of the cylinder such that the sample cannot swell into the cylinder. A 5 mm semi-circle is cut in the screen in the immediate area of the two electrodes. The deposition assembly is inserted into the top plate as shown in FIG. 35A such that the curved surface is flush with the bottom of the top-plate assembly 3200. The introduction cylinder 3102 is topped with a loose-fitting nylon cap 3103. The cap has a 6.35 mm O.D. steel tube 3104 inserted through its center. When the cap is in place, the bottom of the tube ends 20 mm above the screen 3107. The cap also has an air hole 3105 to ensure negative pressure does not impede the absorption speed.

All sample articles are conditioned at 23° C.±2 C.° and about 50%±2% relative humidity for two hours prior to testing. The absorbent article is first prepared by excising any inner or outer leg cuffs, waist caps, elastic ears or side panels, taking care not to disturb the top sheet that resides above the article's core region. Place the absorbent article flat onto a lab bench and identify the intersection of the longitudinal centerline with the size dependent loading point (as defined in Table 3).

TABLE 3

Loading Points, Volumes, and Flow rate for Acquisition Testing:

| Diaper Size | Approximate Baby Weight Pounds | Loading Point from front of Core* Boy mm | Loading Point from front of Core* Girl mm | Single Dose Volume mL | Flow Rate mL/s |
|---|---|---|---|---|---|
| 1 | 8 to 13 | 64 | 64 | 24 | 8 |
| 2 | 13 to 17 | 76 | 89 | 24 | 8 |
| 3 | 17 to 28 | 89 | 114 | 50 | 10 |
| 4-6 | 28+ | 102 | 127 | 75 | 15 |

*The boy loading point is used for unisex diapers.

Attach the front end of the absorbent article to the top surface of the front sample plate 3008 by either adhesive tape or mechanical "hook" fasteners with the top sheet facing upward. The placement is such that just the chassis and not the absorptive core overlays the plate. The sample plate 3008 is attached to the aluminum frame 3003 such that the size-dependent Loading Point (as defined in Table 2) of the absorbent article will be centered longitudinally and laterally within the cylinder 3102 when the top plate assembly has been closed. The back end of the absorbent article is secured to the back sample plate 3009 by either adhesive tape or mechanical "hook" fasteners, once again ensuring that only the chassis and not the absorptive core overlays the plate. The back sample plate 3009 is then attached to the aluminum frame 3003 such that the article is taunt but not stretched. The top plate assembly is closed and fastened, and the bladder is inflated to 2.07 kPa±0.07 kPa. The pressure is maintained at this level during the complete loading sequence of the test.

The pump 3004 is primed and then calibrated to deliver the size-dependent volume and flow rate selected from Table 2. Volume and flow rate must be within ±2% of target. The cap 3103 is placed into the cylinder 3102. The controller 3005 is started, which in turn delivers the first dose of 0.9% saline solution. After the volume has been absorbed, the controller waits for 5.0 minutes before addition of the next dose. This cycle is repeated for a total of four doses. If the fluid leaks out of or around the article (i.e., is not absorbed into the article) then the test is aborted. Also if any acquisition time exceeds 1200 seconds, the test is aborted. The acquisition time is defined as the difference between the start time (i.e., when the 0.9% saline is first introduced into the cylinder and that conducting fluid completes the circuit between the electrodes) and the stop time (i.e., when the fluid has completely drained from the cylinder and the circuit between the electrodes is broken). Acquisition times are recorded by the controller for each dose to the nearest 0.01 second. After the last dose is acquired, pressure is applied for an additional 10 minutes. Open the pressure relief valve 3016 to deflate the bladder and then remove the sample from the acquisition system.

In like fashion, run a total of five (5) replicates for each absorbent article to be evaluated. Calculate and report the Acquisition Times (sec) for each dose as the arithmetic mean of the replicates to the nearest 0.01 sec.

Light Touch Dryness Test

The Light Touch Dryness ("LTD") Test is performed immediately after the MFA Test. The test comprises measuring the mass of fluid expressed from the absorbent article under pressure after loading by the MFA protocol. Whatman #1 filter paper sheets are used as the rewet substrate and are conditioned at 23° C.±2 C.° and about 50%±2% relative humidity overnight before use. All testing is performed in a room also maintained at about 23° C.±2 C.° and about 50%±2% relative humidity.

Equipment for this test includes a Plexiglas disk 70.0 mm in diameter and 20 mm thick and a stainless steel confining weight that rests upon it. The mass of the disk and confining weight combined is 812 g±2 g which corresponds to a pressure of 2.07 kPa. Whatman #1 filter paper is die cut into 70.0 mm diameter circles and stacks of four (4) assembled for use during rewet testing. Measure and record the mass of the dry filter paper stack and record to the nearest 0.0001 g.

Within 30 seconds after the conclusion of the MFA test, remove the absorbent article from the acquisition apparatus and place flat on a bench top with the top sheet facing upward. Place a pre-weighed stack of Whatman #1 filter paper centered at the loading point (as determined previously in the MFA test), place the Plexiglass disk onto the stack, and gently place the confining weight onto the disk. Wait for 30.0 sec±0.5 sec and remove the weight and disc. Immediately measure the mass of the wet filter paper and record to the nearest 0.0001 g. Calculate the modified rewet value as the difference between the wet and dry weight of the stack and record to the nearest 0.1 mg.

In like fashion run a total of five (5) replicates for each absorbent article to be evaluated. Calculate and report the Light Touch Dryness (mg) for each dose as the arithmetic mean of the replicates to the nearest 0.1 mg.

Collagen Rewet Test

The Collagen Rewet Test is performed immediately after the MFA Test. The Collagen Rewet Test comprises measuring the mass of fluid expressed from an absorbent article under pressure after loading by the MFA protocol. Collagen sheets are used as the rewet substrate. A suitable collagen is Naturin Coffi collagen sheets (available Naturin GmbH & KG, Germany) or equivalent. Upon receipt, the collagen sheets are stored at about 23° C.±2 C.° and about 50%±2% relative humidity for 2 hours prior to testing. All testing is performed in a room also maintained at about 23° C.±2 C.° and about 50%±2% relative humidity.

Equipment for the test consists of a Plexiglas disk 70.0 mm in diameter and 20 mm thick and a stainless steel confining weight that rests upon it. The mass of the disk and confining weight combined is 9100 g±2 g which corresponds to a pressure of 23.2 kPa. Collagen sheets are die cut into 70.0 mm diameter circles and stacks of four (4) assembled for use during rewet testing. Measure and record the mass of the dry filter paper stack and record to the nearest 0.0001 g.

Within 30 seconds after the conclusion of the MFA test, remove the absorbent article from the acquisition apparatus and place it flat on a bench top with the top sheet facing upward. Then, place a pre-weighed stack of collagen centered at the loading point (as determined previously in the MFA test), place the Plexiglass disk onto the stack, and gently place the confining weight onto the disk. Wait for 15.0 seconds±0.5 seconds and remove the weight and disc. Immediately measure the mass of the wet filter paper and record to the nearest 0.0001 g. Calculate the Collagen Rewet value as the difference between the wet and dry weight of the stack and record to the nearest 0.1 mg.

In like fashion, run a total of five (5) replicates for each absorbent article to be evaluated. Calculate and report the Collagen Rewet (mg) for each dose as the arithmetic mean of the replicates to the nearest 0.1 mg.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. An absorbent article comprising:
   a three-dimensional, liquid permeable topsheet comprising:
      a first nonwoven layer forming a portion of a wearer-facing surface of the absorbent article, wherein the first nonwoven layer comprises a hydrophobic material; and
      a second nonwoven layer comprising a hydrophilic material, wherein the first nonwoven layer is joined to the second nonwoven layer;
      wherein the topsheet comprises a plurality of recesses, a plurality of projections, and a plurality of land areas, wherein the land areas surround at least a majority of the plurality of projections and a plurality of the recesses, wherein the plurality of recesses, the plurality of projections, and the plurality of land areas, together form a first three-dimensional surface on a first side of the topsheet and a second three-dimensional surface on a second side of the topsheet, wherein a majority of the projections have a z-directional height in the range of about 500 µm to about 4000 µm, according to the Projection Height Test, wherein a majority of the recesses define an aperture at a location most distal from a top peak of an adjacent projection, and wherein the majority of the recesses have a z-directional height in the range of about 500 µm to about 2000 µm, according to the Recess Height Test;
   wherein the topsheet has an overall z-directional height in the range of about 600 µm to about 6000 µm, according to the Overall Substrate Height Test;
   wherein a portion of the projections and a portion of the recesses are formed by a portion of the first nonwoven layer and a portion of the second nonwoven layer;
   wherein the apertures are formed through the first nonwoven layer and through the second nonwoven layer;
   wherein the topsheet has a basis weight in the range of about 20 gsm to about 50 gsm, according to the Basis Weight Test;
   a liquid impermeable backsheet;
   a material positioned at least partially intermediate the topsheet and the backsheet; and
   an acquisition material positioned at least partially intermediate the topsheet and the material;
   wherein the topsheet comprises a first Median Absorption Pressure having a first value;
   wherein the acquisition material comprises a Median Absorption Pressure having a second value;
   wherein the material comprises a third Median Absorption Pressure having a third value;
   wherein the second value is intermediate or equal to the first value and the third value;
   wherein the topsheet has an equilibrium capillary suction sorbent capacity greater than 10 g/g at 100% saturation, according to the Capillary Sorption Test; and
   wherein the acquisition material has an equilibrium capillary suction sorbent capacity less than 7 g/g at 100% saturation, according to the Capillary Sorption Test.

2. The absorbent article of claim 1, wherein the material comprises cross-linked cellulosic fibers, wherein the absorbent article comprises an absorbent core positioned intermediate the cross-linked cellulosic fibers and the liquid impermeable backsheet, wherein the absorbent core comprises an absorbent material, and wherein the absorbent material comprises at least 85% superabsorbent polymers by weight of the absorbent material.

3. The absorbent article of claim 1, wherein the material comprises an absorbent core.

4. The absorbent article of claim 1, wherein the absorbent article has a modified fluid acquisition in the range of about 70 seconds and about 200 seconds, according to the Modified Fluid Acquisition Test.

5. The absorbent article of claim 1, wherein the absorbent article has a collagen rewet in the range of about 30 mg and about 120 mg, according to the Collagen Rewet Test.

6. The absorbent article of claim 1, wherein the absorbent article has a light touch dryness in the range of about 20 mg to about 80 mg, according to the Light Touch Dryness Test.

7. The absorbent article of claim 1, wherein the first value is in the range of about 2 cm to about 3 cm, according to the Capillary Sorption Test, wherein the second value is in the range of about 4 cm to about 7 cm, according to the Capillary Sorption Test, and wherein the third value is in the range of about 8 cm to about 10 cm, according to the Capillary Sorption Test.

8. The absorbent article of claim 1, wherein a majority of the apertures in the topsheet have an effective aperture area in the range of about 0.5 mm$^2$ to about 3 mm$^2$, according to the Aperture Test, and wherein the topsheet has a % effective open area in the range of about 5% to about 25%, according to the Aperture Test.

9. The absorbent article of claim 1, wherein the first nonwoven layer of the topsheet comprises a plurality of first fibers, wherein the second nonwoven layer of the topsheet comprises a plurality of second fibers, and wherein the first and second fibers are different.

10. The absorbent article of claim 1, wherein four apertures are formed around each projection, and wherein four projections are formed around each aperture.

11. The absorbent article of claim 1, wherein two adjacent apertures are separated by a projection and a land area along a lateral axis of the substrate, wherein two adjacent projections are separated by an aperture and a land area along the lateral axis of the substrate, wherein two adjacent apertures are separated by a projection and a land area along a longitudinal axis of the substrate, and wherein two adjacent projections are separated by an aperture and a land area along the longitudinal axis of the substrate.

12. The absorbent article of claim 1, wherein substantially all of the recesses define an aperture, and wherein substantially all of the projections comprise a hollow arched portion.

13. The absorbent article of claim 1, wherein the apertures comprise a first set of apertures together forming a first line in the substrate and a second set of apertures together forming a second line in the substrate, wherein the first line is generally parallel with the second line, and wherein the apertures are formed through the first nonwoven layer and the second nonwoven layer.

14. The absorbent article of claim 1, wherein a perimeter of the majority of the apertures forms a first plane of the bottommost portion of the substrate, wherein a top peak of the majority of the projections forms a second plane of the topmost portion of the substrate, and wherein the land areas are positioned intermediate the first plane and the second plane.

15. The absorbent article of claim 1, wherein the first three-dimensional surface has a geometric roughness value in the range of about 3.0 to about 3.6, according to the Descriptive Analysis Roughness Test.

16. The absorbent article of claim 1, wherein the first nonwoven layer comprises fibers that are at least 0.5 denier greater than a denier of the fibers of the second layer.

17. The absorbent article of claim 1, wherein the first nonwoven layer of the topsheet comprises fibers having a denier in the range of about 3 to about 5, and wherein the second nonwoven layer of the topsheet comprises fibers having a denier in the range of about 1 to about 3.

18. The absorbent article of claim 1, wherein the first nonwoven layer has a basis weight in the range of about 0.4 to about 3 times greater than a basis weight of the second nonwoven layer.

19. The absorbent article of claim 1, wherein at least a portion of the material is positioned directly under the acquisition material.

20. The absorbent article of claim 1, wherein the second value is intermediate the first value and the third value.

* * * * *